US012637502B2

(12) United States Patent
Cukierman et al.

(10) Patent No.: US 12,637,502 B2
(45) Date of Patent: May 26, 2026

(54) NETRIN G1 POLYPEPTIDES

(71) Applicant: Institute For Cancer Research, Philadelphia, PA (US)

(72) Inventors: Edna Cukierman, Philadelphia, PA (US); Ralph Francescone, Philadelphia, PA (US); Debora Vendramini-Costa, Philadelphia, PA (US); Kristopher Raghavan, Philadelphia, PA (US); Janusz Franco-Barraza, Philadelphia, PA (US); Roland Dunbrack, Philadelphia, PA (US)

(73) Assignee: INSTITUTE FOR CANCER RESEARCH, Philadelphia, PA (US)

( * ) Notice: Subject to any disclaimer, the term of this patent is extended or adjusted under 35 U.S.C. 154(b) by 216 days.

(21) Appl. No.: 17/604,891

(22) PCT Filed: Apr. 24, 2020

(86) PCT No.: PCT/US2020/029781
§ 371 (c)(1),
(2) Date: Oct. 19, 2021

(87) PCT Pub. No.: WO2020/219854
PCT Pub. Date: Oct. 29, 2020

(65) Prior Publication Data
US 2022/0289823 A1 Sep. 15, 2022

Related U.S. Application Data

(60) Provisional application No. 62/838,593, filed on Apr. 25, 2019.

(51) Int. Cl.
| | |
|---|---|
| *A61K 38/17* | (2006.01) |
| *A61P 35/00* | (2006.01) |
| *C07K 11/00* | (2006.01) |
| *C07K 14/475* | (2006.01) |
| *C07K 14/71* | (2006.01) |
| *C07K 16/22* | (2006.01) |

(52) U.S. Cl.
CPC .............. *C07K 14/71* (2013.01); *A61P 35/00* (2018.01); *C07K 11/00* (2013.01); *C07K 14/475* (2013.01); *C07K 16/22* (2013.01); *C07K 2317/76* (2013.01)

(58) Field of Classification Search
None
See application file for complete search history.

(56) References Cited

U.S. PATENT DOCUMENTS

| | | |
|---|---|---|
| 2010/0196426 A1 | 8/2010 | Skog et al. |
| 2011/0236903 A1 | 9/2011 | McClelland et al. |
| 2012/0178690 A1 | 7/2012 | Kennedy |
| 2014/0099340 A1 | 4/2014 | June et al. |

FOREIGN PATENT DOCUMENTS

| | | |
|---|---|---|
| CA | 2988388 | 10/2016 |
| WO | 2006/054000 | 3/2006 |
| WO | 2011119484 | 9/2011 |
| WO | 2013040412 | 3/2013 |
| WO | 2016172722 | 10/2016 |
| WO | 2019074915 | 4/2019 |

OTHER PUBLICATIONS

Wells (1990). Biochemistry 29:8509-8517.*
Ngo et al. (1994). The Protein Folding Problem and Tertiary Structure Prediction, pp. 492-495.*
Francescone et al. (2021) Cancer Discovery. 11(2):446-479).*
Arber et al. (2016) Blood 127:2391-2405.*
Swerdlow et al. (2016) Blood 127:2375-2390.*
Notice of Allowance dated May 24, 2024 in related U.S. Appl. No. 16/754,877.
Jia et al., "FAP-a (Fibroblast activation protein-a) is involved in the control of human breast cancer cell line growth and motility via the FAK pathway", BMC Cell Biology, 2014, 15(16), pp. 1-14.
GenBank, "Netrin G1 precursor, partial [Mustela putorius furo]", Accession No. AES03183, 2013, pp. 1.
GenBank, "Hypothetical protein [Mycoplasmopsis bovigenitalium]", Accession No. WP_129687782, 2019, pp. 1.
GenBank, "Hypothetical protein EHP00_239 [Ecytonucleospora hepatopenaei]", Accession No. OQS54885, 2017, pp. 1-2.
Sho et al., "A prognostic mutation panel for predicting cancer recurrence in stages II and III colorectal cancer", J Surg Oncol, 2017, 116(8), pp. 996-1004.
Non-Final Office Action dated Sep. 20, 2023 in related U.S. Appl. No. 16/754,877.
Sherman et al., "Vitamin D Receptor-Mediated Stromal Reprogramming Suppresses Pancreatitis and Enhances Pancreatic Cancer Therapy", Cell, 2014, 159(1), pp. 80-93.
Non-Final Office Action dated Jun. 15, 2022 in related U.S. Appl. No. 16/754,877.
Seiradake et al., "Structural basis for cell surface patterning through NetrinG&ndashl NGL interactions", The EMBO Journal, 2011, 30(21), pp. 4479-4488.
Goldman et al., "The clasp between NetrinG and NGL becomes crystal clear", The EMBO Journal, 2011, 30(21), pp. 4342-4344.
Final Office Action dated Mar. 16, 2023 in related U.S. Appl. No. 16/754,877.
Advisory Action dated Jun. 2, 2023 in related U.S. Appl. No. 16/754,877.

(Continued)

*Primary Examiner* — Christine J Saoud
*Assistant Examiner* — Jon M Lockard
(74) *Attorney, Agent, or Firm* — DUANE MORRIS LLP

(57) ABSTRACT

The present disclosure provides polypeptides of netrin G1 (NetG1) and its cell surface receptor netrin G1 ligand (NGL1), and antibodies thereto, and methods of making such antibodies. The disclosure also provides uses of these NetG1 and NGL1 polypeptides, and antibodies thereto, in methods of treating cancers and diseases, including chronic fibrosis, inflammation, and inflammation-related diseases.

6 Claims, 26 Drawing Sheets
(20 of 26 Drawing Sheet(s) Filed in Color)

Specification includes a Sequence Listing.

(56) References Cited

OTHER PUBLICATIONS

Francescone et al., "Abstract 2038: NG1/NGL1 engagement supports PDAC development via CAF to PDAC nutrition and CAF-regulated immunosuppression", Cancer Research, 2019, 79, pp. 2038.

Final Office Action dated Feb. 9, 2024 in related U.S. Appl. No. 16/754,877.

Lu et al., "The MLL1-H3K4me3 Axis-Mediated PD-L1 Expression and Pancreatic Cancer Immune Evasion", J Natl Cancer Inst, 2017, 109(6), pp. 1-12.

Rollins, "Netrin G1 in Desmoplastic Fibroblast Enhances Interactions with Pancreatic Cancer Cells", MS Dissertation Drexel University, Jul. 2016, pp. 1-61.

Valente et al., "Distribution of interferon-gamma receptor in human tissues", Eur J Immunol, 1992, 22, pp. 2403-2412.

International Search Report and Written Opinion for PCT Application PCT/US2018/054994. (2018).

Niimi et al., "Monoclonal antibodies discriminating netrin-G1 and netrin-G2 neuronal pathways", K Neuroimmunol, 2007, 192(1-2), pp. 99-104.

Cukierman et al., "Taking cell-matrix adhesions to the third dimension", Science, 2001, 294(5547), pp. 1708-1712.

Francescone et al., "The NetrinG1/NGL-1 Axis promotes pancreatic tumorigenesis through cancer associated fibroblast driven nutritional support and immunosuppression", BioRxiv, 2018, doi: http://dx.doi.org/10.1101/330209, pp. 1-60.

Franco-Barraza et al., "Matrix-regulated integrin avb5 maintains a5b1-dependent desmoplastic traits prognostic of neoplastic recurrence", eLife, 2017, 6, pp. e20600.

Nakashiba, Toshiaki et al., "Netrin-G1: a Novel Glycosyl Phosphatidylinositol-Linked Mammalian Netrin That Is Functionally Divergent from Classical Netrins", The Journal of Neuroscience, Sep. 1, 2000, 20(17):6540-6550.

* cited by examiner

+ NGL1

+ NetG1

Ctl KRAS Viability

Ctl. KRAS Cell Viability

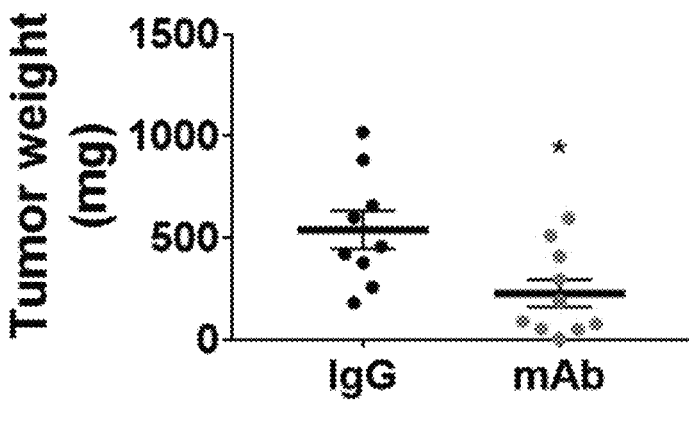
FIG. 9A
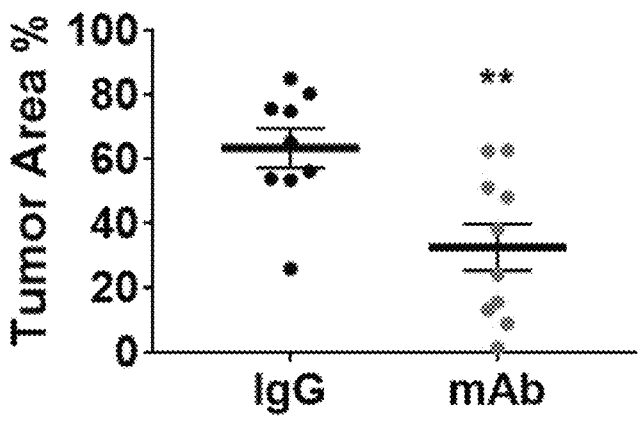
FIG. 9B
FIG. 9C

```
SEQUENCE LISTING

<160> NUMBER OF SEQ ID NOS: 36

<210> SEQ ID NO 1
<211> LENGTH: 14
<212> TYPE: PRT
<213> ORGANISM: artificial sequence
<220> FEATURE:
<223> OTHER INFORMATION: NetG1 polypeptide

<400> SEQUENCE: 1

Thr Phe Cys Ala Met Gly Asn Pro Tyr Met Cys Asn Asn Glu
1               5                   10

<210> SEQ ID NO 2
<211> LENGTH: 9
<212> TYPE: PRT
<213> ORGANISM: artificial sequence
<220> FEATURE:
<223> OTHER INFORMATION: NetG1 polypeptide

<400> SEQUENCE: 2

Gly Asn Pro Tyr Met Cys Asn Asn Glu
1               5

<210> SEQ ID NO 3
<211> LENGTH: 16
<212> TYPE: PRT
<213> ORGANISM: artificial sequence
<220> FEATURE:
```

<223> OTHER INFORMATION: NetG1 polypeptide

<400> SEQUENCE: 3

Ala Val Gly Glu Ile Phe Val Asp Glu Leu His Leu Ala Arg Tyr Phe
1               5                   10                  15

<210> SEQ ID NO 4
<211> LENGTH: 6
<212> TYPE: PRT
<213> ORGANISM: artificial sequence
<220> FEATURE:
<223> OTHER INFORMATION: NetG1 polypeptide

<400> SEQUENCE: 4

Val Gly Glu Ile Phe Val
1               5

<210> SEQ ID NO 5
<211> LENGTH: 11
<212> TYPE: PRT
<213> ORGANISM: artificial sequence
<220> FEATURE:
<223> OTHER INFORMATION: NetG1 polypeptide

<400> SEQUENCE: 5

Glu Tyr Ser Thr Gly Tyr Thr Thr Asn Ser Lys
1               5                   10

<210> SEQ ID NO 6
<211> LENGTH: 6
<212> TYPE: PRT
<213> ORGANISM: artificial sequence
<220> FEATURE:
<223> OTHER INFORMATION: NetG1 polypeptide

<400> SEQUENCE: 6

Ser Thr Gly Tyr Thr Thr
1               5

<210> SEQ ID NO 7
<211> LENGTH: 12
<212> TYPE: PRT
<213> ORGANISM: artificial sequence
<220> FEATURE:
<223> OTHER INFORMATION: NetG1 polypeptide

<400> SEQUENCE: 7

Ala Thr Asp Cys Leu Asp Ala Phe His Met Asp Pro
1               5                   10

<210> SEQ ID NO 8
<211> LENGTH: 9
<212> TYPE: PRT
<213> ORGANISM: artificial sequence
<220> FEATURE:
<223> OTHER INFORMATION: NetG1 polypeptide

<400> SEQUENCE: 8

Ala Thr Asp Cys Leu Asp Ala Phe His
1               5

<210> SEQ ID NO 9
<211> LENGTH: 14
<212> TYPE: PRT
<213> ORGANISM: artificial sequence
<220> FEATURE:
<223> OTHER INFORMATION: NetG1 polypeptide

<400> SEQUENCE: 9

Thr Phe Cys Ala Met Gly Asn Pro Thr Met Cys Asn Asn Glu
1               5                   10

<210> SEQ ID NO 10
<211> LENGTH: 9
<212> TYPE: PRT
<213> ORGANISM: artificial sequence
<220> FEATURE:
<223> OTHER INFORMATION: NetG1 polypeptide

<400> SEQUENCE: 10

Gly Asn Pro Thr Met Cys Asn Asn Glu
1               5

<210> SEQ ID NO 11
<211> LENGTH: 14
<212> TYPE: PRT
<213> ORGANISM: artificial sequence
<220> FEATURE:
<223> OTHER INFORMATION: NetG1 polypeptide

<400> SEQUENCE: 11

Val Cys Ser Cys Ser Asn Gln Phe Ser Lys Val Ile Cys Val
1               5                   10

<210> SEQ ID NO 12
<211> LENGTH: 539
<212> TYPE: PRT
<213> ORGANISM: homo sapien

<400> SEQUENCE: 12

Met Tyr Leu Ser Arg Phe Leu Ser Ile His Ala Leu Trp Val Thr Val
1               5                   10                  15

Ser Ser Val Met Gln Pro Tyr Pro Leu Val Trp Gly His Tyr Asp Leu
                20                  25                  30

Cys Lys Thr Gln Ile Tyr Thr Glu Glu Gly Lys Val Trp Asp Tyr Met
            35                  40                  45

Ala Cys Gln Pro Glu Ser Thr Asp Met Thr Lys Tyr Leu Lys Val Lys
        50                  55                  60

Leu Asp Pro Pro Asp Ile Thr Cys Gly Asp Pro Pro Glu Thr Phe Cys
65                  70                  75                  80

Ala Met Gly Asn Pro Tyr Met Cys Asn Asn Glu Cys Asp Ala Ser Thr
                85                  90                  95

Pro Glu Leu Ala His Pro Pro Glu Leu Met Phe Asp Phe Glu Gly Arg
                100                 105                 110

His Pro Ser Thr Phe Trp Gln Ser Ala Thr Trp Lys Glu Tyr Pro Lys
            115                 120                 125

Pro Leu Gln Val Asn Ile Thr Leu Ser Trp Ser Lys Thr Ile Glu Leu
        130                 135                 140

Thr Asp Asn Ile Val Ile Thr Phe Glu Ser Gly Arg Pro Asp Gln Met
145                 150                 155                 160

Ile Leu Glu Lys Ser Leu Asp Tyr Gly Arg Thr Trp Gln Pro Tyr Gln
                165                 170                 175

Tyr Tyr Ala Thr Asp Cys Leu Asp Ala Phe His Met Asp Pro Lys Ser
            180                 185                 190

Val Lys Asp Leu Ser Gln His Thr Val Leu Glu Ile Ile Cys Thr Glu
            195                 200                 205

```
Glu Tyr Ser Thr Gly Tyr Thr Thr Asn Ser Lys Ile Ile His Phe Glu
    210             215                 220

Ile Lys Asp Arg Phe Ala Phe Phe Ala Gly Pro Arg Leu Arg Asn Met
225             230                 235                 240

Ala Ser Leu Tyr Gly Gln Leu Asp Thr Thr Lys Lys Leu Arg Asp Phe
                245                 250                 255

Phe Thr Val Thr Asp Leu Arg Ile Arg Leu Leu Arg Pro Ala Val Gly
            260                 265                 270

Glu Ile Phe Val Asp Glu Leu His Leu Ala Arg Tyr Phe Tyr Ala Ile
        275                 280                 285

Ser Asp Ile Lys Val Arg Gly Arg Cys Lys Cys Asn Leu His Ala Thr
    290                 295                 300

Val Cys Val Tyr Asp Asn Ser Lys Leu Thr Cys Glu Cys Glu His Asn
305                 310                 315                 320

Thr Thr Gly Pro Asp Cys Gly Lys Cys Lys Lys Asn Tyr Gln Gly Arg
                325                 330                 335

Pro Trp Ser Pro Gly Ser Tyr Leu Pro Ile Pro Lys Gly Thr Ala Asn
            340                 345                 350

Thr Cys Ile Pro Ser Ile Ser Ser Ile Gly Asn Cys Glu Cys Phe Gly
        355                 360                 365

His Ser Asn Arg Cys Ser Tyr Ile Asp Leu Leu Asn Thr Val Ile Cys
    370                 375                 380

Val Ser Cys Lys His Asn Thr Arg Gly Gln His Cys Glu Leu Cys Arg
385                 390                 395                 400

Leu Gly Tyr Phe Arg Asn Ala Ser Ala Gln Leu Asp Asp Glu Asn Val
                405                 410                 415

Cys Ile Glu Cys Tyr Cys Asn Pro Leu Gly Ser Ile His Asp Arg Cys
            420                 425                 430

Asn Gly Ser Gly Phe Cys Glu Cys Lys Thr Gly Thr Thr Gly Pro Lys
        435                 440                 445

Cys Asp Glu Cys Leu Pro Gly Asn Ser Trp His Tyr Gly Cys Gln Pro
    450                 455                 460

Asn Val Cys Asp Asn Glu Leu Leu His Cys Gln Asn Gly Gly Thr Cys
465                 470                 475                 480

His Asn Asn Val Arg Cys Leu Cys Pro Ala Ala Tyr Thr Gly Ile Leu
                485                 490                 495

Cys Glu Lys Leu Arg Cys Glu Glu Ala Gly Ser Cys Gly Ser Asp Ser
            500                 505                 510

Gly Gln Gly Ala Pro Pro His Gly Ser Pro Ala Leu Leu Leu Leu Thr
            515                 520                 525

Thr Leu Leu Gly Thr Ala Ser Pro Leu Val Phe
    530                 535

<210> SEQ ID NO 13
<211> LENGTH: 640
<212> TYPE: PRT
<213> ORGANISM: homo sapien

<400> SEQUENCE: 13

Met Leu Asn Lys Met Thr Leu His Pro Gln Gln Ile Met Ile Gly Pro
1               5                   10                  15

Arg Phe Asn Arg Ala Leu Phe Asp Pro Leu Leu Val Val Leu Leu Ala
                20                  25                  30

Leu Gln Leu Leu Val Val Ala Gly Leu Val Arg Ala Gln Thr Cys Pro
            35                  40                  45
```

-continued

```
Ser Val Cys Ser Cys Ser Asn Gln Phe Ser Lys Val Ile Cys Val Arg
    50              55              60

Lys Asn Leu Arg Glu Val Pro Asp Gly Ile Ser Thr Asn Thr Arg Leu
65              70              75              80

Leu Asn Leu His Glu Asn Gln Ile Gln Ile Ile Lys Val Asn Ser Phe
            85              90              95

Lys His Leu Arg His Leu Glu Ile Leu Gln Leu Ser Arg Asn His Ile
            100             105             110

Arg Thr Ile Glu Ile Gly Ala Phe Asn Gly Leu Ala Asn Leu Asn Thr
        115             120             125

Leu Glu Leu Phe Asp Asn Arg Leu Thr Thr Ile Pro Asn Gly Ala Phe
    130             135             140

Val Tyr Leu Ser Lys Leu Lys Glu Leu Trp Leu Arg Asn Asn Pro Ile
145             150             155             160

Glu Ser Ile Pro Ser Tyr Ala Phe Asn Arg Ile Pro Ser Leu Arg Arg
            165             170             175

Leu Asp Leu Gly Glu Leu Lys Arg Leu Ser Tyr Ile Ser Glu Gly Ala
            180             185             190

Phe Glu Gly Leu Ser Asn Leu Arg Tyr Leu Asn Leu Ala Met Cys Asn
        195             200             205

Leu Arg Glu Ile Pro Asn Leu Thr Pro Leu Ile Lys Leu Asp Glu Leu
    210             215             220

Asp Leu Ser Gly Asn His Leu Ser Ala Ile Arg Pro Gly Ser Phe Gln
225             230             235             240

Gly Leu Met His Leu Gln Lys Leu Trp Met Ile Gln Ser Gln Ile Gln
            245             250             255

Val Ile Glu Arg Asn Ala Phe Asp Asn Leu Gln Ser Leu Val Glu Ile
            260             265             270

Asn Leu Ala His Asn Asn Leu Thr Leu Leu Pro His Asp Leu Phe Thr
        275             280             285

Pro Leu His His Leu Glu Arg Ile His Leu His His Asn Pro Trp Asn
    290             295             300

Cys Asn Cys Asp Ile Leu Trp Leu Ser Trp Trp Ile Lys Asp Met Ala
305             310             315             320

Pro Ser Asn Thr Ala Cys Cys Ala Arg Cys Asn Thr Pro Pro Asn Leu
            325             330             335

Lys Gly Arg Tyr Ile Gly Glu Leu Asp Gln Asn Tyr Phe Thr Cys Tyr
            340             345             350

Ala Pro Val Ile Val Glu Pro Pro Ala Asp Leu Asn Val Thr Glu Gly
        355             360             365

Met Ala Ala Glu Leu Lys Cys Arg Ala Ser Thr Ser Leu Thr Ser Val
    370             375             380

Ser Trp Ile Thr Pro Asn Gly Thr Val Met Thr His Gly Ala Tyr Lys
385             390             395             400

Val Arg Ile Ala Val Leu Ser Asp Gly Thr Leu Asn Phe Thr Asn Val
            405             410             415

Thr Val Gln Asp Thr Gly Met Tyr Thr Cys Met Val Ser Asn Ser Val
            420             425             430

Gly Asn Thr Thr Ala Ser Ala Thr Leu Asn Val Thr Ala Ala Thr Thr
        435             440             445

Thr Pro Phe Ser Tyr Phe Ser Thr Val Thr Val Glu Thr Met Glu Pro
    450             455             460
```

-continued

```
Ser Gln Asp Glu Ala Arg Thr Thr Asp Asn Asn Val Gly Pro Thr Pro
465             470             475             480

Val Val Asp Trp Glu Thr Thr Asn Val Thr Thr Ser Leu Thr Pro Gln
                485             490             495

Ser Thr Arg Ser Thr Glu Lys Thr Phe Thr Ile Pro Val Thr Asp Ile
            500             505             510

Asn Ser Gly Ile Pro Gly Ile Asp Glu Val Met Lys Thr Thr Lys Ile
        515             520             525

Ile Ile Gly Cys Phe Val Ala Ile Thr Leu Met Ala Ala Val Met Leu
        530             535             540

Val Ile Phe Tyr Lys Met Arg Lys Gln His His Arg Gln Asn His His
545             550             555             560

Ala Pro Thr Arg Thr Val Glu Ile Ile Asn Val Asp Asp Glu Ile Thr
                565             570             575

Gly Asp Thr Pro Met Glu Ser His Leu Pro Met Pro Ala Ile Glu His
            580             585             590

Glu His Leu Asn His Tyr Asn Ser Tyr Lys Ser Pro Phe Asn His Thr
            595             600             605

Thr Thr Val Asn Thr Ile Asn Ser Ile His Ser Ser Val His Glu Pro
        610             615             620

Leu Leu Ile Arg Met Asn Ser Lys Asp Asn Val Gln Glu Thr Gln Ile
625             630             635             640
```

<210> SEQ ID NO 14
<211> LENGTH: 8
<212> TYPE: PRT
<213> ORGANISM: artificial sequence
<220> FEATURE:
<223> OTHER INFORMATION: NetG1 polypeptide

<400> SEQUENCE: 14

```
Asn Pro Tyr Met Cys Asn Asn Glu
1               5
```

<210> SEQ ID NO 15
<211> LENGTH: 8
<212> TYPE: PRT
<213> ORGANISM: artificial sequence
<220> FEATURE:
<223> OTHER INFORMATION: NetG1 polypeptide

<400> SEQUENCE: 15

```
Asn Pro Thr Met Cys Asn Asn Glu
1               5
```

<210> SEQ ID NO 16
<211> LENGTH: 14
<212> TYPE: PRT
<213> ORGANISM: artificial sequence
<220> FEATURE:
<223> OTHER INFORMATION: NetG1 polypeptide

<400> SEQUENCE: 16

```
Thr Phe Ser Ala Met Gly Asn Pro Tyr Met Cys Asn Asn Glu
1               5               10
```

<210> SEQ ID NO 17
<211> LENGTH: 14
<212> TYPE: PRT
<213> ORGANISM: artificial sequence
<220> FEATURE:
<223> OTHER INFORMATION: NetG1 polypeptide -continued

```
<400> SEQUENCE: 17

Thr Phe Cys Ala Met Gly Asn Pro Tyr Met Ser Asn Asn Glu
1               5                   10

<210> SEQ ID NO 18
<211> LENGTH: 14
<212> TYPE: PRT
<213> ORGANISM: artificial sequence
<220> FEATURE:
<223> OTHER INFORMATION: NetG1 polypeptide

<400> SEQUENCE: 18

Thr Phe Ser Ala Met Gly Asn Pro Tyr Met Ser Asn Asn Glu
1               5                   10

<210> SEQ ID NO 19
<211> LENGTH: 9
<212> TYPE: PRT
<213> ORGANISM: artificial sequence
<220> FEATURE:
<223> OTHER INFORMATION: NetG1 polypeptide

<400> SEQUENCE: 19

Gly Asn Pro Tyr Met Ser Asn Asn Glu
1               5

<210> SEQ ID NO 20
<211> LENGTH: 12
<212> TYPE: PRT
<213> ORGANISM: artificial sequence
<220> FEATURE:
<223> OTHER INFORMATION: NetG1 polypeptide

<400> SEQUENCE: 20

Ala Thr Asp Ser Leu Asp Ala Phe His Met Asp Pro
1               5                   10

<210> SEQ ID NO 21
<211> LENGTH: 9
<212> TYPE: PRT
<213> ORGANISM: artificial sequence
<220> FEATURE:
<223> OTHER INFORMATION: NetG1 polypeptide

<400> SEQUENCE: 21

Ala Thr Asp Ser Leu Asp Ala Phe His
1               5

<210> SEQ ID NO 22
<211> LENGTH: 14
<212> TYPE: PRT
<213> ORGANISM: artificial sequence
<220> FEATURE:
<223> OTHER INFORMATION: NetG1 polypeptide

<400> SEQUENCE: 22

Thr Phe Ser Ala Met Gly Asn Pro Thr Met Cys Asn Asn Glu
1               5                   10

<210> SEQ ID NO 23
<211> LENGTH: 14
<212> TYPE: PRT
<213> ORGANISM: artificial sequence
<220> FEATURE:
<223> OTHER INFORMATION: NetG1 polypeptide
```

```
<400> SEQUENCE: 23

Thr Phe Cys Ala Met Gly Asn Pro Thr Met Ser Asn Asn Glu
1               5                   10

<210> SEQ ID NO 24
<211> LENGTH: 14
<212> TYPE: PRT
<213> ORGANISM: artificial sequence
<220> FEATURE:
<223> OTHER INFORMATION: NetG1 polypeptide

<400> SEQUENCE: 24

Thr Phe Ser Ala Met Gly Asn Pro Thr Met Ser Asn Asn Glu
1               5                   10

<210> SEQ ID NO 25
<211> LENGTH: 9
<212> TYPE: PRT
<213> ORGANISM: artificial sequence
<220> FEATURE:
<223> OTHER INFORMATION: NetG1 polypeptide

<400> SEQUENCE: 25

Gly Asn Pro Thr Met Ser Asn Asn Glu
1               5

<210> SEQ ID NO 26
<211> LENGTH: 8
<212> TYPE: PRT
<213> ORGANISM: artificial sequence
<220> FEATURE:
<223> OTHER INFORMATION: NetG1 polypeptide

<400> SEQUENCE: 26

Asn Pro Tyr Met Ser Asn Asn Glu
1               5

<210> SEQ ID NO 27
<211> LENGTH: 8
<212> TYPE: PRT
<213> ORGANISM: artificial sequence
<220> FEATURE:
<223> OTHER INFORMATION: NetG1 polypeptide

<400> SEQUENCE: 27

Asn Pro Thr Met Ser Asn Asn Glu
1               5

<210> SEQ ID NO 28
<211> LENGTH: 14
<212> TYPE: PRT
<213> ORGANISM: artificial sequence
<220> FEATURE:
<223> OTHER INFORMATION: NetG1 polypeptide

<400> SEQUENCE: 28

Val Ser Ser Cys Ser Asn Gln Phe Ser Lys Val Ile Cys Val
1               5                   10

<210> SEQ ID NO 29
<211> LENGTH: 14
<212> TYPE: PRT
<213> ORGANISM: artificial sequence
<220> FEATURE:
<223> OTHER INFORMATION: NetG1 polypeptide

<400> SEQUENCE: 29
```

-continued

Val Cys Ser Ser Ser Asn Gln Phe Ser Lys Val Ile Cys Val
1               5                   10

<210> SEQ ID NO 30
<211> LENGTH: 14
<212> TYPE: PRT
<213> ORGANISM: artificial sequence
<220> FEATURE:
<223> OTHER INFORMATION: NetG1 polypeptide

<400> SEQUENCE: 30

Val Cys Ser Cys Ser Asn Gln Phe Ser Lys Val Ile Ser Val
1               5                   10

<210> SEQ ID NO 31
<211> LENGTH: 14
<212> TYPE: PRT
<213> ORGANISM: artificial sequence
<220> FEATURE:
<223> OTHER INFORMATION: NetG1 polypeptide

<400> SEQUENCE: 31

Val Ser Ser Ser Ser Asn Gln Phe Ser Lys Val Ile Cys Val
1               5                   10

<210> SEQ ID NO 32
<211> LENGTH: 14
<212> TYPE: PRT
<213> ORGANISM: artificial sequence
<220> FEATURE:
<223> OTHER INFORMATION: NetG1 polypeptide

<400> SEQUENCE: 32

Val Ser Ser Cys Ser Asn Gln Phe Ser Lys Val Ile Ser Val
1               5                   10

<210> SEQ ID NO 33
<211> LENGTH: 14
<212> TYPE: PRT
<213> ORGANISM: artificial sequence
<220> FEATURE:
<223> OTHER INFORMATION: NetG1 polypeptide

<400> SEQUENCE: 33

Val Cys Ser Ser Ser Asn Gln Phe Ser Lys Val Ile Ser Val
1               5                   10

<210> SEQ ID NO 34
<211> LENGTH: 14
<212> TYPE: PRT
<213> ORGANISM: artificial sequence
<220> FEATURE:
<223> OTHER INFORMATION: NetG1 polypeptide

<400> SEQUENCE: 34

Val Ser Ser Ser Ser Asn Gln Phe Ser Lys Val Ile Ser Val
1               5                   10

<210> SEQ ID NO 35
<211> LENGTH: 7
<212> TYPE: PRT
<213> ORGANISM: artificial sequence
<220> FEATURE:
<223> OTHER INFORMATION: functional assay peptide

<400> SEQUENCE: 35

-continued

```
Asn Pro Tyr Met Ser Asn Asn
1               5

<210> SEQ ID NO 36
<211> LENGTH: 7
<212> TYPE: PRT
<213> ORGANISM: artificial sequence
<220> FEATURE:
<223> OTHER INFORMATION: functional assay peptide

<400> SEQUENCE: 36

Asn Pro Thr Met Ser Asn Asn
1               5
```

NETRIN G1 POLYPEPTIDES

REFERENCE TO SEQUENCE LISTING

This application includes a Sequence Listing filed electronically as a text file named 185300-08401US-SEQ, created on Apr. 23, 2020, with a size of 17,862 bytes. The Sequence Listing is incorporated herein by reference.

FIELD

The present disclosure relates generally to the field of cancer treatments. More particularly, the present disclosure relates to polypeptides of netrin G1 (NetG1) and its cell surface receptor netrin G1 ligand (NGL1), and antibodies thereto. The present disclosure also relates to use of NetG1 and/or NGL1 polypeptides, and/or antibodies specific to these polypeptides, in methods of treating cancers and diseases, including chronic fibrosis and inflammation.

BACKGROUND

Pancreatic cancer is projected to become the second leading cause of cancer related deaths by 2030, due to its abysmal 5 year survival rate. The most common form of pancreatic cancer is pancreatic ductal adenocarcinoma (PDAC), to which treatments are often refractory, and where symptoms only appear in advanced stages of the disease, making few patients eligible for surgical interventions. Therefore, there is an urgent need to develop new diagnostic and better therapeutic approaches.

Tumors are not entirely made out of cancerous cells. They contain many other components, referred to as tumor stroma, that may either encourage or hinder the tumor's growth. Tumor stroma includes non-cancerous cells and a framework of fibrous sugary proteins, called the extracellular matrix, which surround and signal to cells while providing physical support. Moreover, sometimes the stroma of these pancreatic tumors can protect the cancer cells from the host's immune system as well as from anti-cancer drugs.

PDAC stroma represents a unique microenvironment that consists of a fibrous expansion reaction known as desmoplasia, characterized by the deposition of an abundant extracellular matrix (ECM) by cancer associated fibroblasts (CAFs). Desmoplastic stroma plays a role in epithelial tumor development and progression such as, for example, in pancreatic or renal epithelial tissue. The exact contribution of the mesenchymal stroma for the development of a pro-tumorigenic role for desmoplasia is not clear. Nonetheless, homeostatic normal or innate mesenchymal stroma is believed to provide a natural tumor suppressive microenvironment. Evidence has emerged that desmoplastic ablation is detrimental to patients. Other evidence indicates that reprograming mesenchymal stroma back to its restrictive innate state seems to bear therapeutic promise, including reinstituting anti-tumoral immune activity. Thus, desmoplasia has potential implications for tumor therapy. There remains a need in the art to be able to manipulate desmoplastic stroma, toward improving the understanding of the underlying biology behind stromal activation.

Netrin G1 (NetG1, transcribed by the NTNG1 gene) is a plasma membrane protein containing eukaryotic growth factor (EGF)-like domains. This protein acts to guide axon growth during neuronal development and is involved in controlling patterning and neuronal circuit formation at the laminar, cellular, subcellular and synaptic levels. Promotes neurite outgrowth of both axons and dendrites. The protein may be processed into a secreted form.

Netrin G1 ligand (NGL1), also known as Leucine Rich Repeat Containing 4C (LRRC4C)) is a specific binding partner for netrin G1. NGL1 is mainly localized to the postsynaptic side of excitatory synapses, and interacts with the presynaptic ligands, netrin-G1. These interactions are thought to couple synaptic adhesion events to the assembly of synaptic proteins. Consistent with these functions, defects in NetG1 and NGL1 are associated with impaired learning and memory, hyperactivity, and an abnormal acoustic startle response in transgenic mice, and schizophrenia, bipolar disorder, and Rett syndrome in human patients.

SUMMARY

The present disclosure provides isolated Netrin G1 (NetG1) polypeptides and Netrin G1 ligand (NGL-1) polypeptides comprising up to 20 amino acids, wherein: the NetG1 polypeptide comprises: TFCAMGNPYMCNNE (SEQ ID NO:1), TFSAMGNPYMCNNE (SEQ ID NO:16), TFCAMGNPYMSNNE (SEQ ID NO:17), TFSAMGNPYMSNNE (SEQ ID NO:18), GNPYM CNNE (SEQ ID NO:2), GNPYMSNNE (SEQ ID NO:19), AVGE-IFVDELHLARYF (SEQ ID NO: 3), VGEIFV (SEQ ID NO:4), EYSTGYTTNSK (SEQ ID NO:5), STGYTT (SEQ ID NO:6), ATDCLDAFHMDP (SEQ ID NO:7), ATD-SLDAFHMDP (SEQ ID NO:20), ATDCLDAFH (SEQ ID NO:8), ATDSLDAFH (SEQ ID NO:21), TFCAMGNPTMCNNE (SEQ ID NO:9), TFSAMGNPTMCNNE (SEQ ID NO:22), TFCAMGNPTMSNNE (SEQ ID NO:23), TFSAMGNPTMSNNE (SEQ ID NO:24), GNPTMCNNE (SEQ ID NO:10), GNPTMSNNE (SEQ ID NO:25), NPYMCNNE (SEQ ID NO:14), NPYMSNNE (SEQ ID NO:26), NPTMCNNE (SEQ ID NO:15); or NPTMSNNE (SEQ ID NO:27); the NGL-1 polypeptide comprises VCSCSNQFSKVICV (SEQ ID NO:11), VSS-CSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSS-CSNQFSKVISV (SEQ ID NO:32), VCSSSNQFSKVISV (SEQ ID NO:33), or VSSSSNQFSKVISV (SEQ ID NO:34); and wherein the NetG1 polypeptide or NGL-1 polypeptide further comprises zero, one, two, three, or four conservative amino acid substitutions.

The present disclosure also provides methods of treating a human having a cancer or a cancer associated with chronic fibrosis and/or chronic inflammation comprising administering to the human in need thereof a NetG1 polypeptide or NGL-1 polypeptide comprising up to 20 amino acids, wherein: the NetG1 polypeptide comprises: TFCAMGNPYMCNNE (SEQ ID NO: 1), TFSAMGNPYMCNNE (SEQ ID NO:16), TFCAMGNPYMSNNE (SEQ ID NO:17), TFSAMGNPYMSNNE (SEQ ID NO:18), GNPYMCNNE (SEQ ID NO:2), GNPYMSNNE (SEQ ID NO:19), AVGE-IFVDELHLARYF (SEQ ID NO:3), VGEIFV (SEQ ID NO:4), EYSTGYTTNSK (SEQ ID NO:5), STGYTT (SEQ ID NO:6), ATDCLDAFHMDP (SEQ ID NO: 7), ATD-SLDAFHMDP (SEQ ID NO:20), ATDCLDAFH (SEQ ID NO:8), ATDSLDAFH (SEQ ID NO:21), TFCAMGNPTMCNNE (SEQ ID NO:9), TFSAMGNPTMCNNE (SEQ ID NO: 22), TFCAMGNPTMSNNE (SEQ ID NO:23), TFSAMGNPTMSNNE (SEQ ID NO:24), GNPTMCNNE (SEQ ID NO: 10), GNPTMSNNE (SEQ ID NO:25), NPYMCNNE (SEQ ID NO: 14), NPYMSNNE (SEQ ID NO:26), NPTMCNNE (SEQ ID NO: 15); or NPTMSNNE (SEQ ID NO: 27); the NGL-1 polypeptide comprises VCSCSNQFSKVICV (SEQ ID NO:11), VSS-CSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSS-CSNQFSKVISV (SEQ ID NO:32), VCSSSNQFSKVISV (SEQ ID NO:33), or VSSSSNQFSKVISV (SEQ ID NO:34); and wherein the NetG1 polypeptide or NGL-1 polypeptide further comprises zero, one, two, three, or four conservative amino acid substitutions.

The present disclosure also provides methods of inducing a biological process in a human cell comprising administering to the human cell a NetG1 polypeptide or NGL-1 polypeptide comprising up to 20 amino acids, wherein: the NetG1 polypeptide comprises: TFCAMGNPYMCNNE (SEQ ID NO:1), TFSAMGNPYMCNNE (SEQ ID NO:16), TFCAMGNPYMSNNE (SEQ ID NO:17), TFSAMGNPYMSNNE (SEQ ID NO:18), GNPYMCNNE (SEQ ID NO:2), GNPYMSNNE (SEQ ID NO: 19), AVGE-IFVDELHLARYF (SEQ ID NO:3), VGEIFV (SEQ ID NO:4), EYSTGYTTNSK (SEQ ID NO:5), STGYTT (SEQ ID NO: 6), ATDCLDAFHMDP (SEQ ID NO:7), ATD-SLDAFHMDP (SEQ ID NO:20), ATDCLDAFH (SEQ ID NO:8), ATDSLDAFH (SEQ ID NO:21), TFCAMGNPTMCNNE (SEQ ID NO: 9), TFSAMGNPTMCNNE (SEQ ID NO:22), TFCAMGNPTMSNNE (SEQ ID NO:23), TFSAMG NPTMSNNE (SEQ ID NO:24), GNPTMCNNE (SEQ ID NO: 10), GNPTMSNNE (SEQ ID NO:25), NPYMCNNE (SEQ ID NO:14), NPYMSNNE (SEQ ID NO:26), NPTMCNNE (SEQ ID NO:15); or NPTMSNNE (SEQ ID NO:27); the NGL-1 polypeptide comprises VCSCSNQFSKVICV (SEQ ID NO:11), VSS-CSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSS-CSNQFSKVISV (SEQ ID NO:32), VCSSSNQFSKVISV (SEQ ID NO:33), or VSSSSNQFSKVISV (SEQ ID NO:34); and wherein the NetG1 polypeptide or NGL-1 polypeptide further comprises zero, one, two, three, or four conservative amino acid substitutions; wherein the biological process induced is: inhibiting NetG1 interaction with NGL1; inhibiting NGL1 engagement with NetG1; inhibiting rescue of starvation-induced death of a cancer cell; inhibiting activation of immunosuppressive cells; preventing inhibition of immunogenic cells; altering extracellular matrix production; altering amino acid secretion; altering metabolism of glutamate or glutamine dependent products; preventing immunosuppressive cells from maintaining pro-tumorigenic cells; preventing secretion of immunosuppressive factors; and/or preventing communication between any one or more of neural cells, fibroblastic cells, immune cells, and tumor cells.

The present disclosure also provides isolated antibodies, or an antigen-binding fragments thereof, that bind to a Netrin G1 (NetG1) polypeptide or Netrin G1 ligand (NGL-1) polypeptide comprising up to 20 amino acids, wherein: the NetG1 polypeptide comprises: TFCAMGNPYMCNNE (SEQ ID NO:1), TFSAMGNPYMCNNE (SEQ ID NO: 16), TFCAMGNPYMSNNE (SEQ ID NO:17), TFSAMGNPYMSNNE (SEQ ID NO:18), GNPYMCNNE (SEQ ID NO:2), GNPYMSNNE (SEQ ID NO:19), AVGE-IFVDELHLARYF (SEQ ID NO:3), VGEIFV (SEQ ID NO:4), EYSTGYTTNSK (SEQ ID NO:5), STGYTT (SEQ ID NO: 6), ATDCLDAFHMDP (SEQ ID NO:7), ATD- SLDAFHMDP (SEQ ID NO:20), ATDCLDAFH (SEQ ID NO:8), ATDSLDAFH (SEQ ID NO:21), TFCAMGNPTMCNNE (SEQ ID NO: 9), TFSAMGNPTMCNNE (SEQ ID NO:22), TFCAMGNPTMSNNE (SEQ ID NO:23), TFSAMG NPTMSNNE (SEQ ID NO:24), GNPTMCNNE (SEQ ID NO: 10), GNPTMSNNE (SEQ ID NO:25), NPYMCNNE (SEQ ID NO:14), NPYMSNNE (SEQ ID NO:26), NPTMCNNE (SEQ ID NO:15); or NPTMSNNE (SEQ ID NO:27); the NGL-1 polypeptide comprises VCSCSNQFSKVICV (SEQ ID NO:11), VSS-CSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSS-CSNQFSKVISV (SEQ ID NO:32), VCSSSNQFSKVISV (SEQ ID NO:33), or VSSSSNQFSKVISV (SEQ ID NO:34); and wherein the NetG1 polypeptide or NGL-1 polypeptide further comprises zero, one, two, three, or four conservative amino acid substitutions.

The present disclosure also provides methods of making an antibody that binds to a Netrin G1 (NetG1) polypeptide or Netrin G1 ligand (NGL-1) polypeptide, comprising: immunizing an animal with a NetG1 polypeptide or NGL-1 polypeptide comprising up to 20 amino acids, wherein: the NetG1 polypeptide comprises: TFCAMGNPYMCNNE (SEQ ID NO: 1), TFSAMGNPYMCNNE (SEQ ID NO:16), TFCAMGNPYMSNNE (SEQ ID NO:17), TFSAMGNPYMSNNE (SEQ ID NO:18), GNPYMCNNE (SEQ ID NO:2), GNPYMSNNE (SEQ ID NO:19), AVGE-IFVDELHLARYF (SEQ ID NO:3), VGEIFV (SEQ ID NO:4), EYSTGYTTNSK (SEQ ID NO:5), STGYTT (SEQ ID NO:6), ATDCLDAFHMDP (SEQ ID NO: 7), ATD-SLDAFHMDP (SEQ ID NO:20), ATDCLDAFH (SEQ ID NO:8), ATDSLDAFH (SEQ ID NO:21), TFCAMGNPTMCNNE (SEQ ID NO:9), TFSAMGNPTMCNNE (SEQ ID NO: 22), TFCAMGNPTMSNNE (SEQ ID NO:23), TFSAMGNPTMSNNE (SEQ ID NO:24), GNPTMCNNE (SEQ ID NO:10), GNPTMSNNE (SEQ ID NO:25), NPYMCNNE (SEQ ID NO: 14), NPYMSNNE (SEQ ID NO:26), NPTMCNNE (SEQ ID NO: 15); or NPTMSNNE (SEQ ID NO: 27); the NGL-1 polypeptide comprises VCSCSNQFSKVICV (SEQ ID NO:11), VSS-CSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSS-CSNQFSKVISV (SEQ ID NO:32), VCSSSNQFSKVISV (SEQ ID NO:33), or VSSSSNQFSKVISV (SEQ ID NO:34); and wherein the NetG1 polypeptide or NGL-1 polypeptide further comprises zero, one, two, three, or four conservative amino acid substitutions.

The present disclosure also provides methods of treating a human having a cancer or a cancer associated with chronic fibrosis and/or chronic inflammation comprising administering to the human in need thereof an antibody, or antigen-binding fragment thereof, that binds to a Netrin G1 (NetG1) polypeptide or Netrin G1 ligand (NGL-1) polypeptide comprising up to 20 amino acids, wherein: the NetG1 polypeptide comprises: TFCAMGNPYMCNNE (SEQ ID NO: 1), TFSAMGNPYMCNNE (SEQ ID NO:16), TFCAMGNPYMSNNE (SEQ ID NO:17), TFSAMGNPYMSNNE (SEQ ID NO: 18), GNPYMCNNE (SEQ ID NO:2), GNPYMSNNE (SEQ ID NO:19), AVGE-IFVDELHLARYF (SEQ ID NO:3), VGEIFV (SEQ ID NO:4), EYSTGYTTNSK (SEQ ID NO:5), STGYTT (SEQ ID NO:6), ATDCLDAFHMDP (SEQ ID NO: 7), ATD-SLDAFHMDP (SEQ ID NO:20), ATDCLDAFH (SEQ ID NO:8), ATDSLDAFH (SEQ ID NO:21), TFCAMGNPTMCNNE (SEQ ID NO:9), TFSAMGNPTMCNNE (SEQ ID NO: 22), TFCAMGNPTMSNNE (SEQ ID NO:23), TFSAMGNPTMSNNE (SEQ ID NO:24), GNPTMCNNE (SEQ ID NO:10), GNPTMSNNE (SEQ ID NO:25), NPYMCNNE (SEQ ID NO: 14), NPYMSNNE (SEQ ID NO:26), NPTMCNNE (SEQ ID NO: 15); or NPTMSNNE (SEQ ID NO: 27); the NGL-1 polypeptide comprises VCSCSNQFSKVICV (SEQ ID NO:11), VSS-CSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSS-CSNQFSKVISV (SEQ ID NO:32), VCSSSNQFSKVISV (SEQ ID NO:33), or VSSSSNQFSKVISV (SEQ ID NO:34); and wherein the NetG1 polypeptide or NGL-1 polypeptide further comprises zero, one, two, three, or four conservative amino acid substitutions.

The present disclosure also provides methods of inducing a biological process in a human cell comprising administering to the human cell an antibody, or antigen-binding fragment thereof, that binds to a Netrin G1 (NetG1) polypeptide or Netrin G1 ligand (NGL-1) polypeptide comprising up to 20 amino acids, wherein: the NetG1 polypeptide comprises: TFCAMGNPYMCNNE (SEQ ID NO:1), TFSAMGNPYMCNNE (SEQ ID NO:16), TFCAMGNPYMSNNE (SEQ ID NO: 17), TFSAMGNPYMSNNE (SEQ ID NO:18), GNPYMCNNE (SEQ ID NO:2), GNPYMSNNE (SEQ ID NO:19), AVGE-IFVDELHLARYF (SEQ ID NO:3), VGEIFV (SEQ ID NO:4), EYSTGYTTNSK (SEQ ID NO:5), STGYTT (SEQ ID NO: 6), ATDCLDAFHMDP (SEQ ID NO:7), ATD-SLDAFHMDP (SEQ ID NO:20), ATDCLDAFH (SEQ ID NO:8), ATDSLDAFH (SEQ ID NO:21), TFCAMGNPTMCNNE (SEQ ID NO: 9), TFSAMGNPTMCNNE (SEQ ID NO:22), TFCAMGNPTMSNNE (SEQ ID NO:23), TFSAMGNPTMSNNE (SEQ ID NO:24), GNPTMCNNE (SEQ ID NO: 10), GNPTMSNNE (SEQ ID NO:25), NPYMCNNE (SEQ ID NO:14), NPYMSNNE (SEQ ID NO:26), NPTMCNNE (SEQ ID NO:15); or NPTMSNNE (SEQ ID NO:27); the NGL-1 polypeptide comprises VCSCSNQFSKVICV (SEQ ID NO:11), VSS-CSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSS-CSNQFSKVISV (SEQ ID NO:32), VCSSSNQFSKVISV (SEQ ID NO:33), or VSSSSNQFSKVISV (SEQ ID NO:34); and wherein the NetG1 polypeptide or NGL-1 polypeptide further comprises zero, one, two, three, or four conservative amino acid substitutions; wherein the biological process induced is: inhibiting NetG1 interaction with NGL1; inhibiting NGL1 engagement with NetG1; inhibiting rescue of starvation-induced death of a cancer cell; inhibiting activation of immunosuppressive cells; preventing inhibition of immunogenic cells; altering extracellular matrix production; altering amino acid secretion; altering metabolism of glutamate or glutamine dependent products; preventing immunosuppressive cells from maintaining pro-tumorigenic cells; preventing secretion of immunosuppressive factors; and/or preventing communication between any one or more of neural cells, fibroblastic cells, immune cells, and tumor cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2B shows increased rough surface/blebbing is.

7 ment of KRAS-transformed pancreatic cells improves the effectiveness of EVs harvested from NetG1 deficient CAFs (NG1$^{KO}$) in rescuing starvation-induced death of PDAC cancer cells (Panel B).

Figure 5A:
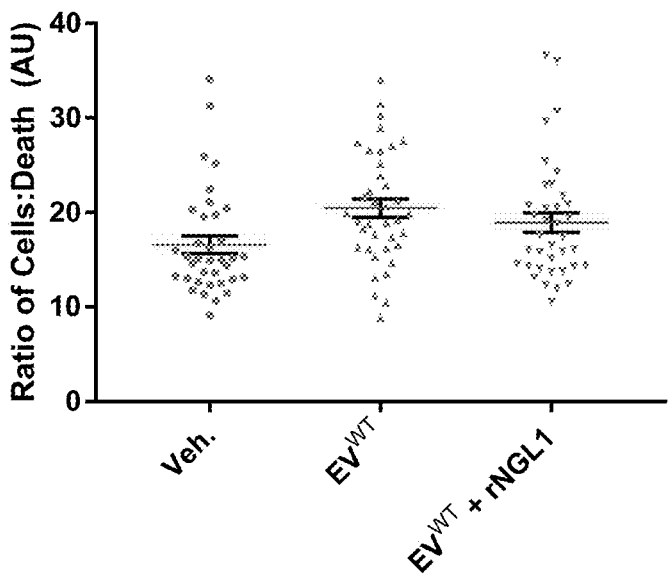
FIG. 5 shows the effectiveness of CAF-produced EVs in rescuing starvation-induced death of PDAC cancer cells tends to decrease when EVs are pre-incubated with recombinant NGL1 (Panel A), and the recombinant NetG1 treat-
Figure 5B:
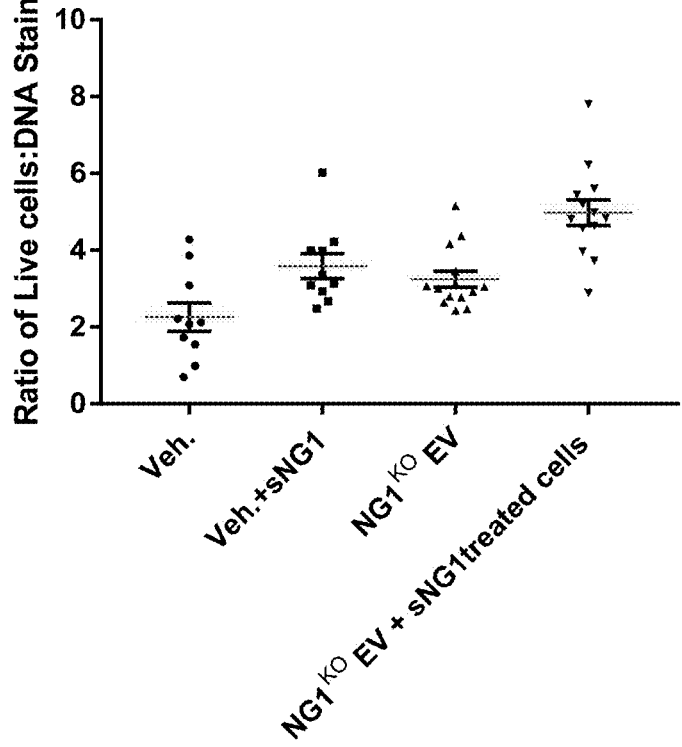

FIG. 5A shows the effectiveness of CAF-produced EVs in rescuing starvation-induced death of PDAC cancer cells tends to decrease when EVs are pre-incubated with recombinant NGL1. FIG. 5B shows the recombinant NetG1 treatment of KRAS-transformed pancreatic cells improves the effectiveness of EVs harvested from NetG1 deficient CAFs (NG1KO) in rescuing starvation-induced death of PDAC cancer cells.

Figure 6:
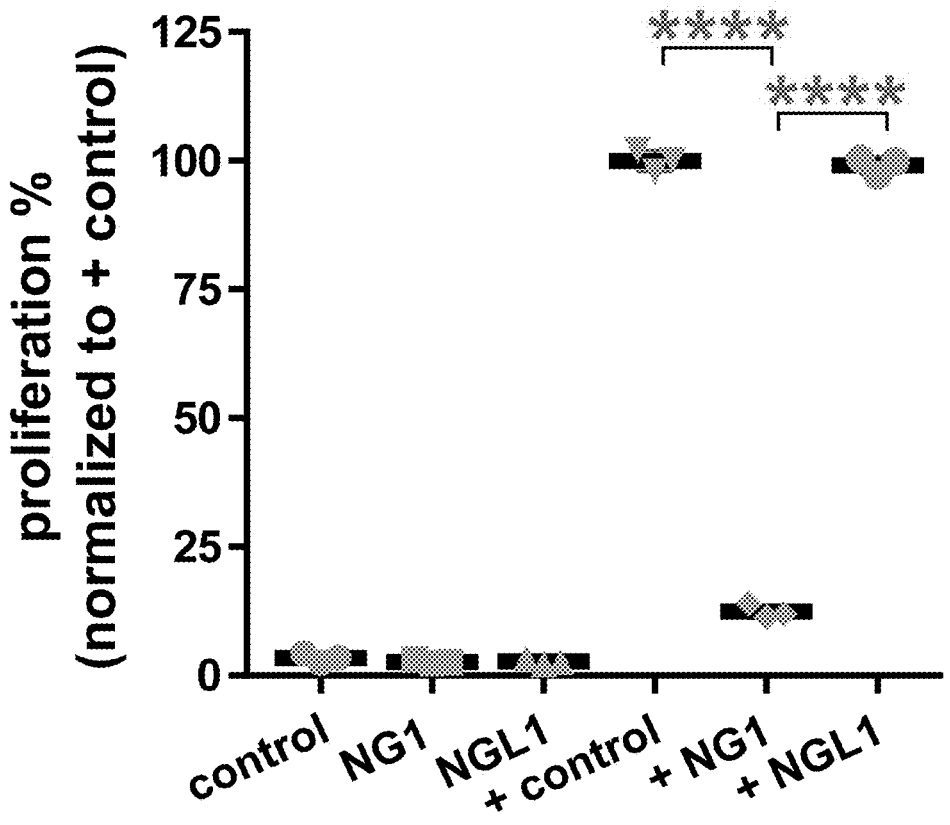

FIG. 6 shows that treatment of T-cells with recombinant NetG1 during activation prevents their polarization/activation.

Figure 7A:
Figure 7B:
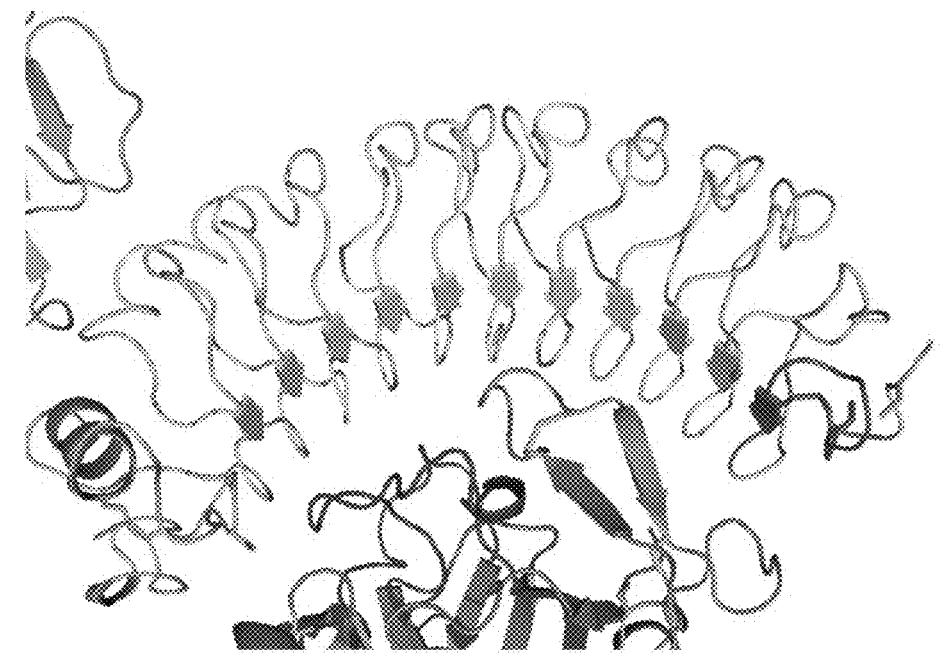

FIG. 7A shows NetG1 peptides: cyan, magenta, blue, and red domains correspond to the sequences used to generate the NetG1 peptides. Cyan residues 78-91, short version (in bold) residues 83-91, TFCAMGNPYMCNNE (SEQ ID NO:1; mutant will include T as opposed to Y86 and is not expected to be functional). There is not a disulfide in the crystal structure between residues 80 and 88; Cys88 has a poor dihedral angle and replacing it with a good rotamer puts it in exactly disulfide-bonding distance of Cys80. It does make a disulfide if the side-chain conformations are predicted using conformational software. Cys88 is not interacting with the receptor (NGL1), and could be replaced with serine (Ser/S rationale used to generate the peptides utilized in functional asays below: NPYMSNN (SEQ ID NO:35) and the mutant NPTMSNN (SEQ ID NO:36)) to both stabilize the sequence and avoid forming disulfides with NGL1 under oxidizing conditions. Magenta residues 270-285 (280-295 in PDB 3zyj), short version (bold) 271-276 AVGEIFVDELHLARYF (SEQ ID NO:3); red residues 209219 (219-229 in 3zyj), short version (bold) 211-216 EYSTGYTTNSK (SEQ ID NO:5); blue residues 179-190 (189-200 in 3zyj), short version (bold) 179-187 ATDCLDAFHMDP (SEQ ID NO:7). This is a short helix and FH residues do not interact with the receptor (NGL1) but are part of a helix; also, Cys182 can make a disulfide bond with Cys206; ATDSLDAFHMDP (SEQ ID NO:20)). FIG. 7B shows NGL1 peptides (also for functional peptide drugs and for antibody purposes). The N-terminal leucine-rich repeat (of NGL1) is a potential functional peptide/antigen. It has a disulfide bond which would hold the molecule together in something like the right folded structure (if the disulfide can be maintained while eliciting the antibody): VCSCSNQFSKVICV (SEQ ID NO: 11). The peptide is shown in magentain with the disulfide in sticks. The peptide will work as epitope for antibody production as well as for functional purposes (like in the case of NetG1 peptides), as well as a control.

Figure 8A:
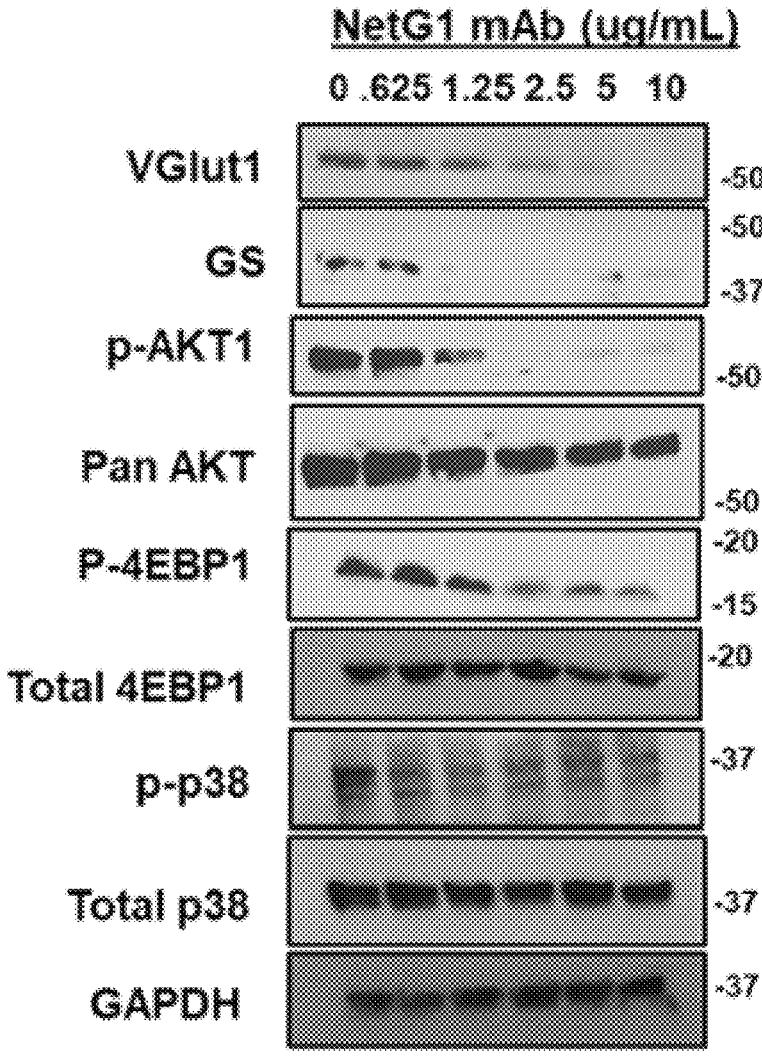
Figure 8B:
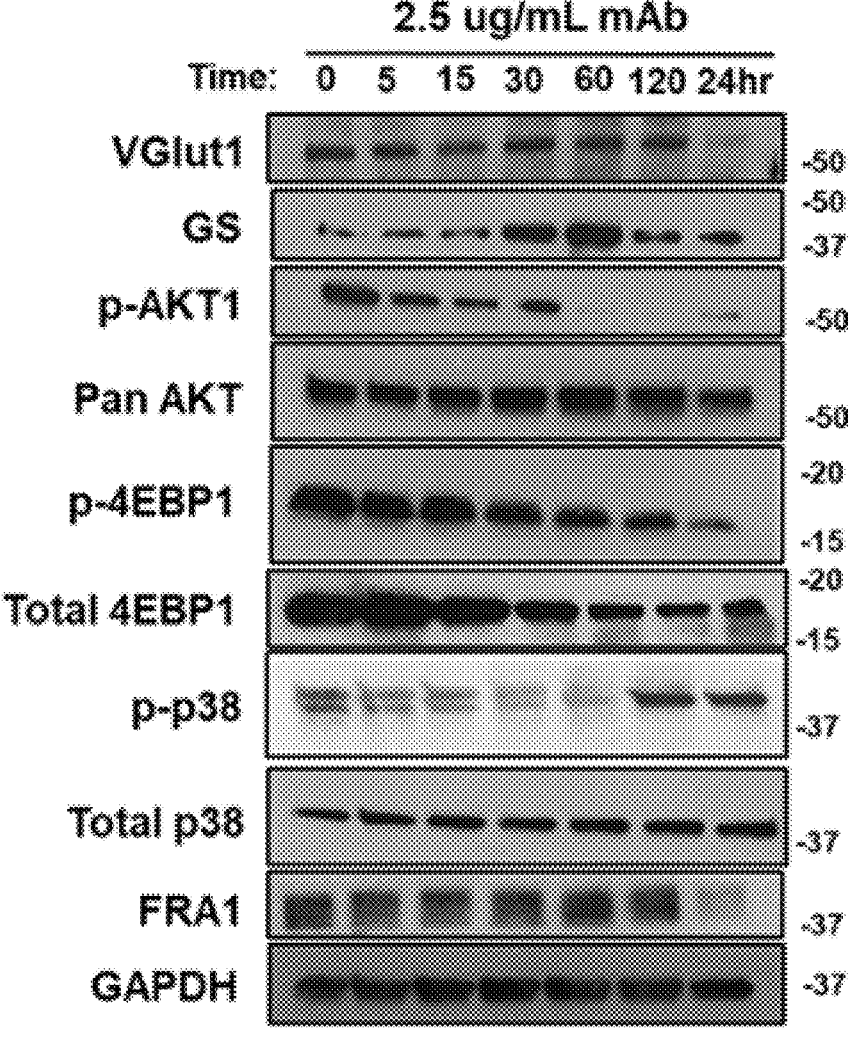
Figure 8C:
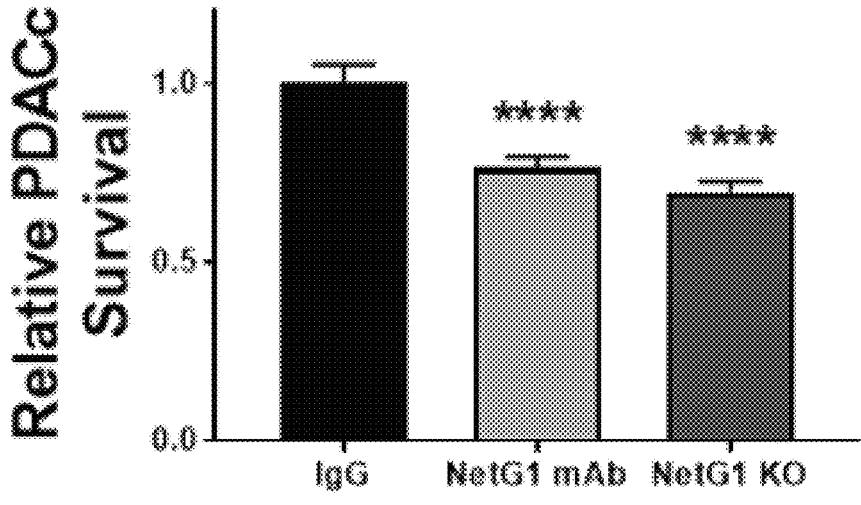
Figure 8D:
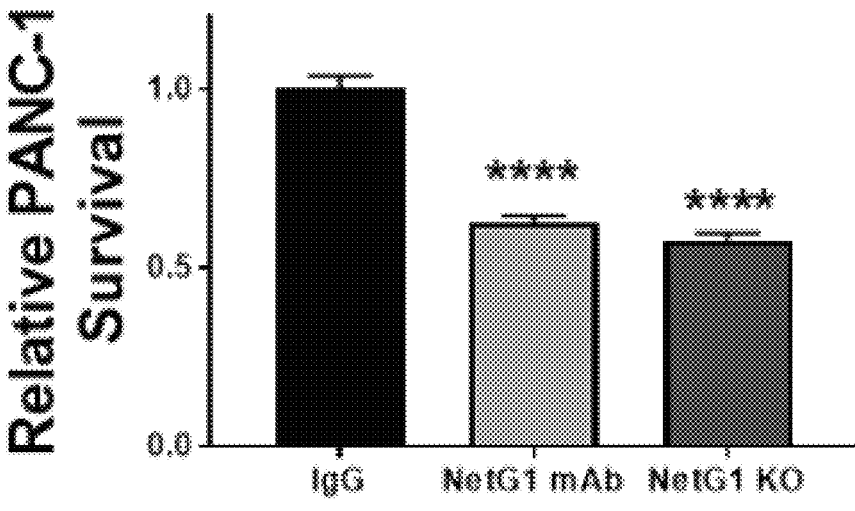
Figure 8E:
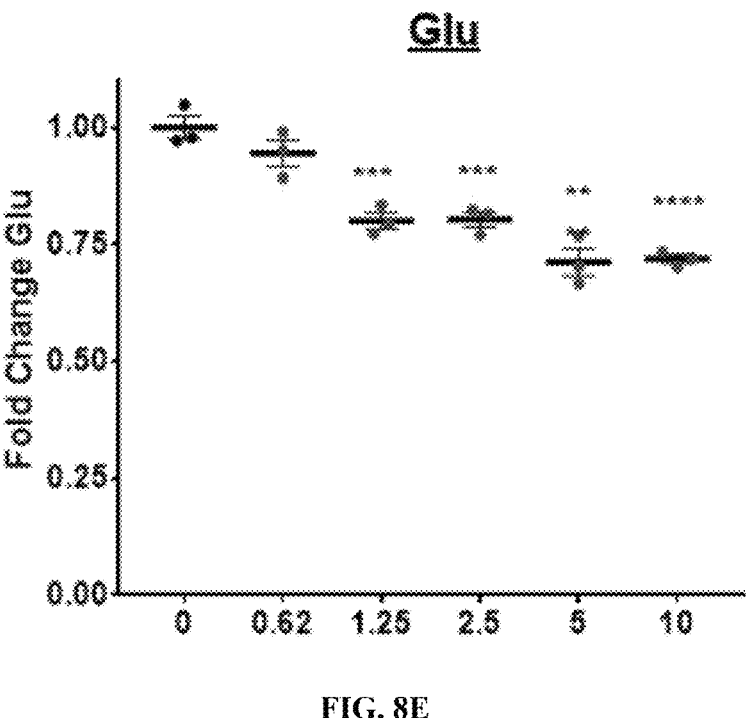
Figure 8F:
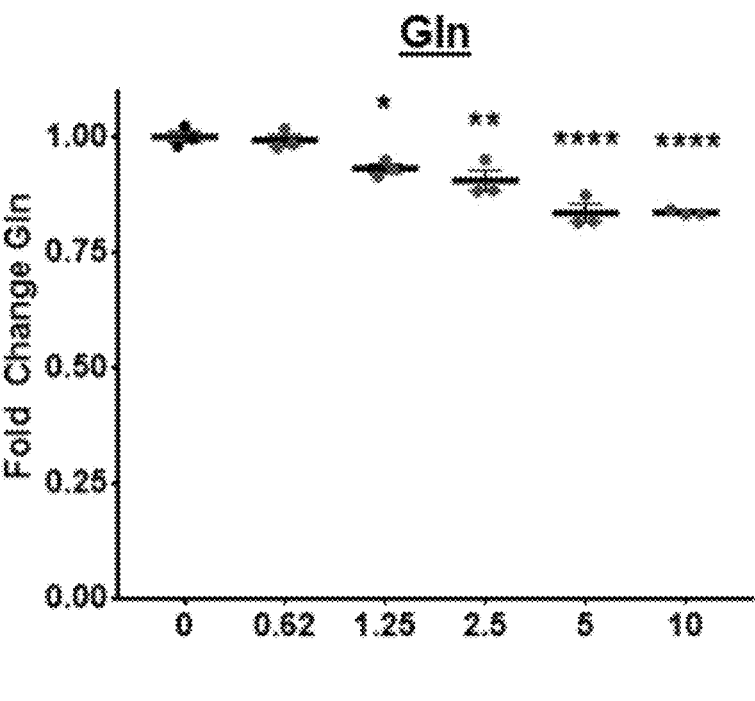
Figure 8G:
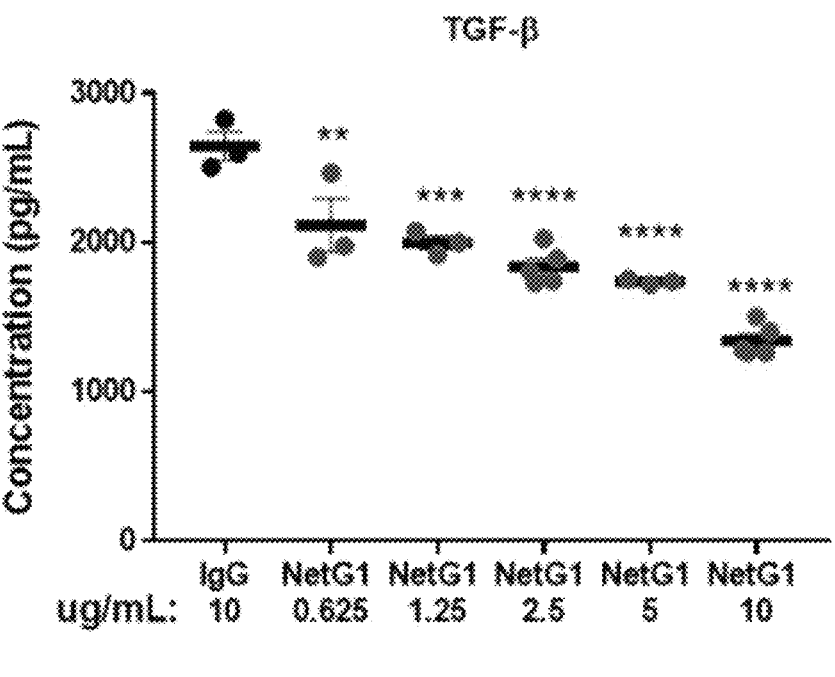
Figure 8H:
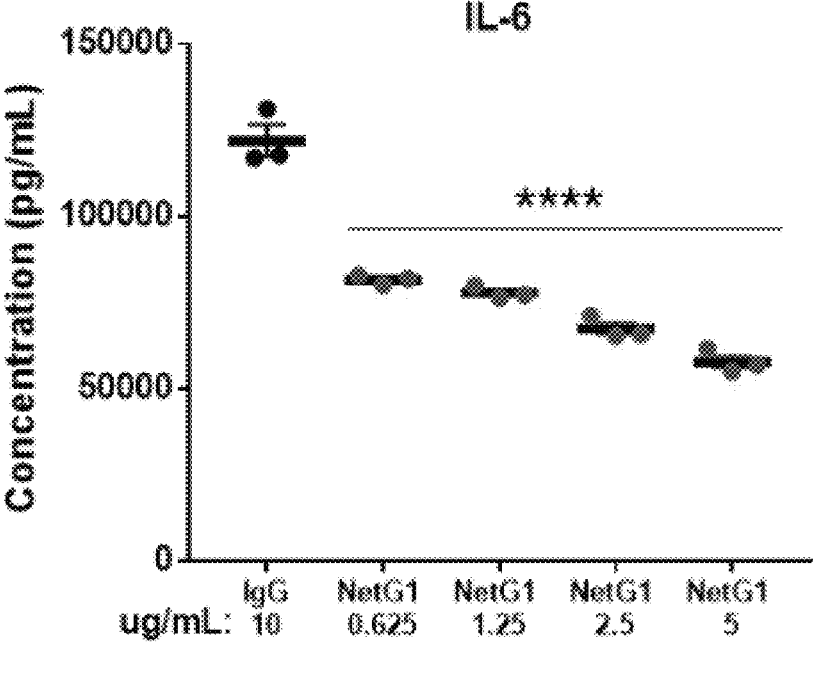
Figure 8I:
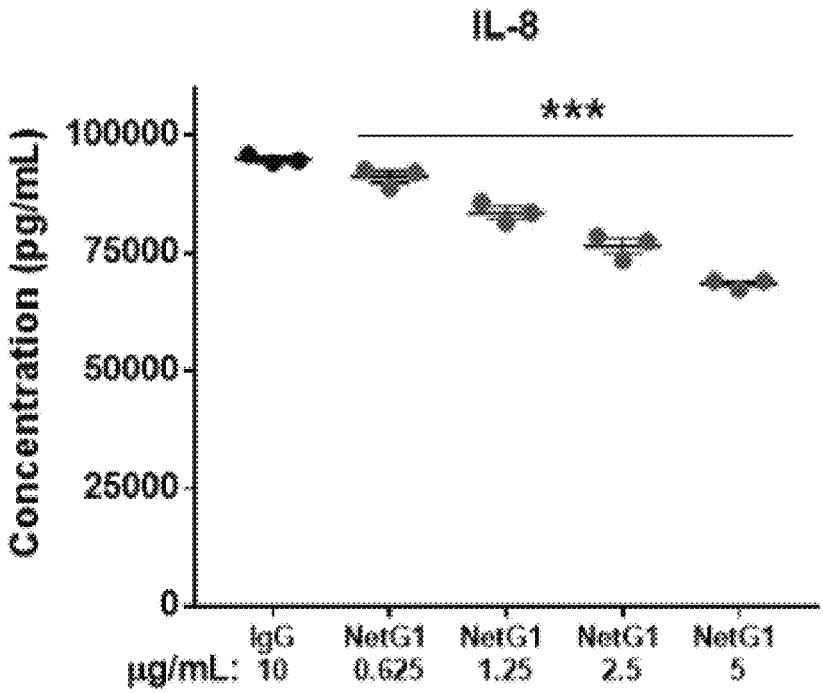

FIG. 8A shows that a neutralizing monoclonal antibody targeting NetG1 reduces pro-tumor properties of CAFs; a representative Western blot demonstrating a dose dependent decrease in proteins associated with pro-tumorigenic pathways in CAFs following anti-NetrinG1 monoclonal antibody from treatment. FIG. 8B shows a representative Western blot demonstrating a time dependent decrease in proteins associated with pro-tumorigenic pathways in CAFs following anti-NetrinG1 monoclonal antibody from treatment. FIG. 8C shows quantification of PDAC cell survival under serum and glutamine starvation after a 48 hour co-culture with CON or NetG1 KO CAFs. FIG. 8D shows graphs depicting amounts of secreted glutamate and glutamine detected in the conditioned media of CAFs treated with IgG or increasing doses of anti-NetG1 mAb. FIG. 8E shows graphs depicting amounts of secreted pro-tumor cytokines detected in the conditioned media of CAFs treated with IgG or increasing doses of anti-NetG1 mAb.

Figure 9D:
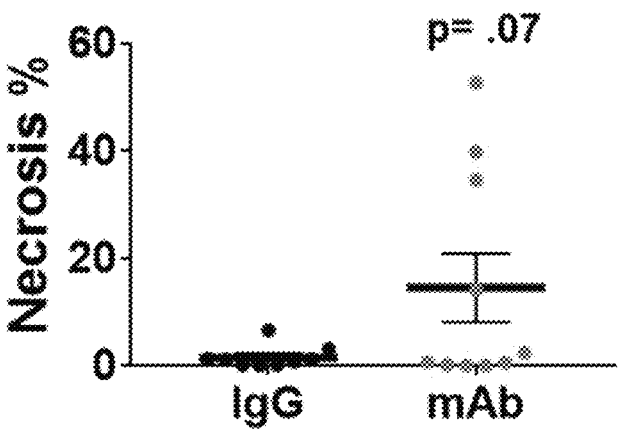
Figure 9E:
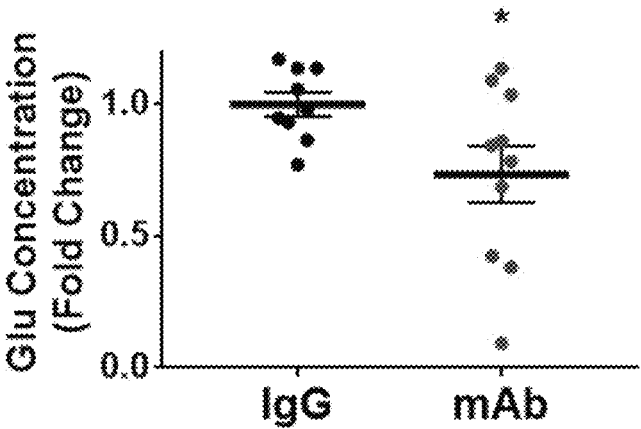
Figure 9F:
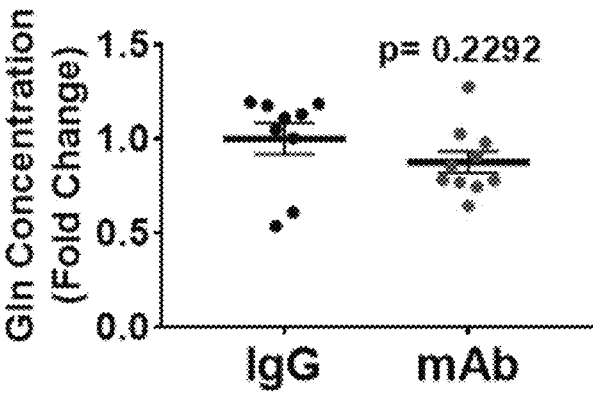

FIG. 9A a graph depicting relative tumor weights. FIG. 9B shows quantification of % area of the pancreas that was classified as tumor. FIG. 9C shows graphs depicting the relative weights of the pancreata isolated from the mice. FIG. 9D shows quantification of the % area of the pancreas that was classified as necrotic. FIG. 9E shows a graph depicting amounts of tumor secreted glutamate. FIG. 9F shows a graph depicting amounts of tumor secreted secreted glutamine.

Figure 10A:
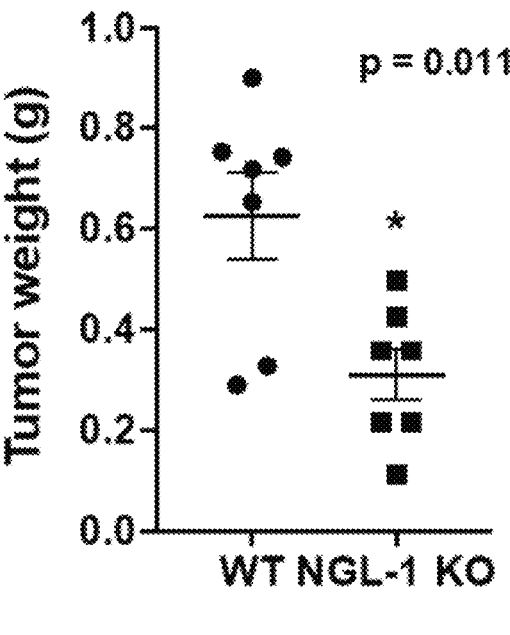
Figure 10B:
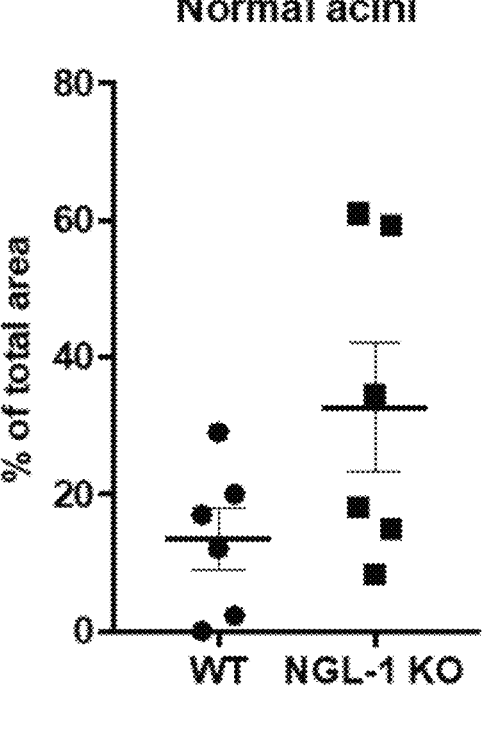
Figure 10C:
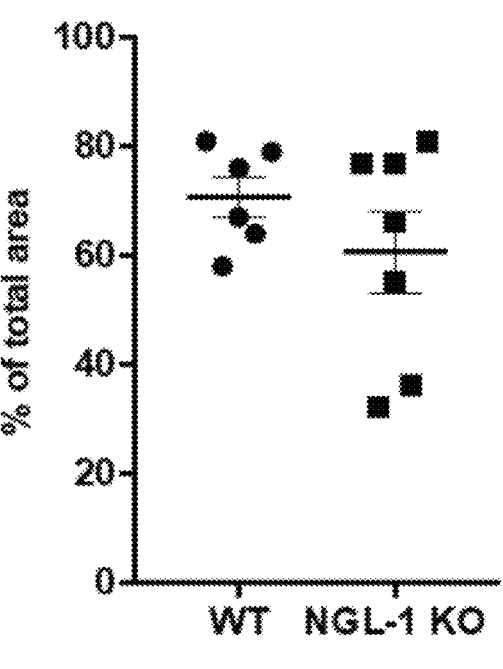
Figure 10D:
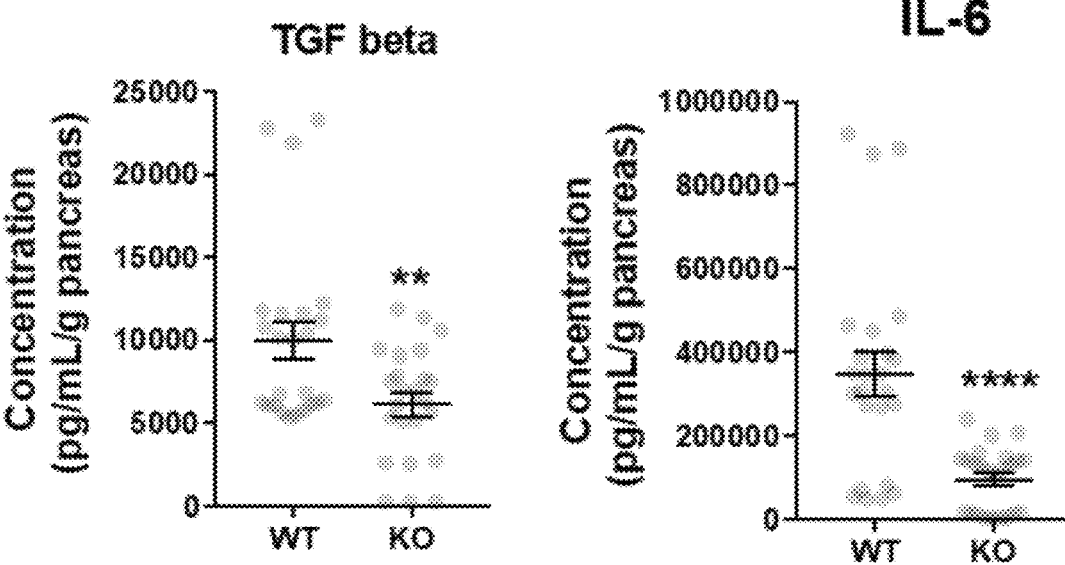
Figure 10E:
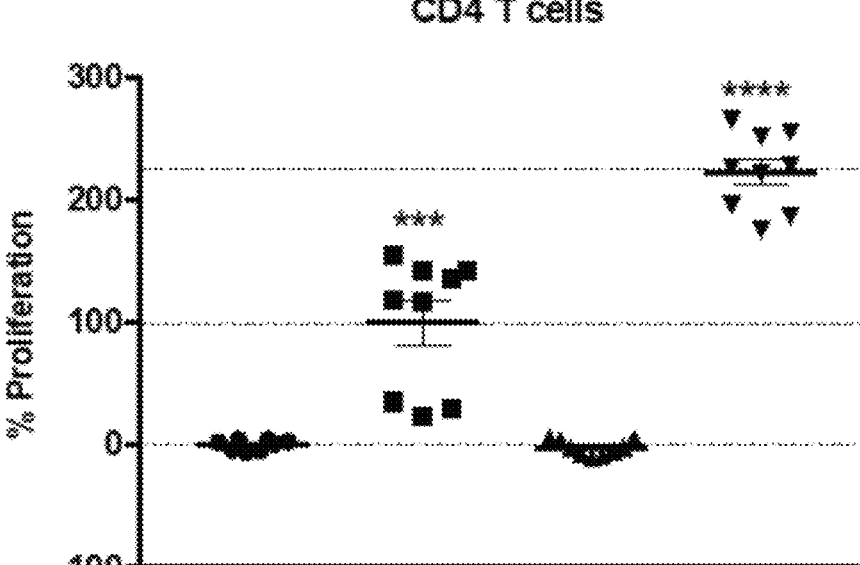
Figure 10F:
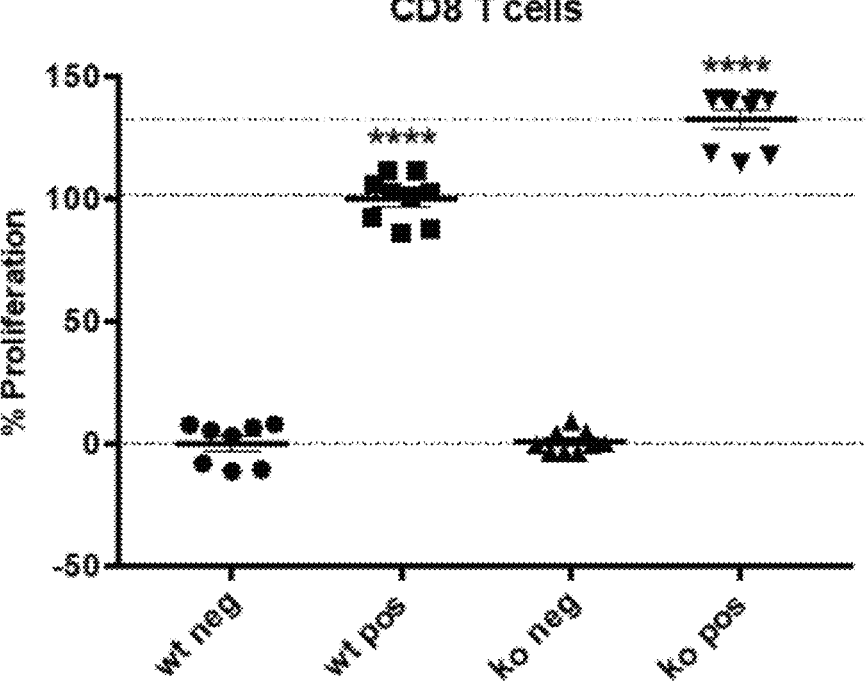

FIG. 10A shows a graph depicting tumor weight (isogenic orthotopic model as in FIG. 9) of isolated pancreata of WT and NGL-1 KO mice. FIG. 10B shows quantification of the % area of cells that was classified as normal in WT and NGL-1 KO mice. FIG. 10C shows quantification of the % of tumors cells that were classified as poorly differentiated cancer in WT and NGL-1 KO mice. FIG. 10D shows graphs depicting TGF-B and IL-6 protein levels in pancreatic tumors of WT and NGL-1 KO mice. FIG. 10E shows graphs show the % CD4 T cells (left) and CD8 T cells (right) proliferation in intact (e.g., not challenged with tumor cells in the pancreas as performed above) NGL-1 KO mice compared to WT neg.

Figure 11A:
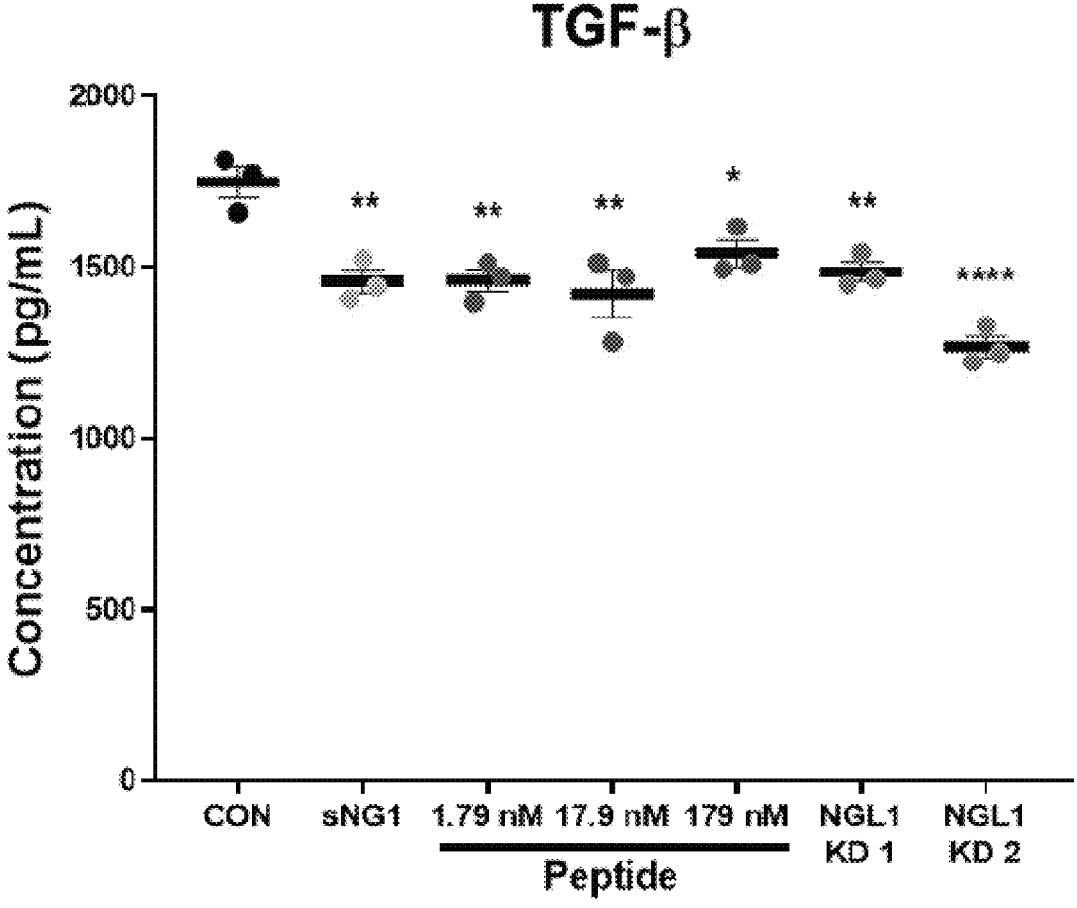
Figure 11B:
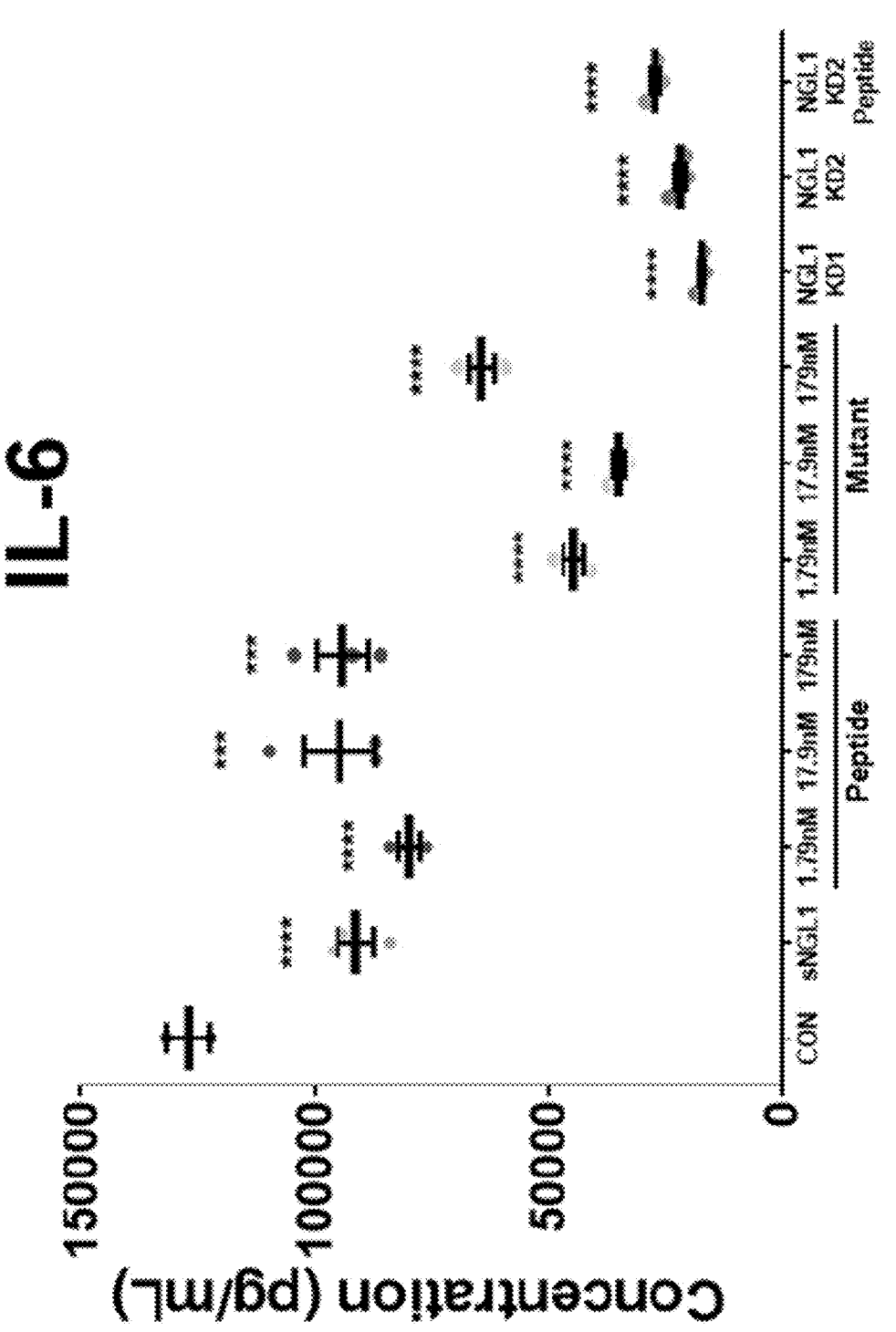
Figure 11C:
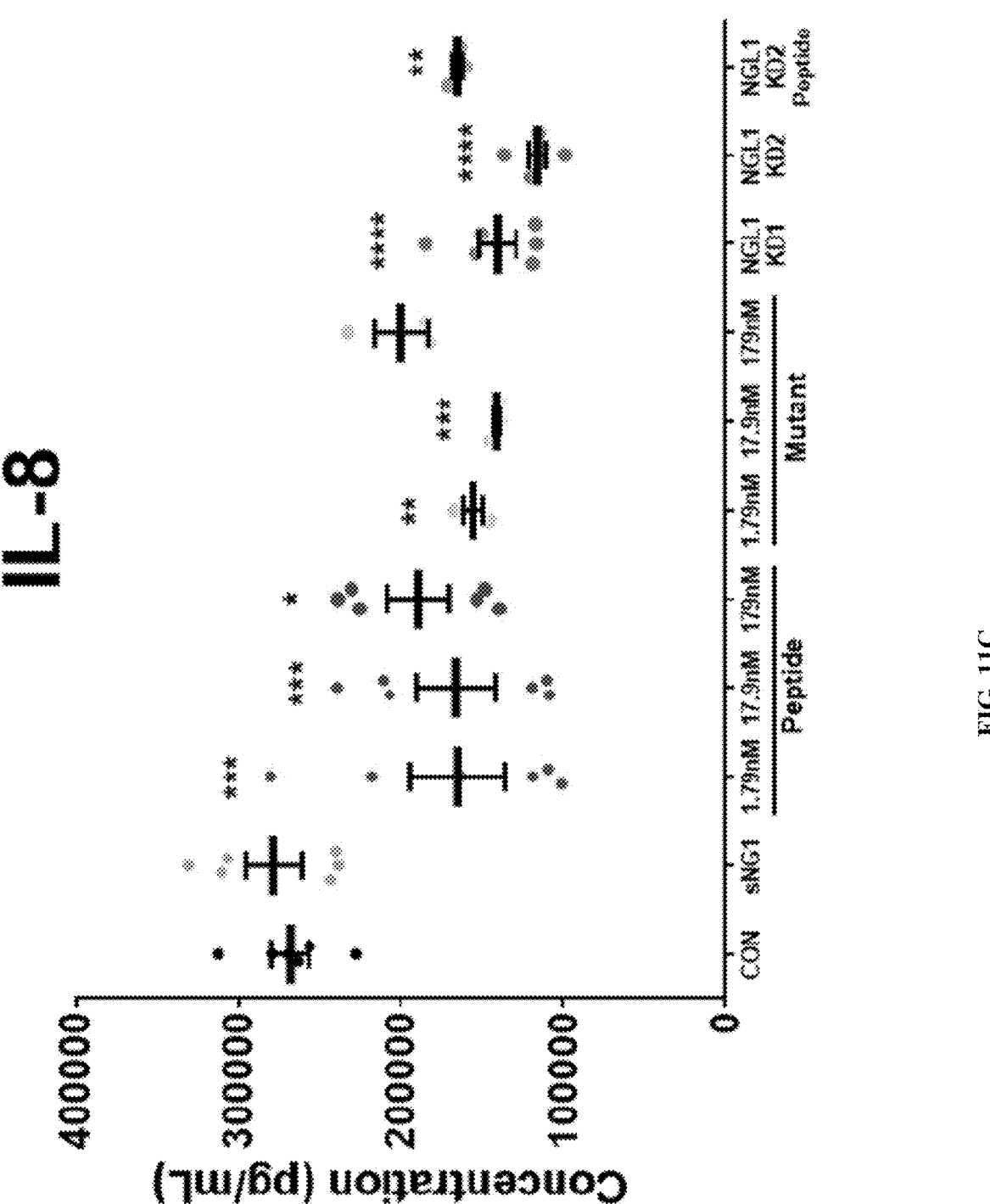

FIG. 11A shows a graph depicting amounts of CAF secreted TGF-B. FIG. 11B shows a graph depicting amounts of CAF secreted IL-6. FIG. 11C shows a graph depicting amounts of CAF secreted IL-8.

DESCRIPTION OF EMBODIMENTS

In the present disclosure, the ectopic expressions of NetrinG1 (NetG1), a neural pre-synaptic protein, in CAFs and CAF-secreted extracellular vesicles (EVs), and of NetG1's post-synaptic binding partner, NetrinG1 ligand (NGL1), in PDAC and fibroblastic cells like CAFs and other cells in the stroma like immune cells (or other cells) is described. Heterotypic CAF-to-PDAC cell-cell interactions, via NetG1/NGL1 engagement, were discovered to provide survival advantages to nutrient-deprived PDAC cells and for CAFs to protect PDAC from NK cell-driven elimination. It was further discovered that disruption of NetG1/NGL1 interaction (possibly also homeotipically in CAFs), using recombinant NetG1 or NGL1 peptides, prevents CAFs-secreted EVs from rescuing starvation-induced death of PDAC cancer cells, and moreover reverses NetG1-mediated inhibition of T-cell (and other immune cell) pro-tumor activation. The present disclosure provides methods to limit the stroma's ability to metabolically support tumor cells, as well as harness the immune system to attack cancer cells.

The terminology used herein is for the purpose of describing particular embodiments only and is not intended to be limiting. Various terms relating to aspects of disclosure are used throughout the specification and claims. Such terms are to be given their ordinary meaning in the art, unless otherwise indicated. Other specifically defined terms are to be construed in a manner consistent with the definition provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Various terms relating to embodiments of the present disclosure are used throughout the specification and claims. Such terms are to be given their ordinary meaning in the art, unless otherwise indicated. Other specifically defined terms are to be construed in a manner consistent with the definition provided in this document.

As used herein, the singular forms "a," "an," and "the" include plural referents unless expressly stated otherwise.

As used herein, the term "antibody" refers to the structure that constitutes the natural biological form of an antibody. In most mammals, including humans, and mice, this form is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_L$, $V_H$, Cγ1, Cγ2, and Cγ3. In each pair, the light and heavy chain variable regions ($V_L$ and $V_H$) are together responsible for binding to an antigen, and the constant regions (Cγ1, Cγ2, and Cγ3, particularly Cγ2 and Cγ3) are responsible for antibody effector functions. The term "antibody" also includes polyclonal, monoclonal, genetically engineered and otherwise modified forms thereof including, but not limited to, chimeric antibodies, humanized antibodies, heteroconjugate antibodies (e.g., bispecific antibodies, diabodies, triabodies, and tetrabodies).

As used herein, the phrase "antigen-binding fragment" means a fragment of an antibody that is capable of specifically interacting with a desired target. Antigen-binding fragments include, but are not limited to, Fab, Fab', $F(ab')_2$, Fv, scFv, scFv-Fc, diabody, bispecific diabody, trispecific triabody, minibody, monospecific $Fab_2$, bispecific $Fab_2$, trispecific $Fab_3$, nanobody, IgNAR, V-NAR, hcIgG, and VhH fragments. In some embodiments, scFv-Fc is produced by fusing single-chain Fv (scFv) with a hinge region from an immunoglobulin (Ig) such as an IgG, and Fc regions.

As used herein, the terms "binds" and "binding" or grammatical equivalents refer to compounds having affinity for each other.

As used herein, the phrase "chimeric antibody" refers to an antibody that has a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. A humanized antibody is a type of chimeric antibody.

As used herein, the phrases "complementarity determining region" and "CDR" refer to amino acid residues comprising non-contiguous antigen combining sites found within the variable region of both heavy and light chain polypeptides. In some embodiments, the CDRs comprise regions as described by Kabat et al., J. Biol. Chem., 1977, 252, 6609-6616 or Chothia et al., Mol. Biol., 1987, 196, 901-917. The amino acids of the CDRs of the variable domains initially defined by Kabat, based on sequence variability, consist of amino acid residues 31-35B (HI), 50-65 (H2), and 95-102 (H3) in the human heavy chain variable domain ($V_H$) and amino acid residues 24-34 (L1), 50-56 (L2), and 89-97 (L3) in the human light chain variable domain ($V_L$), using Kabat's numbering system for amino acid residues of an antibody. Chothia presented another definition of the CDRs based on residues that included the three-dimensional structural loops of the variable domain regions, which were found to be important in antigen-binding activity. Chothia defined the CDRs as consisting of amino acid residues 26-32 (H1), 52-56 (H2), and 95-102 (H3) in the human heavy chain variable domain ($V_H$), and amino acid residues 24-34 (LI), 50-56 (L2), and 89-97 (L3) in the human light chain variable domain ($V_L$). Combining the CDR definitions of Kabat and Chothia, the CDRs consist of amino acid residues 26-35B (H1), 50-65 (H2), and 95-102 (H3) in human $V_H$ and amino acid residues 24-34 (L1), 50-56 (L2), and 89-97 (L3) in human $V_L$, based on Kabat's numbering system.

As used herein, the phrase "conservative amino acid substitution" means one in which an amino acid residue is substituted by another amino acid residue having a side chain (R group) with similar chemical properties (e.g., charge and/or hydrophobicity). In general, a conservative amino acid substitution will not substantially change the functional properties of a polypeptide. As used herein, the phrase "Fab fragment" means the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the $F(ab')_2$ pepsin digestion product.

As used herein, the phrase "Fv fragment" means the minimum fragment of an antibody that contains a complete target recognition and binding site. This region consists of a dimer of one heavy and one light chain variable domain in a tight, non-covalent association (VH-VL dimer).

As used herein, the phrase "human antibodies" refers to antibodies having the amino acid sequence of a human immunoglobulin and includes antibodies isolated from human immunoglobulin libraries or from animals transgenic for one or more human immunoglobulins and that do not express endogenous immunoglobulins. Human antibodies can be made by a variety of methods including phage display methods using antibody libraries derived from human immunoglobulin sequences (see, U.S. Pat. Nos. 4,444,887 and 4,716,111; and PCT Publications WO 98/46645, WO 98/50433, WO 98/24893, WO 98/16654, WO 96/34096. WO 96/33735, and WO 91/10741). Human antibodies can also be produced using transgenic mice which are incapable of expressing functional endogenous immunoglobulins but which can express human immunoglobulin genes (see, PCT Publications WO 98/24893, WO 92/01047, WO 96/34096, and WO 96/33735; U.S. Pat. Nos. 5,413,923, 5,625,126, 5,633,425, 5,569,825, 5,661,016, 5,545,806, 5,814,318, 5,885,793, 5,916,771, and 5,939,598). Fully human antibodies that recognize a selected epitope can be generated using a technique referred to as "guided selection." In this approach, a selected non-human monoclonal antibody, e.g., a mouse antibody, is used to guide the selection of a completely human antibody recognizing the same epitope (see, Jespers et al., Biotechnology, 1988, 12, 899-903).

As used herein, the phrase "humanized antibody" refers to a chimeric antibody, or an antigen-binding fragment thereof, which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the framework (FR)

regions that are those of a human immunoglobulin sequence. The humanized antibody can also comprise at least a portion of an immunoglobulin constant region (Fc), typically that of a human immunoglobulin consensus sequence. Methods of antibody humanization include those described in, for example, U.S. Pat. Nos. 5,530,101, 5,585,089, 5,225,539, 5,693,761, 5,565,332, 5,693,762, and 6,180,370; European Patent Nos. 239400, 592106, and 519596; PCT Publication WO 91/09967; Padlan, Mol. Immunol., 1991, 28, 489498, Studnicka et al., 1994, Prot. Eng., 7, 805-814; Roguska et al., Proc. Natl. Acad. Sci., 1994, 91, 969-973, and Riechmann et al., Nature, 1988, 332, 323-7.

As used herein, the phrase "in need thereof" means that the "subject" or "patient" has been identified as having a need for the particular method, prevention, or treatment. In some embodiments, the identification can be by any means of diagnosis. In any of the methods, preventions, and treatments described herein, the "subject" or "patient" can be in need thereof.

As used herein, the term "isolated" means that the polypeptide or antibody is in a condition other than its native environment, such as apart from blood and animal tissue. In some embodiments, the isolated polypeptide or antibody is substantially free of other polypeptides and/or antibodies, particularly other polypeptides and/or antibodies of animal origin such as enzymes, hormones, and other proteinaceous or nonproteinaceous solutes. In some embodiments, the polypeptides and antibodies are in a highly purified form, i.e., greater than 95% or greater than 99%. When used in this context, the term "isolated" does not exclude the presence of the same polypeptide or antibody in alternative physical forms, such as dimers or alternatively glycosylated or derivatized forms.

As used herein, the terms "$K_{assoc}$" and "$K_a$" refer to the association rate of a particular antibody-antigen interaction, whereas the terms "$K_{dis}$" and "$K_a$," refer to the dissociation rate of a particular antibody-antigen interaction.

As used herein, the term "$K_D$" refers to the dissociation constant, which is obtained from the ratio of $K_a$ to $K_a$ (i.e., $K_a/K_a$) and is expressed as a molar concentration (M).

As used herein, the phrase "monoclonal antibody" refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts.

As used herein, the phrase "nucleic acid molecule" refers to a polymeric form of nucleotides of any length, may comprise DNA and/or RNA, and can be single-stranded, double-stranded, or multiple stranded. One strand of a nucleic acid also refers to its complement.

As used herein, the phrase "polyclonal antibody" refers to a mixture of antibodies which are genetically different since produced by different plasma cells and which recognize a different epitope of the same antigen.

As used herein, the phrase "primatized antibody" refers to an antibody comprising monkey variable regions and human constant regions.

As used herein, the term "recombinant antibody" includes all antibodies of the disclosure that are prepared, expressed, created, or isolated by recombinant means, such as antibodies isolated from an one animal (e.g., a mouse) that is transgenic for another animal's (e.g. a dog) immunoglobulin genes; antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences. Such recombinant antibodies have variable and constant regions (if present) derived from a particular animal's germline immunoglobulin sequences. Such antibodies can, however, be subjected to in vitro mutagenesis (or, when an animal transgenic for another species Ig sequences is used, in vivo somatic mutagenesis) and, thus, the amino acid sequences of the $V_H$ and $V_L$ regions of the recombinant antibodies are sequences that, while derived from and related to e.g. human germline Vu and $V_L$ sequences, may not naturally exist within the human antibody germline repertoire in vivo.

As used herein, the phrase "regulatory sequence" refers to promoters, enhancers, and other expression control elements, such as polyadenylation signals, that control the transcription or translation of antibody chain genes.

As used herein, the phrases "single-chain Fv" or "scFv" antibody means the binding fragments comprise the $V_H$ and $V_L$ domains of an antibody, where these domains are present in a single polypeptide chain. Generally, the Fv polypeptide further comprises a polypeptide linker between the $V_H$ and $V_L$ domains which enables the scFv to form the desired structure for target binding.

As used herein, the phrase "single domain antibodies" means antibodies that are composed of a single $V_H$ or $V_L$ domain which exhibits sufficient affinity to NetG1 or NGK.

As used herein, the phrases "specific binding" and "specifically (or selectively) binds" refer to preferential binding of an antibody to a specified antigen relative to other non-specified antigens. Typically, an antibody binds with a dissociation constant ($K_D$)) of about $1\times10^{-7}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less, and binds to the specified antigen with an affinity that is at least two-fold greater than its affinity for binding to a non-specific antigen other than the specified antigen or a closely-related antigen. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target.

As used herein, the terms "subject" and "patient" are used interchangeably. A subject may be any animal, such as a mammal. A mammalian subject may be a farm animal (e.g., sheep, horse, cow, pig), a companion animal (e.g., cat, dog), a rodent or laboratory animal (e.g., mouse, rat, rabbit), or a non-human primate (e.g., old world monkey, new world monkey). In some embodiments, the mammal is a human.

As used herein, the terms "treat", "treating" and "treatment" and the terms "prevent", "preventing" and "prevention" refer to eliciting the desired biological response, i.e., a therapeutic and prophylactic effect, respectively.

As used herein, the term "$V_H$" refers to the variable region of a heavy chain of an antibody, including the heavy chain of, for example, an Fv, scFv, or Fab fragment.

As used herein, the term "$V_L$" refers to the variable region of a light chain of an antibody, including the light chain of, for example, an Fv, scFv, dsFv, or Fab fragment.

The present disclosure provides isolated Netrin G1 (NetG1) polypeptides. In some embodiments, the NetG1 is NetG1m, NetG1a, NetG1c, NetG1n, NetG1o, NetG1b, NetG1d, NetG1e, NetG1l or any other alternative form (or splice variant) of NetG1. The human NetG1 polypeptide has a length of 539 amino acids. The amino acid sequence of human NetG1 has the GenBank accession number NP_001106697 and is set forth as:

```
                                          (SEQ ID NO: 12)
MYLSRFLSIHALWVTVSSVMQPYPLVWGHYDLCKTQIYTEEGKVWDYMAC

QPESTDMTKYLKVKLDPPDITCGDPPETFCAMGNPYMCNNECDASTPELA

HPPELMFDFEGRHPSTFWQSATWKEYPKPLQVNITLSWSKTIELTDNIVI

TFESGRPDQMILEKSLDYGRTWQPYQYYATDCLDAFHMDPKSVKDLSQHT

VLEIICTEEYSTGYTTNSKTIIHFEIKDRFAFFAGPRLRNMASLYGQLDT

TKKLRDFFTVTDLRIRLLRPAVGEIFVDELHLARYFYAISDIKVRGRCKC

NLHATVCVYDNSKLTCECEHNTTGPDCGKCKKNYQGRPWSPGSYLPIPKG

TANTCIPSISSIGNCECFGHSNRCSYIDLLNTVICVSCKHNTRGQHCELC

RLGYFRNASAQLDDENVCIECYCNPLGSIHDRCNGSGFCECKTGTTGPKC

DECLPGNSWHYGCQPNVCDNELLHCQNGGTCHNNVRCLCPAAYTGILCEK

LRCEEAGSCGSDSGQGAPPHGSPALLLLTTLLGTASPLVF.
```

In some embodiments, the isolated NetG1 polypeptide comprises up to 20 amino acids, up to 21 amino acids, up to 22 amino acids, up to 23 amino acids, or up to 24 amino acids. In some embodiments, the isolated NetG1 polypeptide comprises up to 20 amino acids. In some embodiments, the isolated NetG1 polypeptide comprises up to 21 amino acids. In some embodiments, the isolated NetG1 polypeptide comprises up to 22 amino acids. In some embodiments, the isolated NetG1 polypeptide comprises up to 23 amino acids. In some embodiments, the isolated NetG1 polypeptide comprises up to 24 amino acids. The additional amino acids (compared to the specific amino acid sequences listed below) can be inserted at the amino terminus, the carboxy terminus, or both. For example, an isolated NetG1 polypeptide that comprises up to 20 amino acids and also comprises a specific amino acid sequence that consists of 16 amino acids (e.g., SEQ ID NO:3), can have all or any number of the additional four amino acids inserted at the amino terminus, the carboxy terminus, or both. For instance, all four additional amino acids can be inserted at the amino terminus or the carboxy terminus, three amino acids can be inserted at the amino terminus and one amino acid inserted at the carboxy terminus, three amino acids can be inserted at the carboxy terminus and one amino acid inserted at the amino terminus, or two amino acids can be inserted at the amino terminus and two amino acids inserted at the carboxy terminus.

In some embodiments, the isolated NetG1 polypeptide comprises up to 20 amino acids and comprises: TFCAMGNPYMCNNE (SEQ ID NO:1), TFSAMGNPYMCNNE (SEQ ID NO: 16), TFCAMGNPYMSNNE (SEQ ID NO:17), TFSAMGNPYMSNNE (SEQ ID NO:18), GNPYMCNNE (SEQ ID NO:2), GNPYMSNNE (SEQ ID NO:19), AVGE-IFVDELHLARYF (SEQ ID NO:3), VGEIFV (SEQ ID NO:4), EYSTGYTTNSK (SEQ ID NO:5), STGYTT (SEQ ID NO: 6), ATDCLDAFHMDP (SEQ ID NO:7), ATD-SLDAFHMDP (SEQ ID NO:20), ATDCLDAFH (SEQ ID NO:8), ATDSLDAFH (SEQ ID NO:21), TFCAMGNPTMCNNE (SEQ ID NO: 9), TFSAMGNPTMCNNE (SEQ ID NO:22), TFCAMGNPTMSNNE (SEQ ID NO:23), TFSAMGNPTMSNNE (SEQ ID NO:24), GNPTMCNNE (SEQ ID NO:10), GNPTMSNNE (SEQ ID NO:25), NPYMCNNE (SEQ ID NO:14), NPYMSNNE (SEQ ID NO:26), NPTMCNNE (SEQ ID NO:15), or NPTMSNNE (SEQ ID NO:27). In some embodiments, the isolated NetG1 polypeptide further comprises zero, one, two, three, or four conservative amino acid substitutions. In some embodiments, the isolated NetG1 polypeptide further comprises zero, one, two, or three conservative amino acid substitutions. In some embodiments, the NetG1 polypeptide further comprises zero, one, or two conservative amino acid substitutions. In some embodiments, the isolated NetG1 polypeptide further comprises zero or one conservative amino acid substitutions. In some embodiments, the isolated NetG1 polypeptide further comprises one conservative amino acid substitution. In some embodiments, the isolated NetG1 polypeptide further comprises two conservative amino acid substitutions. In some embodiments, the isolated NetG1 polypeptide further comprises three conservative amino acid substitutions. In some embodiments, the isolated NetG1 polypeptide further comprises four conservative amino acid substitutions.

In some embodiments, the isolated NetG1 polypeptide comprises up to 18 amino acids and comprises TFCAMGNPYMCNNE (SEQ ID NO:1). In some embodiments, the isolated NetG1 polypeptide comprises up to 18 amino acids and comprises TFSAMGNPYMCNNE (SEQ ID NO: 16). In some embodiments, the isolated NetG1 polypeptide comprises up to 18 amino acids and comprises TFCAMGNPYMSNNE (SEQ ID NO:17). In some embodiments, the isolated NetG1 polypeptide comprises up to 18 amino acids and comprises TFSAMGNPYMSNNE (SEQ ID NO:18). In some embodiments, the isolated NetG1 polypeptide comprises up to 13 amino acids and comprises GNPYMCNNE (SEQ ID NO:2). In some embodiments, the isolated NetG1 polypeptide comprises up to 13 amino acids and comprises GNPYMSNNE (SEQ ID NO:19). In some embodiments, the isolated NetG1 polypeptide comprises up to 20 amino acids and comprises AVGEIFVDELHLARYF (SEQ ID NO:3). In some embodiments, the isolated NetG1 polypeptide comprises up to 10 amino acids and comprises VGEIFV (SEQ ID NO:4). In some embodiments, the isolated NetG1 polypeptide comprises up to 15 amino acids and comprises EYSTGYTTNSK (SEQ ID NO:5). In some embodiments, the isolated NetG1 polypeptide comprises up to 10 amino acids and comprises STGYTT (SEQ ID NO:6). In some embodiments, the isolated NetG1 polypeptide comprises up to 16 amino acids and comprises ATD-CLDAFHMDP (SEQ ID NO:7). In some embodiments, the isolated NetG1 polypeptide comprises up to 16 amino acids and comprises ATDSLDAFHMDP (SEQ ID NO:20). In some embodiments, the isolated NetG1 polypeptide comprises up to 13 amino acids and comprises ATDCLDAFH (SEQ ID NO:8). In some embodiments, the isolated NetG1 polypeptide comprises up to 13 amino acids and comprises ATDSLDAFH (SEQ ID NO:21). In some embodiments, the isolated NetG1 polypeptide comprises up to 18 amino acids and comprises TFCAMGNPTMCNNE (SEQ ID NO:9). In some embodiments, the isolated NetG1 polypeptide comprises up to 18 amino acids and comprises TFSAMGNPTMCNNE (SEQ ID NO:22). In some embodiments, the isolated NetG1 polypeptide comprises up to 18 amino acids and comprises TFCAMGNPTMSNNE (SEQ ID NO:23). In some embodiments, the isolated NetG1 polypeptide comprises up to 18 amino acids and comprises TFSAMGNPTMSNNE (SEQ ID NO:24). In some embodiments, the isolated NetG1 polypeptide comprises up to 13 amino acids and comprises GNPTMCNNE (SEQ ID NO:10). In some embodiments, the isolated NetG1 polypeptide comprises up to 13 amino acids and comprises GNPTMSNNE (SEQ ID NO:25). In some embodiments, the isolated NetG1 polypeptide comprises up to 12 amino acids and comprises NPYMCNNE (SEQ ID NO:14). In some embodiments, the isolated NetG1 polypeptide comprises up to 12 amino acids and comprises NPYMSNNE (SEQ ID NO:26). In some embodiments, the isolated NetG1 polypeptide comprises up to 12 amino acids and comprises NPTMCNNE (SEQ ID NO:15). In some embodiments, the isolated NetG1 polypeptide comprises up to 12 amino acids and comprises NPTMSNNE (SEQ ID NO:27). In some embodiments, the isolated NetG1 polypeptide further comprises zero, one, two, three, or four conservative amino acid substitutions. In some embodiments, the isolated NetG1 polypeptide further comprises zero, one, two, or three conservative amino acid substitutions. In some embodiments, the NetG1 polypeptide further comprises zero, one, or two conservative amino acid substitutions. In some embodiments, the isolated NetG1 polypeptide further comprises zero or one conservative amino acid substitutions. In some embodiments, the isolated NetG1 polypeptide further comprises one conservative amino acid substitution. In some embodiments, the isolated NetG1 polypeptide further comprises two conservative amino acid substitutions. In some embodiments, the isolated NetG1 polypeptide further comprises three conservative amino acid substitutions. In some embodiments, the isolated NetG1 polypeptide further comprises four conservative amino acid substitutions.

In some embodiments, the isolated NetG1 polypeptide consists of SEQ ID NO:1, SEQ ID NO: 16, SEQ ID NO: 17, SEQ ID NO: 18, SEQ ID NO:2, SEQ ID NO: 19, SEQ ID NO:3, SEQ ID NO: 4, SEQ ID NO:5, SEQ ID NO:6, SEQ ID NO:7, SEQ ID NO:20, SEQ ID NO:8, SEQ ID NO: 21, SEQ ID NO:9, SEQ ID NO:22, SEQ ID NO:23, SEQ ID NO:24, SEQ ID NO: 10, SEQ ID NO: 25, SEQ ID NO: 14, SEQ ID NO:26, SEQ ID NO: 15, or SEQ ID NO:27. In some embodiments, the isolated NetG1 polypeptide consists of SEQ ID NO: 1. In some embodiments, the isolated NetG1 polypeptide consists of SEQ ID NO: 16. In some embodiments, the isolated NetG1 polypeptide consists of SEQ ID NO: 17. In some embodiments, the isolated NetG1 polypeptide consists of SEQ ID NO: 18. In some embodiments, the isolated NetG1 polypeptide consists of SEQ ID NO:2. In some embodiments, the isolated NetG1 polypeptide consists of SEQ ID NO: 19. In some embodiments, the isolated NetG1 polypeptide consists of SEQ ID NO: 3. In some embodiments, the isolated NetG1 polypeptide consists of SEQ ID NO:4. In some embodiments, the isolated NetG1 polypeptide consists of SEQ ID NO:5. In some embodiments, the isolated NetG1 polypeptide consists of SEQ ID NO:6. In some embodiments, the isolated NetG1 polypeptide consists of SEQ ID NO:7. In some embodiments, the isolated NetG1 polypeptide consists of SEQ ID NO:20. In some embodiments, the isolated NetG1 polypeptide consists of SEQ ID NO:8. In some embodiments, the isolated NetG1 polypeptide consists of SEQ ID NO:21. In some embodiments, the isolated NetG1 polypeptide consists of SEQ ID NO: 9. In some embodiments, the isolated NetG1 polypeptide consists of SEQ ID NO:22. In some embodiments, the isolated NetG1 polypeptide consists of SEQ ID NO:23. In some embodiments, the isolated NetG1 polypeptide consists of SEQ ID NO:24. In some embodiments, the isolated NetG1 polypeptide consists of SEQ ID NO: 10. In some embodiments, the isolated NetG1 polypeptide consists of SEQ ID NO:25. In some embodiments, the isolated NetG1 polypeptide consists of SEQ ID NO: 14. In some embodiments, the isolated NetG1 polypeptide consists of SEQ ID NO:26. In some embodiments, the isolated NetG1 polypeptide consists of SEQ ID NO:15. In some embodiments, the isolated NetG1 polypeptide consists of SEQ ID NO: 27. In some embodiments, the isolated NetG1 polypeptide further comprises zero, one, two, three, or four conservative amino acid substitutions. In some embodiments, the isolated NetG1 polypeptide further comprises zero, one, two, or three conservative amino acid substitutions. In some embodiments, the NetG1 polypeptide further comprises zero, one, or two conservative amino acid substitutions. In some embodiments, the isolated NetG1 polypeptide further comprises zero or one conservative amino acid substitutions. In some embodiments, the isolated NetG1 polypeptide further comprises one conservative amino acid substitution. In some embodiments, the isolated NetG1 polypeptide further comprises two conservative amino acid substitutions. In some embodiments, the isolated NetG1 polypeptide further comprises three conservative amino acid substitutions. In some embodiments, the isolated NetG1 polypeptide further comprises four conservative amino acid substitutions. In some embodiments, any of the isolated NetG1 polypeptides described herein can comprise, one, two, three, or four additional amino acids (which can be distributed at the N-terminus, the C-terminus, or any number distributed between the N-terminus and the C-terminus).

The present disclosure also provides Netrin G1 ligand (NGL-1) polypeptides. The human NGL-1 polypeptide has a length of 640 amino acids. The amino acid sequence of human NGL-1 has the GenBank accession number NP_001245348 and is set forth as:

```
                                      (SEQ ID NO: 13)
MLNKMTLHPQQIMIGPRFNRALFDPLLVVLLALQLLVVAGLVRAQTCPSV

CSCSNQFSKVICVRKNLREVPDGISTNTRLLNLHENQIQIIKVNSFKHLR

HLEILQLSRNHIRTIEIGAFNGLANLNTLELFDNRLTTIPNGAFVYLSKL

KELWLRNNPIESIPSYAFNRIPSLRRLDLGELKRLSYISEGAFEGLSNLR

YLNLAMCNLREIPNLTPLIKLDELDLSGNHLSAIRPGSFQGLMHLQKLWM

IQSQIQVIERNAFDNLQSLVEINLAHNNLTLLPHDLFTPLHHLERIHLHH

NPWNCNCDILWLSWWIKDMAPSNTACCARCNTPPNLKGRYIGELDQNYFT

CYAPVIVEPPADLNVTEGMAAELKCRASTSLTSVSWITPNGTVMTHGAYK

VRIAVLSDGTLNFTNVTVQDTGMYTCMVSNSVGNTTASATLNVTAATTTP

FSYFSTVTVETMEPSQDEARTTDNNVGPTPVVDWETTNVTTSLTPQSTRS

TEKTFTIPVTDINSGIPGIDEVMKTTKIIIGCFVAITLMAAVMLVIFYKM

RKQHHRQNHHAPTRTVEIINVDDEITGDTPMESHLPMPAIEHEHLNHYNS

YKSPFNHTTTVNTINSIHSSVHEPLLIRMNSKDNVQETQI.
```

In some embodiments, the isolated NGL-1 polypeptide comprises up to 20 amino acids, up to 21 amino acids, up to 22 amino acids, up to 23 amino acids, or up to 24 amino acids. In some embodiments, the isolated NGL-1 polypeptide comprises up to 20 amino acids. In some embodiments, the isolated NGL-1 polypeptide comprises up to 21 amino acids. In some embodiments, the isolated NGL-1 polypeptide comprises up to 22 amino acids. In some embodiments, the isolated NGL-1 polypeptide comprises up to 23 amino acids. In some embodiments, the isolated NGL-1 polypeptide comprises up to 24 amino acids. The additional amino acids (compared to the specific amino acid sequences listed below) can be inserted at the amino terminus, the carboxy terminus, or both. For example, an isolated NGL-1 polypeptide that comprises up to 20 amino acids and also comprises a specific amino acid sequence that consists of 14 amino acids (e.g., SEQ ID NO:11), can have all or any number of the additional six amino acids inserted at the amino terminus, the carboxy terminus, or both. For instance, all six additional amino acids can be inserted at the amino terminus or the carboxy terminus, five amino acids can be inserted at the amino terminus and one amino acid inserted at the carboxy terminus, five amino acids can be inserted at the carboxy terminus and one amino acid inserted at the amino terminus, four amino acids can be inserted at the amino terminus and two amino acids inserted at the carboxy terminus, four amino acids can be inserted at the carboxy terminus and two amino acids inserted at the amino terminus, or three amino acids can be inserted at the amino terminus and three amino acids inserted at the carboxy terminus.

In some embodiments, the isolated NGL-1 polypeptide comprises up to 20 amino acids and comprises VCSCSNQFSKVICV (SEQ ID NO:11). In some embodiments, the isolated NGL-1 polypeptide comprises up to 20 amino acids and comprises VSSCSNQFSKVICV (SEQ ID NO: 28). In some embodiments, the isolated NGL-1 polypeptide comprises up to 20 amino acids and comprises VCSSSNQFSKVICV (SEQ ID NO:29). In some embodiments, the isolated NGL-1 polypeptide comprises up to 20 amino acids and comprises VCSCSNQFSKVISV (SEQ ID NO: 30). In some embodiments, the isolated NGL-1 polypeptide comprises up to 20 amino acids and comprises VSSSSNQFSKVICV (SEQ ID NO:31). In some embodiments, the isolated NGL-1 polypeptide comprises up to 20 amino acids and comprises VSSCSNQFSKVISV (SEQ ID NO: 32). In some embodiments, the isolated NGL-1 polypeptide comprises up to 20 amino acids and comprises VCSSSNQFSKVISV (SEQ ID NO:33). In some embodiments, the isolated NGL-1 polypeptide comprises up to 20 amino acids and comprises VSSSSNQFSKVISV (SEQ ID NO: 34). In some embodiments, the isolated NGL-1 polypeptide further comprises zero, one, two, three, or four conservative amino acid substitutions. In some embodiments, the isolated NGL-1 polypeptide further comprises zero, one, two, or three conservative amino acid substitutions. In some embodiments, the NGL-1 polypeptide further comprises zero, one, or two conservative amino acid substitutions. In some embodiments, the isolated NGL-1 polypeptide further comprises zero or one conservative amino acid substitutions. In some embodiments, the isolated NGL-1 polypeptide further comprises one conservative amino acid substitution. In some embodiments, the isolated NGL-1 polypeptide further comprises two conservative amino acid substitutions. In some embodiments, the isolated NGL-1 polypeptide further comprises three conservative amino acid substitutions. In some embodiments, the isolated NGL-1 polypeptide further comprises four conservative amino acid substitutions.

In some embodiments, the isolated NGL-1 polypeptide comprises up to 18 amino acids and comprises VCSCSNQFSKVICV (SEQ ID NO:11). In some embodiments, the isolated NGL-1 polypeptide comprises up to 18 amino acids and comprises VSSCSNQFSKVICV (SEQ ID NO: 28). In some embodiments, the isolated NGL-1 polypeptide comprises up to 18 amino acids and comprises VCSSSNQFSKVICV (SEQ ID NO:29). In some embodiments, the isolated NGL-1 polypeptide comprises up to 18 amino acids and comprises VCSCSNQFSKVISV (SEQ ID NO: 30). In some embodiments, the isolated NGL-1 polypeptide comprises up to 18 amino acids and comprises VSSSSNQFSKVICV (SEQ ID NO:31). In some embodiments, the isolated NGL-1 polypeptide comprises up to 18 amino acids and comprises VSSCSNQFSKVISV (SEQ ID NO: 32). In some embodiments, the isolated NGL-1 polypeptide comprises up to 18 amino acids and comprises VCSSSNQFSKVISV (SEQ ID NO:33). In some embodiments, the isolated NGL-1 polypeptide comprises up to 18 amino acids and comprises VSSSSNQFSKVISV (SEQ ID NO: 34). In some embodiments, the isolated NGL-1 polypeptide further comprises zero, one, two, three, or four conservative amino acid substitutions. In some embodiments, the isolated NGL-1 polypeptide further comprises zero, one, two, or three conservative amino acid substitutions. In some embodiments, the NGL-1 polypeptide further comprises zero, one, or two conservative amino acid substitutions. In some embodiments, the isolated NGL-1 polypeptide further comprises zero or one conservative amino acid substitutions. In some embodiments, the isolated NGL-1 polypeptide further comprises one conservative amino acid substitution. In some embodiments, the isolated NGL-1 polypeptide further comprises two conservative amino acid substitutions. In some embodiments, the isolated NGL-1 polypeptide further comprises three conservative amino acid substitutions. In some embodiments, the isolated NGL-1 polypeptide further comprises four conservative amino acid substitutions.

In some embodiments, the isolated NGL-1 polypeptide consists of SEQ ID NO: 11, SEQ ID NO: 28, SEQ ID NO:29, SEQ ID NO:30, SEQ ID NO:31, SEQ ID NO:32, SEQ ID NO:33, or SEQ ID NO:34. In some embodiments, the isolated NGL-1 polypeptide consists of VCSCSNQFSKVICV (SEQ ID NO:11). In some embodiments, the isolated NGL-1 polypeptide consists of VSS-CSNQFSKVICV (SEQ ID NO:28). In some embodiments, the isolated NGL-1 polypeptide consists of VCSSSNQFSKVICV (SEQ ID NO:29). In some embodiments, the isolated NGL-1 polypeptide consists of VCSCSNQFSKVISV (SEQ ID NO:30). In some embodiments, the isolated NGL-1 polypeptide consists of VSSSSNQFSKVICV (SEQ ID NO: 31). In some embodiments, the isolated NGL-1 polypeptide consists of VSS-CSNQFSKVISV (SEQ ID NO:32). In some embodiments, the isolated NGL-1 polypeptide consists of VCSSSNQFSKVISV (SEQ ID NO:33). In some embodiments, the isolated NGL-1 polypeptide consists of VSSSSNQFSKVISV (SEQ ID NO:34). In some embodiments, the isolated NGL-1 polypeptide further comprises zero, one, two, three, or four conservative amino acid substitutions. In some embodiments, the isolated NGL-1 polypeptide further comprises zero, one, two, or three conservative amino acid substitutions. In some embodiments, the NGL-1 polypeptide further comprises zero, one, or two conservative amino acid substitutions. In some embodiments, the isolated NGL-1 polypeptide further comprises zero or one conservative amino acid substitutions. In some embodiments, the isolated NGL-1 polypeptide further comprises one conservative amino acid substitution. In some embodiments, the isolated NGL-1 polypeptide further comprises two conservative amino acid substitutions. In some embodiments, the isolated NGL-1 polypeptide further comprises three conservative amino acid substitutions. In some embodiments, the isolated NGL-1 polypeptide further comprises four conservative amino acid substitutions. In some embodiments, any of the isolated NGL-1 polypeptides described herein can comprise, one, two, three, or four additional amino acids (which can be distributed at the N-terminus, the C-terminus, or any number distributed between the N-terminus and the C-terminus).

A conservative amino acid substitution can be any substitution of an amino acid that is normally present in a polypeptide with a different amino acid of similar size, charge, or polarity. Examples of conservative amino acid substitutions include, but are not limited to, the substitution of a non-polar (hydrophobic) residue such as isoleucine, valine, or leucine for another non-polar residue. Likewise, examples of conservative amino acid substitutions include, but are not limited to, the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative amino acid substitutions. Examples of non-conservative substitutions include, but are not limited to, the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Any of the peptides described herein may have one or more cysteines replaced by serines. Typical amino acid categorizations are summarized below.

| Alanine | Ala | A | Nonpolar | Neutral | 1.8 |
|---|---|---|---|---|---|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

In addition, the following six groups each contain amino acids that are conservative substitutions for one another: 1) serine and threonine, 2) aspartic acid and glutamic acid; 3) asparagine and glutamine; 4) arginine and lysine; 5) isoleucine, leucine, methionine, alanine, and valine; and 6) phenylalanine, tyrosine, and tryptophan. In some embodiments, a conservative amino acid substitution is a substitution that scores at least 0 on the BLOSUM62 matrix of Henikoff and Henikoff, Proc. Natl. Acad. Sci. USA, 1992, 89, 10915-10919. For example, an amino acid substitution is conservative if the substitution is characterized by a BLOSUM62 value of 0, 1, 2, or 3. Suitable conservative amino acid substitutions are characterized by a BLOSUM62 value of at least one 1 (e.g., 1, 2 or 3), while more suitable conservative amino acid substitutions are characterized by a BLOSUM62 value of at least 2 (e.g., 2 or 3).

In some embodiments, the isolated NetG1 polypeptide or NGL-1 polypeptide is linked or fused to a heterologous polypeptide. In some embodiments, the heterologous polypeptide is an affinity tag, a fluorescent protein, or an epitope tag. In some embodiments, the heterologous polypeptide is an affinity tag. In some embodiments, the heterologous polypeptide is a fluorescent protein. In some embodiments, the heterologous polypeptide is an epitope tag. In some embodiments, the NetG1 polypeptide or NGL-1 polypeptide is linked or fused to a fluorescein tag. In some embodiments, the NetG1 polypeptide or NGL-1 polypeptide is linked or fused to FITC. In some embodiments, the NetG1 polypeptide or NGL-1 polypeptide is linked or fused to beta alanine.

In some embodiments, the NetG1 polypeptide or NGL-1 polypeptide is labeled. In some embodiments, the label is a fluorescent label or a radiolabel. In some embodiments, the label is a fluorescent label. In some embodiments, the label is a radiolabel.

The present disclosure also provides nucleic acid molecules having a nucleotide sequence encoding any of the NetG1 polypeptides or NGL-1 polypeptides described herein.

The present disclosure also provides vectors comprising the nucleic acid molecules encoding any of the NetG1 polypeptides or NGL-1 polypeptides described herein. In some embodiments, the vector is a plasmid or a virus. In some embodiments, the vector is a plasmid. In some embodiments, the vector is a virus. The vectors can be used for propagating the nucleic acid molecule in host cells (cloning vectors), for shuttling the nucleic acid molecule between host cells derived from disparate organisms (shuttle vectors), for inserting the nucleic acid molecule into host cell chromosomes (insertion vectors), for expressing sense or antisense RNA transcripts of the nucleic acid molecule in vitro or within a host cell, and for expressing polypeptides encoded by the nucleic acid molecules, alone or as fusions to heterologous polypeptides (expression vectors).

The nucleic acid molecules can be expressed by operatively linking them to an expression control sequence in an appropriate expression vector and employing that expression vector to transform an appropriate host call. Expression control sequences are sequences which control the transcription, post-transcriptional events, and translation of nucleic acid molecules. Such operative linking of a nucleic acid molecule to an expression control sequence includes, if not already part of the nucleic acid molecule, the provision of a translation initiation codon, ATG or GTG, in the correct reading frame upstream of the nucleic acid sequence.

A variety of expression control sequences can be used in the vectors to express the nucleic acid molecules. Such expression control sequences include the expression control sequences associated with structural genes of the foregoing expression vectors. Expression control sequences that control transcription include, but are not limited to, promoters, enhancers, and transcription termination sites. Expression control sequences in eukaryotic cells that control post-transcriptional events include, but are not limited to, splice donor and acceptor sites and sequences that modify the half-life of the transcribed RNA, such as sequences that direct poly(A) addition or binding sites for RNA-binding proteins. Expression control sequences that control translation include, but are not limited to, ribosome binding sites, sequences which direct targeted expression of the polypeptide to or within particular cellular compartments, and sequences in the 5' and 3' untranslated regions that modify the rate or efficiency of translation.

Examples of useful expression control sequences for a prokaryote, such as *E. coli*, include, but are not limited to, a promoter, often a phage promoter, such as phage lambda pL promoter, the trc promoter, a hybrid derived from the trp and lac promoters, the bacteriophage T7 promoter (in *E. coli* cells engineered to express the T7 polymerase), the TAC or TRC system, the major operator and promoter regions of phage lambda, the control regions of fd coat protein, and the araBAD operon. Prokaryotic expression vectors can further include transcription terminators, such as the aspA terminator, and elements that facilitate translation, such as a consensus ribosome binding site and translation termination codon.

Expression control sequences for yeast cells, typically *S. cerevisiae*, include, but are not limited to, a yeast promoter, such as the CYC1 promoter, the GALI promoter, the GAL10 promoter, ADHI promoter, the promoters of the yeast-mating system, and the GPD promoter, and will typically have elements that facilitate transcription termination, such as the transcription termination signals from the CYC1 or ADHI gene.

Expression vectors useful for expressing proteins in mammalian cells include a promoter active in mammalian cells. These promoters include, but are not limited to, those derived from mammalian viruses, such as the enhancer-promoter sequences from the immediate early gene of the human cytomegalovirus (CMV), the enhancer-promoter sequences from the Rous sarcoma virus long terminal repeat (RSV LTR), and the enhancer-promoter from SV40 or the early and late promoters of adenovirus. Other expression control sequences include, but are not limited to, the promoter for 3-phosphoglycerate kinase and other glycolytic enzymes, the promoters of acid phosphatase. Often, expression is enhanced by incorporation of polyadenylation sites, such as the late SV40 polyadenylation site and the polyadenylation signal and transcription termination sequences from the bovine growth hormone (BGH) gene, and ribosome binding sites. Vectors can include introns, such as intron II of rabbit β-globin gene and the SV40 splice elements.

Suitable nucleic acid vectors also include a selectable or amplifiable marker gene and means for amplifying the copy number of the gene of interest. Nucleic acid vectors can also comprise stabilizing sequences (such as ori- or ARS-like sequences and telomere-like sequences), or can alternatively be designed to favor directed or non-directed integration into the host cell genome.

Expression vectors can be either constitutive or inducible. Inducible vectors include either naturally inducible promoters, such as the trc promoter, which is regulated by the lac operon, and the pL promoter, which is regulated by tryptophan, the MMTV-LTR promoter, which is inducible by dexamethasone, or can contain synthetic promoters and/or additional elements that confer inducible control on adjacent promoters. Examples of inducible synthetic promoters include, but are not limited to, the hybrid Plac/ara-1 promoter and the PLtetO-1 promoter. Vectors can also be inducible because they contain hormone response elements, such as the glucocorticoid response element (GRE) and the estrogen response element (ERE), which can confer hormone inducibility where vectors are used for expression in cells having the respective hormone receptors. To reduce background levels of expression, elements responsive to ecdysone, an insect hormone, can be used instead, with coexpression of the ecdysone receptor.

In some embodiments, expression vectors can be designed to fuse the expressed polypeptide to small protein tags that facilitate purification and/or visualization. Tags that facilitate purification include a polyhistidine tag that facilitates purification of the fusion protein by immobilized metal affinity chromatography, for example using NiNTA resin (Qiagen Inc., Valencia, Calif, USA) or TALON™ resin (cobalt immobilized affinity chromatography medium, Clontech Labs, Palo Alto, Calif, USA). The fusion protein can include a chitin-binding tag and self-excising intein, permitting chitin-based purification with self-removal of the fused tag (IMPACT™ system, New England Biolabs, Inc., Beverley, Mass., USA). Alternately, the fusion protein can include a calmodulin-binding peptide tag, permitting purification by calmodulin affinity resin (Stratagene, La Jolla, Calif, USA), or a specifically excisable fragment of the biotin carboxylase carrier protein, permitting purification of in vivo biotinylated protein using an avidin resin and subsequent tag removal (Promega, Madison, Wis., USA). Alternately, the polypeptide fragments, antibodies, or antigen-binding fragments can be expressed as a fusion protein with glutathione-S-transferase, the affinity and specificity of binding to glutathione permitting purification using glutathione affinity resins, such as Glutathione-Superflow Resin (Clontech Laboratories, Palo Alto, Calif, USA), with subsequent elution with free glutathione. Other tags include, but are not limited to, the Xpress epitope, detectable by anti-Xpress antibody (Invitrogen, Carlsbad, Calif, USA), a myc tag, detectable by anti-myc tag antibody, the V5 epitope, detectable by anti-V5 antibody (Invitrogen, Carlsbad, Calif, USA), FLAG® epitope, detectable by anti-FLAG® antibody (Stratagene, La Jolla, Calif, USA), and the HA epitope.

For secretion of expressed proteins, vectors can include appropriate sequences that encode secretion signals, such as leader peptides. For example, the pSecTag2 vectors (Invitrogen, Carlsbad, Calif, USA) are 5.2 kb mammalian expression vectors that carry the secretion signal from the V-J2-C region of the mouse Ig kappa-chain for efficient secretion of recombinant proteins from a variety of mammalian cell lines.

Expression vectors can also be designed to fuse proteins encoded by the heterologous nucleic acid insert to polypeptides that are larger than purification and/or identification tags. Useful fusion proteins include those that permit display of the encoded protein on the surface of a phage or cell, fusion to intrinsically fluorescent proteins, such as those that have a green fluorescent protein (GFP)-like chromophore, fusions to the IgG Fc region, and fusion proteins for use in two hybrid systems.

Vectors for phage display fuse the encoded polypeptide to, for example, the gene III protein (pIII) or gene VIII protein (pVIII) for display on the surface of filamentous phage, such as M13. Vectors for yeast display, such as the pYD1 yeast display vector (Invitrogen, Carlsbad, Calif, USA), use the agglutinin yeast adhesion receptor to display recombinant protein on the surface of *S. cerevisiae*. Vectors for mammalian display, such as the pDisplay™ vector (Invitrogen, Carlsbad, Calif, USA) target recombinant proteins using an N-terminal cell surface targeting signal and a C-terminal transmembrane anchoring domain of platelet derived growth factor receptor.

A variety of vectors that fuse proteins encoded by heterologous nucleic acids to the chromophore of the substrate-independent, intrinsically fluorescent green fluorescent protein from *Aequorea victoria* ("GFP") and its variants are available. The GFP-like chromophore can be selected from GFP-like chromophores found in naturally occurring proteins, such as *A. victoria* GFP (GenBank accession number AAA27721), *Renilla reniformis* GFP, FP583 (GenBank accession no. AF168419) (DsRed), FP593 (AF27271 1), FP483 (AF168420), FP484 (AF168424), FP595 (AF246709), FP486 (AF168421), FP538 (AF168423), and FP506 (AF168422), and need include only so much of the native protein as is needed to retain the chromophore's intrinsic fluorescence. Methods for determining the minimal domain required for fluorescence are described in, for example, Li et al., J. Biol. Chem., 1997, 272, 28545-28549. Alternately, the GFP-like chromophore can be selected from GFP-like chromophores modified from those found in nature. The methods for engineering such modified GFP-like chromophores and testing them for fluorescence activity, both alone and as part of protein fusions, are described in, for example, Heim et al., Curr. Biol., 1996, 6, 178-182 and Palm et al., Methods Enzymol., 1999, 302, 378-394. Modified chromophores can readily be used in the fusion proteins including, but not limited to, enhanced GFP ("EGFP"), enhanced blue fluorescent protein ("EBFP"), BFP2, enhanced yellow fluorescent protein ("EYFP"), enhanced cyan fluorescent protein ("ECFP") or Citrine. Vectors containing these blue-shifted variants are available from Clontech Labs (Palo Alto, Calif, USA). Vectors containing EYFP, ECFP, and Citrine are also available from Clontech Labs.

Replication incompetent retroviral vectors, typically derived from Moloney murine leukemia virus, also are useful for creating stable transfectants having integrated provirus. The highly efficient transduction machinery of retroviruses, coupled with the availability of a variety of packaging cell lines such as RetroPack™ PT 67, Eco-Pack2™-293, AmphoPack-293, and GP2-293 cell lines (all available from Clontech Laboratories, Palo Alto, Calif, USA), allow a wide host range to be infected with high efficiency; varying the multiplicity of infection readily adjusts the copy number of the integrated provirus.

The present disclosure also provides host cells comprising the nucleic acid molecules encoding any of the NetG1 polypeptides or NGL-1 polypeptides described herein. In some embodiments, the nucleic acid molecule is functionally linked to a promoter active in the host cell.

The present disclosure also provides host cells comprising the vectors comprising the nucleic acid molecules encoding any of the NetG1 polypeptides or NGL-1 polypeptides described herein.

In some embodiments, prokaryotic cells can be used with an appropriate vector. In some embodiments, the prokaryotic host cell is E. coli, Pseudomonas, Bacillus, or Streptomyces. In some embodiments, bacterial host cells are used to express the nucleic acid molecules. Useful expression vectors for bacterial hosts include bacterial plasmids, such as those from E. coli, Bacillus, or Streptomyces, including, but are not limited to, pBluescript, pGEX-2T, pUC vectors, col E1, pCR1, pBR322, pMB9 and their derivatives, RP4, phage DNAs, such as the numerous derivatives of phage lambda, such as NM989, λGT10, and λGT11, and other phages, such as M13 and filamentous single-stranded phage DNA.

In some embodiments, eukaryotic host cells, such as yeast, insect, mammalian or plant cells, can be used. Vectors for use in yeast can contain an origin of replication suitable for use in yeast and a selectable marker that is functional in yeast. Yeast vectors include, but are not limited to, Yeast Integrating plasmids (such as YIp5) and Yeast Replicating plasmids (the YRp and YEp series plasmids), Yeast Centromere plasmids (the YCp series plasmids), Yeast Artificial Chromosomes (YACs) which are based on yeast linear plasmids, denoted YLp, pGPD-2, 2μ plasmids and derivatives thereof, and improved shuttle vectors such as YIplac, YEplac and YCplac. Selectable markers in yeast vectors include a variety of auxotrophic markers, the most common of which are (in Saccharomyces cerevisiae) URA3, HIS3, LEU2, TRP1 and LYS2, which complement specific auxotrophic mutations, such as ura3-52, his3-D1, leu2-D1, trp1-D1 and lys2-201.

Insect cells are often chosen for high efficiency protein expression. Where the host cells are from Spodoptera frugiperda, such as Sf9 and Sf21 cell lines, and expresSF™ cells (Protein Sciences Corp., Meriden, Conn., USA)), the vector replicative strategy is typically based upon the baculovirus life cycle. Typically, baculovirus transfer vectors are used to replace the wild-type AcMNPV polyhedrin gene with a heterologous gene of interest. Sequences that flank the polyhedrin gene in the wild-type genome are positioned 5' and 3' of the expression cassette on the transfer vectors. Following co-transfection with AcMNPV DNA, a homologous recombination event occurs between these sequences resulting in a recombinant virus carrying the gene of interest and the polyhedrin or p10 promoter. Selection can be based upon visual screening for lacZ fusion activity.

In some embodiments, the host cells can be mammalian cells, which are particularly useful for expression of proteins intended as pharmaceutical agents, and for screening of potential agonists and antagonists of a protein or a physiological pathway. Mammalian vectors can include a viral origin, such as the SV40 origin (for replication in cell lines expressing the large T-antigen, such as COSI and COS7 cells), the papillomavirus origin, or the EBV origin for long term episomal replication (for use, such as in 293-EBNA cells, which constitutively express the EBV EBNA-1 gene product and adenovirus E1A). Vectors based upon viruses, such as adenovirus, adeno-associated virus, vaccinia virus, and various mammalian retroviruses, will typically replicate according to the viral replicative strategy. Selectable markers for use in mammalian cells include, but are not limited to, resistance to neomycin (G418), blasticidin, hygromycin and to zeocin, and selection based upon the purine salvage pathway using HAT medium.

Expression in mammalian cells can be achieved using a variety of plasmids, including, but not limited to, pSV2, pBC12BI, and p91023, as well as lytic virus vectors (such as vaccinia virus, adeno virus, and baculovirus), episomal virus vectors (such as bovine papillomavirus), and retroviral vectors (such as murine retroviruses). Useful vectors for insect cells include, but are not limited to, baculoviral vectors and pVL 941.

Plant cells can also be used for expression, with the vector replicon typically derived from a plant virus (such as cauliflower mosaic virus, CaMV; tobacco mosaic virus, TMV) and selectable markers chosen for suitability in plants.

In some embodiments, the nucleic acid molecules can be codon optimized. The codons of the nucleic acid molecules can be modified to resemble, as much as possible, genes naturally contained within the host cell without altering the amino acid sequence encoded by the nucleic acid molecule.

The present disclosure also provides compositions comprising any of the NetG1 polypeptides or NGL-1 polypeptides described herein, and a pharmaceutically acceptable carrier.

The present disclosure also provides isolated antibodies, or antigen-binding fragments thereof, that bind to any of the isolated NetG1 polypeptides or NGL-1 polypeptides described herein. In some embodiments, the isolated NetG1 polypeptide or NGL-1 polypeptide comprises up to 20 amino acids, up to 21 amino acids, up to 22 amino acids, up to 23 amino acids, or up to 24 amino acids. In some embodiments, the isolated NetG1 polypeptide or NGL-1 polypeptide comprises up to 20 amino acids. In some embodiments, the isolated NetG1 polypeptide or NGL-1 polypeptide comprises up to 21 amino acids. In some embodiments, the isolated NetG1 polypeptide or NGL-1 polypeptide comprises up to 22 amino acids. In some embodiments, the isolated NetG1 polypeptide or NGL-1 polypeptide comprises up to 23 amino acids. In some embodiments, the isolated NetG1 polypeptide or NGL-1 polypeptide comprises up to 24 amino acids. The additional amino acids (compared to the specific amino acid sequences listed below) can be inserted at the amino terminus, the carboxy terminus, or both. For example, an isolated NetG1 polypeptide that comprises up to 20 amino acids and also comprises a specific amino acid sequence that consists of 16 amino acids (e.g., SEQ ID NO:3), can have all or any number of the additional four amino acids inserted at the amino terminus, the carboxy terminus, or both. For instance, all four additional amino acids can be inserted at the amino terminus or the carboxy terminus, three amino acids can be inserted at the amino terminus and one amino acid inserted at the carboxy terminus, three amino acids can be inserted at the carboxy terminus and one amino acid inserted at the amino terminus, or two amino acids can be inserted at the amino terminus and two amino acids inserted at the carboxy terminus. Also, for example, an isolated NGL-1 polypeptide that comprises up to 20 amino acids and also comprises a specific amino acid sequence that consists of 14 amino acids (e.g., SEQ ID NO:11), can have all or any number of the additional six amino acids inserted at the amino terminus, the carboxy terminus, or both. For instance, all six additional amino acids can be inserted at the amino terminus or the carboxy terminus, five amino acids can be inserted at the amino terminus and one amino acid inserted at the carboxy terminus, five amino acids can be inserted at the carboxy terminus and one amino acid inserted at the amino terminus, four amino acids can be inserted at the amino terminus and two amino acids inserted at the carboxy terminus, four amino acids can be inserted at the carboxy terminus and two amino acids inserted at the amino terminus, or three amino acids can be inserted at the amino terminus and three amino acids inserted at the carboxy terminus.

In some embodiments, the isolated antibodies, or antigen-binding fragments thereof, can bind to an isolated NetG1 polypeptide that comprises up to 20 amino acids and comprises: TFCAMGNPYMCNNE (SEQ ID NO:1), TFSAMGNPYMCNNE (SEQ ID NO: 16), TFCAMGNPYMSNNE (SEQ ID NO:17), TFSAMGNPYMSNNE (SEQ ID NO:18), GNPYMCNNE (SEQ ID NO:2), GNPYMSNNE (SEQ ID NO:19), AVGE-IFVDELHLARYF (SEQ ID NO:3), VGEIFV (SEQ ID NO:4), EYSTGYTTNSK (SEQ ID NO:5), STGYTT (SEQ ID NO: 6), ATDCLDAFH MDP (SEQ ID NO:7), ATD-SLDAFHMDP (SEQ ID NO:20), ATDCLDAFH (SEQ ID NO:8), ATDSLDAFH (SEQ ID NO:21), TFCAMGNPTMCNNE (SEQ ID NO: 9), TFSAMGNPTMC NNE (SEQ ID NO:22), TFCAMGNPTMSNNE (SEQ ID NO:23), TFSAMGNPTMSNNE (SEQ ID NO:24), GNPTMCNNE (SEQ ID NO: 10), GNPTMSNNE (SEQ ID NO:25), NPYMCNNE (SEQ ID NO:14), NPYMSNNE (SEQ ID NO:26), NPTMCNNE (SEQ ID NO:15); or NPTMS NNE (SEQ ID NO:27). In some embodiments, the isolated antibodies, or antigen-binding fragments thereof, can bind to an isolated NetG1 polypeptide that comprises up to 20 amino acids and comprises TFCAMGNPYMCNNE (SEQ ID NO: 1). In some embodiments, the isolated antibodies, or antigen-binding fragments thereof, can bind to an isolated NetG1 polypeptide that comprises up to 20 amino acids and comprises TFSAMGNPYMCNNE (SEQ ID NO:16). In some embodiments, the isolated antibodies, or antigen-binding fragments thereof, can bind to an isolated NetG1 polypeptide that comprises up to 20 amino acids and comprises TFCAMGNPYMSNNE (SEQ ID NO:17). In some embodiments, the isolated antibodies, or antigen-binding fragments thereof, can bind to an isolated NetG1 polypeptide that comprises up to 20 amino acids and comprises TFSAMGNPYMSNNE (SEQ ID NO:18). In some embodiments, the isolated antibodies, or antigen-binding fragments thereof, can bind to an isolated NetG1 polypeptide that comprises up to 20 amino acids and comprises GNPYMCNNE (SEQ ID NO:2). In some embodiments, the isolated antibodies, or antigen-binding fragments thereof, can bind to an isolated NetG1 polypeptide that comprises up to 20 amino acids and comprises GNPYMSNNE (SEQ ID NO: 19). In some embodiments, the isolated antibodies, or antigen-binding fragments thereof, can bind to an isolated NetG1 polypeptide that comprises up to 20 amino acids and comprises AVGEIFVDELHLARYF (SEQ ID NO:3). In some embodiments, the isolated antibodies, or antigen-binding fragments thereof, can bind to an isolated NetG1 polypeptide that comprises up to 20 amino acids and comprises VGEIFV (SEQ ID NO:4). In some embodiments, the isolated antibodies, or antigen-binding fragments thereof, can bind to an isolated NetG1 polypeptide that comprises up to 20 amino acids and comprises EYSTGYTTNSK (SEQ ID NO:5). In some embodiments, the isolated antibodies, or antigen-binding fragments thereof, can bind to an isolated NetG1 polypeptide that comprises up to 20 amino acids and comprises STGYTT (SEQ ID NO: 6). In some embodiments, the isolated antibodies, or antigen-binding fragments thereof, can bind to an isolated NetG1 polypeptide that comprises up to 20 amino acids and comprises ATD-CLDAFHMDP (SEQ ID NO:7). In some embodiments, the isolated antibodies, or antigen-binding fragments thereof, can bind to an isolated NetG1 polypeptide that comprises up to 20 amino acids and comprises ATDSLDAFHMDP (SEQ ID NO:20). In some embodiments, the isolated antibodies, or antigen-binding fragments thereof, can bind to an isolated NetG1 polypeptide that comprises up to 20 amino acids and comprises ATDCLDAFH (SEQ ID NO:8). In some embodiments, the isolated antibodies, or antigen-binding fragments thereof, can bind to an isolated NetG1 polypeptide that comprises up to 20 amino acids and comprises ATD-SLDAFH (SEQ ID NO:21). In some embodiments, the isolated antibodies, or antigen-binding fragments thereof, can bind to an isolated NetG1 polypeptide that comprises up to 20 amino acids and comprises TFCAMGNPTMCNNE (SEQ ID NO:9). In some embodiments, the isolated antibodies, or antigen-binding fragments thereof, can bind to an isolated NetG1 polypeptide that comprises up to 20 amino acids and comprises TFSAMGNPTMCNNE (SEQ ID NO: 22). In some embodiments, the isolated antibodies, or antigen-binding fragments thereof, can bind to an isolated NetG1 polypeptide that comprises up to 20 amino acids and comprises TFCAMGNPTMSNNE (SEQ ID NO:23). In some embodiments, the isolated antibodies, or antigen-binding fragments thereof, can bind to an isolated NetG1 polypeptide that comprises up to 20 amino acids and comprises TFSAMGNPTMSNNE (SEQ ID NO:24). In some embodiments, the isolated antibodies, or antigen-binding fragments thereof, can bind to an isolated NetG1 polypeptide that comprises up to 20 amino acids and comprises GNPTMCNNE (SEQ ID NO:10). In some embodiments, the isolated antibodies, or antigen-binding fragments thereof, can bind to an isolated NetG1 polypeptide that comprises up to 20 amino acids and comprises GNPTMSNNE (SEQ ID NO:25). In some embodiments, the isolated antibodies, or antigen-binding fragments thereof, can bind to an isolated NetG1 polypeptide that comprises up to 20 amino acids and comprises NPYMCNNE (SEQ ID NO: 14). In some embodiments, the isolated antibodies, or antigen-binding fragments thereof, can bind to an isolated NetG1 polypeptide that comprises up to 20 amino acids and comprises NPYMSNNE (SEQ ID NO:26). In some embodiments, the isolated antibodies, or antigen-binding fragments thereof, can bind to an isolated NetG1 polypeptide that comprises up to 20 amino acids and comprises NPTMCNNE (SEQ ID NO:15). In some embodiments, the isolated antibodies, or antigen-binding fragments thereof, can bind to an isolated NetG1 polypeptide that comprises up to 20 amino acids and comprises NPTMSNNE (SEQ ID NO:27).

In some embodiments, the isolated antibodies, or antigen-binding fragments thereof, can bind to an isolated NGL-1 polypeptide that comprises up to 20 amino acids and comprises: VCSCSNQFSKVICV (SEQ ID NO:11), VSSCSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSSCSNQFSKVISV (SEQ ID NO:32), VCSSSNQFSKVISV (SEQ ID NO:33), or VSSSSNQFSKVISV (SEQ ID NO:34). In some embodiments, the isolated antibodies, or antigen-binding fragments thereof, can bind to an isolated NGL-1 polypeptide that comprises up to 20 amino acids and comprises VCSCSNQFSKVICV (SEQ ID NO:11). In some embodiments, the isolated antibodies, or antigen-binding fragments thereof, can bind to an isolated NGL-1 polypeptide that comprises up to 20 amino acids and comprises VSSCSNQFSKVICV (SEQ ID NO:28). In some embodiments, the isolated antibodies, or antigen-binding fragments thereof, can bind to an isolated NGL-1 polypeptide that comprises up to 20 amino acids and comprises VCSSSNQFSKVICV (SEQ ID NO: 29). In some embodiments, the isolated antibodies, or antigen-binding fragments thereof, can bind to an isolated NGL-1 polypeptide that comprises up to 20 amino acids and comprises VCSCSNQFSKVISV (SEQ ID NO:30). In some embodiments, the isolated antibodies, or antigen-binding fragments thereof, can bind to an isolated NGL-1 polypeptide that comprises up to 20 amino acids and comprises VSSSSNQFSKVICV (SEQ ID NO:31). In some embodiments, the isolated antibodies, or antigen-binding fragments thereof, can bind to an isolated NGL-1 polypeptide that comprises up to 20 amino acids and comprises VSSCSNQFSKVISV (SEQ ID NO: 32). In some embodiments, the isolated antibodies, or antigen-binding fragments thereof, can bind to an isolated NGL-1 polypeptide that comprises up to 20 amino acids and comprises VCSSSNQFSKVISV (SEQ ID NO:33). In some embodiments, the isolated antibodies, or antigen-binding fragments thereof, can bind to an isolated NGL-1 polypeptide that comprises up to 20 amino acids and comprises VSSSSNQFSKVISV (SEQ ID NO:34). In some embodiments, the isolated NetG1 polypeptide or NGL-1 polypeptide further comprises zero, one, two, three, or four conservative amino acid substitutions. In some embodiments, the isolated NetG1 polypeptide or NGL-1 polypeptide further comprises zero, one, two, or three conservative amino acid substitutions. In some embodiments, the NetG1 polypeptide or NGL-1 polypeptide further comprises zero, one, or two conservative amino acid substitutions. In some embodiments, the isolated NetG1 polypeptide or NGL-1 polypeptide further comprises zero or one conservative amino acid substitutions. In some embodiments, the isolated NetG1 polypeptide or NGL-1 polypeptide further comprises one conservative amino acid substitution. In some embodiments, the isolated NetG1 polypeptide or NGL-1 polypeptide further comprises two conservative amino acid substitutions. In some embodiments, the isolated NetG1 polypeptide or NGL-1 polypeptide further comprises three conservative amino acid substitutions. In some embodiments, the isolated NetG1 polypeptide or NGL-1 polypeptide further comprises four conservative amino acid substitutions.

In some embodiments, the isolated antibodies, or antigen-binding fragments thereof, can bind to an isolated NetG1 polypeptide that comprises up to 18 amino acids and comprises TFCAMGNPYMCNNE (SEQ ID NO:1). In some embodiments, the isolated antibodies, or antigen-binding fragments thereof, can bind to an isolated NetG1 polypeptide that comprises up to 18 amino acids and comprises TFSAMGNPYMCNNE (SEQ ID NO:16). In some embodiments, the isolated antibodies, or antigen-binding fragments thereof, can bind to an isolated NetG1 polypeptide that comprises up to 18 amino acids and comprises TFCAMGNPYMSNNE (SEQ ID NO:17). In some embodiments, the isolated antibodies, or antigen-binding fragments thereof, can bind to an isolated NetG1 polypeptide that comprises up to 18 amino acids and comprises TFSAMGNPYMSNNE (SEQ ID NO:18). In some embodiments, the isolated antibodies, or antigen-binding fragments thereof, can bind to an isolated NetG1 polypeptide that comprises up to 13 amino acids and comprises GNPYMCNNE (SEQ ID NO:2). In some embodiments, the isolated antibodies, or antigen-binding fragments thereof, can bind to an isolated NetG1 polypeptide that comprises up to 13 amino acids and comprises GNPYMSNNE (SEQ ID NO:19). In some embodiments, the isolated antibodies, or antigen-binding fragments thereof, can bind to an isolated NetG1 polypeptide that comprises up to 20 amino acids and comprises AVGEIFVDELHLARYF (SEQ ID NO:3). In some embodiments, the isolated antibodies, or antigen-binding fragments thereof, can bind to an isolated NetG1 polypeptide that comprises up to 10 amino acids and comprises VGEIFV (SEQ ID NO: 4). In some embodiments, the isolated antibodies, or antigen-binding fragments thereof, can bind to an isolated NetG1 polypeptide that comprises up to 15 amino acids and comprises EYSTGYTTNSK (SEQ ID NO:5). In some embodiments, the isolated antibodies, or antigen-binding fragments thereof, can bind to an isolated NetG1 polypeptide that comprises up to 10 amino acids and comprises STGYTT (SEQ ID NO:6). In some embodiments, the isolated antibodies, or antigen-binding fragments thereof, can bind to an isolated NetG1 polypeptide that comprises up to 16 amino acids and comprises ATDCLDAFHMDP (SEQ ID NO:7). In some embodiments, the isolated antibodies, or antigen-binding fragments thereof, can bind to an isolated NetG1 polypeptide that comprises up to 16 amino acids and comprises ATDSLDAFHMDP (SEQ ID NO:20). In some embodiments, the isolated antibodies, or antigen-binding fragments thereof, can bind to an isolated NetG1 polypeptide that comprises up to 13 amino acids and comprises ATDCLDAFH (SEQ ID NO:8). In some embodiments, the isolated antibodies, or antigen-binding fragments thereof, can bind to an isolated NetG1 polypeptide that comprises up to 13 amino acids and comprises ATDSLDAFH (SEQ ID NO:21). In some embodiments, the isolated antibodies, or antigen-binding fragments thereof, can bind to an isolated NetG1 polypeptide that comprises up to 18 amino acids and comprises TFCAMGNPTMCNNE (SEQ ID NO:9). In some embodiments, the isolated antibodies, or antigen-binding fragments thereof, can bind to an isolated NetG1 polypeptide that comprises up to 18 amino acids and comprises TFSAMGNPTMCNNE (SEQ ID NO:22). In some embodiments, the isolated antibodies, or antigen-binding fragments thereof, can bind to an isolated NetG1 polypeptide that comprises up to 18 amino acids and comprises TFCAMGNPTMSNNE (SEQ ID NO:23). In some embodiments, the isolated antibodies, or antigen-binding fragments thereof, can bind to an isolated NetG1 polypeptide that comprises up to 18 amino acids and comprises TFSAMGNPTMSNNE (SEQ ID NO:24). In some embodiments, the isolated antibodies, or antigen-binding fragments thereof, can bind to an isolated NetG1 polypeptide that comprises up to 13 amino acids and comprises GNPTMCNNE (SEQ ID NO:10). In some embodiments, the isolated antibodies, or antigen-binding fragments thereof, can bind to an isolated NetG1 polypeptide that comprises up to 13 amino acids and comprises GNPTMSNNE (SEQ ID NO:25). In some embodiments, the isolated antibodies, or antigen-binding fragments thereof, can bind to an isolated NetG1 polypeptide that comprises up to 12 amino acids and comprises NPYMCNNE (SEQ ID NO: 14). In some embodiments, the isolated antibodies, or antigen-binding fragments thereof, can bind to an isolated NetG1 polypeptide that comprises up to 12 amino acids and comprises NPYMSNNE (SEQ ID NO:26). In some embodiments, the isolated antibodies, or antigen-binding fragments thereof, can bind to an isolated NetG1 polypeptide that comprises up to 12 amino acids and comprises NPTMCNNE (SEQ ID NO:15). In some embodiments, the isolated antibodies, or antigen-binding fragments thereof, can bind to an isolated NetG1 polypeptide that comprises up to 12 amino acids and comprises NPTMSNNE (SEQ ID NO:27).

In some embodiments, the isolated antibodies, or antigen-binding fragments thereof, can bind to an isolated NetG1 polypeptide that comprises up to 18 amino acids and comprises: VCSCSNQFSKVICV (SEQ ID NO:11), VSSCSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSSCSNQFSKVISV (SEQ ID NO:32), VCSSSNQFSKVISV (SEQ ID NO:33), or VSSSSNQFSKVISV (SEQ ID NO:34). In some embodiments, the isolated antibodies, or antigen-binding fragments thereof, can bind to an isolated NetG1 polypeptide that comprises up to 18 amino acids and comprises VCSCSNQFSKVICV (SEQ ID NO:11). In some embodiments, the isolated antibodies, or antigen-binding fragments thereof, can bind to an isolated NetG1 polypeptide that comprises up to 18 amino acids and comprises VSSCSNQFSKVICV (SEQ ID NO:28). In some embodiments, the isolated antibodies, or antigen-binding fragments thereof, can bind to an isolated NetG1 polypeptide that comprises up to 18 amino acids and comprises VCSSSNQFSKVICV (SEQ ID NO: 29). In some embodiments, the isolated antibodies, or antigen-binding fragments thereof, can bind to an isolated NetG1 polypeptide that comprises up to 18 amino acids and comprises VCSCSNQFSKVISV (SEQ ID NO:30). In some embodiments, the isolated antibodies, or antigen-binding fragments thereof, can bind to an isolated NetG1 polypeptide that comprises up to 18 amino acids and comprises VSSSSNQFSKVICV (SEQ ID NO:31). In some embodiments, the isolated antibodies, or antigen-binding fragments thereof, can bind to an isolated NetG1 polypeptide that comprises up to 18 amino acids and comprises VSSCSNQFSKVISV (SEQ ID NO: 32). In some embodiments, the isolated antibodies, or antigen-binding fragments thereof, can bind to an isolated NetG1 polypeptide that comprises up to 18 amino acids and comprises VCSSSNQFSKVISV (SEQ ID NO:33). In some embodiments, the isolated antibodies, or antigen-binding fragments thereof, can bind to an isolated NetG1 polypeptide that comprises up to 18 amino acids and comprises VSSSSNQFSKVISV (SEQ ID NO:34). In some embodiments, the isolated NetG1 polypeptide or NGL-1 polypeptide further comprises zero, one, two, three, or four conservative amino acid substitutions. In some embodiments, the isolated NetG1 polypeptide or NGL-1 polypeptide further comprises zero, one, two, or three conservative amino acid substitutions. In some embodiments, the NetG1 polypeptide or NGL-1 polypeptide further comprises zero, one, or two conservative amino acid substitutions. In some embodiments, the isolated NetG1 polypeptide or NGL-1 polypeptide further comprises zero or one conservative amino acid substitutions. In some embodiments, the isolated NetG1 polypeptide or NGL-1 polypeptide further comprises one conservative amino acid substitution. In some embodiments, the isolated NetG1 polypeptide or NGL-1 polypeptide further comprises two conservative amino acid substitutions. In some embodiments, the isolated NetG1 polypeptide or NGL-1 polypeptide further comprises three conservative amino acid substitutions. In some embodiments, the isolated NetG1 polypeptide or NGL-1 polypeptide further comprises four conservative amino acid substitutions.

In some embodiments, the isolated antibodies, or antigen-binding fragments thereof, can bind to an isolated NetG1 polypeptide that consists of SEQ ID NO:1, SEQ ID NO:16, SEQ ID NO: 17, SEQ ID NO: 18, SEQ ID NO:2, SEQ ID NO: 19, SEQ ID NO:3, SEQ ID NO:4, SEQ ID NO: 5, SEQ ID NO:6, SEQ ID NO:7, SEQ ID NO:20, SEQ ID NO:8, SEQ ID NO:21, SEQ ID NO: 9, SEQ ID NO:22, SEQ ID NO:23, SEQ ID NO:24, SEQ ID NO: 10, SEQ ID NO:25, SEQ ID NO: 14, SEQ ID NO:26, SEQ ID NO: 15, or SEQ ID NO:27. In some embodiments, the isolated antibodies, or antigen-binding fragments thereof, can bind to an isolated NetG1 polypeptide that consists of SEQ ID NO:1. In some embodiments, the isolated antibodies, or antigen-binding fragments thereof, can bind to an isolated NetG1 polypeptide that consists of SEQ ID NO: 16. In some embodiments, the isolated antibodies, or antigen-binding fragments thereof, can bind to an isolated NetG1 polypeptide that consists of SEQ ID NO:17. In some embodiments, the isolated antibodies, or antigen-binding fragments thereof, can bind to an isolated NetG1 polypeptide that consists of SEQ ID NO: 18. In some embodiments, the isolated antibodies, or antigen-binding fragments thereof, can bind to an isolated NetG1 polypeptide that consists of SEQ ID NO:2. In some embodiments, the isolated antibodies, or antigen-binding fragments thereof, can bind to an isolated NetG1 polypeptide that consists of SEQ ID NO: 19. In some embodiments, the isolated antibodies, or antigen-binding fragments thereof, can bind to an isolated NetG1 polypeptide that consists of SEQ ID NO:3. In some embodiments, the isolated antibodies, or antigen-binding fragments thereof, can bind to an isolated NetG1 polypeptide that consists of SEQ ID NO:4. In some embodiments, the isolated antibodies, or antigen-binding fragments thereof, can bind to an isolated NetG1 polypeptide that consists of SEQ ID NO:5. In some embodiments, the isolated antibodies, or antigen-binding fragments thereof, can bind to an isolated NetG1 polypeptide that consists of SEQ ID NO:6. In some embodiments, the isolated antibodies, or antigen-binding fragments thereof, can bind to an isolated NetG1 polypeptide that consists of SEQ ID NO:7. In some embodiments, the isolated antibodies, or antigen-binding fragments thereof, can bind to an isolated NetG1 polypeptide that consists of SEQ ID NO:20. In some embodiments, the isolated antibodies, or antigen-binding fragments thereof, can bind to an isolated NetG1 polypeptide that consists of SEQ ID NO:8. In some embodiments, the isolated antibodies, or antigen-binding fragments thereof, can bind to an isolated NetG1 polypeptide that consists of SEQ ID NO:21. In some embodiments, the isolated antibodies, or antigen-binding fragments thereof, can bind to an isolated NetG1 polypeptide that consists of SEQ ID NO:9. In some embodiments, the isolated antibodies, or antigen-binding fragments thereof, can bind to an isolated NetG1 polypeptide that consists of SEQ ID NO:22. In some embodiments, the isolated antibodies, or antigen-binding fragments thereof, can bind to an isolated NetG1 polypeptide that consists of SEQ ID NO:23. In some embodiments, the isolated antibodies, or antigen-binding fragments thereof, can bind to an isolated NetG1 polypeptide that consists of SEQ ID NO:24. In some embodiments, the isolated antibodies, or antigen-binding fragments thereof, can bind to an isolated NetG1 polypeptide that consists of SEQ ID NO:10. In some embodiments, the isolated antibodies, or antigen-binding fragments thereof, can bind to an isolated NetG1 polypeptide that consists of SEQ ID NO:25. In some embodiments, the isolated antibodies, or antigen-binding fragments thereof, can bind to an isolated NetG1 polypeptide that consists of SEQ ID NO: 14. In some embodiments, the isolated antibodies, or antigen-binding fragments thereof, can bind to an isolated NetG1 polypeptide that consists of SEQ ID NO:26. In some embodiments, the isolated antibodies, or antigen-binding fragments thereof, can bind to an isolated NetG1 polypeptide that consists of SEQ ID NO:15. In some embodiments, the isolated antibodies, or antigen-binding fragments thereof, can bind to an isolated NetG1 polypeptide that consists of SEQ ID NO:27.

In some embodiments, the isolated antibodies, or antigen-binding fragments thereof, can bind to an isolated NGL-1 polypeptide that consists of SEQ ID NO: 11, SEQ ID NO:28, SEQ ID NO: 29, SEQ ID NO:30, SEQ ID NO:31, SEQ ID NO:32, SEQ ID NO:33, or SEQ ID NO:34. In some embodiments, the isolated antibodies, or antigen-binding fragments thereof, can bind to an isolated NGL-1 polypeptide that consists of SEQ ID NO:11. In some embodiments, the isolated antibodies, or antigen-binding fragments thereof, can bind to an isolated NGL-1 polypeptide that consists of SEQ ID NO:28. In some embodiments, the isolated antibodies, or antigen-binding fragments thereof, can bind to an isolated NGL-1 polypeptide that consists of SEQ ID NO:29. In some embodiments, the isolated antibodies, or antigen-binding fragments thereof, can bind to an isolated NGL-1 polypeptide that consists of SEQ ID NO:30. In some embodiments, the isolated antibodies, or antigen-binding fragments thereof, can bind to an isolated NGL-1 polypeptide that consists of SEQ ID NO:31. In some embodiments, the isolated antibodies, or antigen-binding fragments thereof, can bind to an isolated NGL-1 polypeptide that consists of SEQ ID NO:32. In some embodiments, the isolated antibodies, or antigen-binding fragments thereof, can bind to an isolated NGL-1 polypeptide that consists of SEQ ID NO:33. In some embodiments, the isolated antibodies, or antigen-binding fragments thereof, can bind to an isolated NGL-1 polypeptide that consists of SEQ ID NO:34. In some embodiments, the isolated NetG1 polypeptide or NGL-1 polypeptide further comprises zero, one, two, three, or four conservative amino acid substitutions. In some embodiments, the isolated NetG1 polypeptide or NGL-1 polypeptide further comprises zero, one, two, or three conservative amino acid substitutions. In some embodiments, the NetG1 polypeptide or NGL-1 polypeptide further comprises zero, one, or two conservative amino acid substitutions. In some embodiments, the isolated NetG1 polypeptide or NGL-1 polypeptide further comprises zero or one conservative amino acid substitutions. In some embodiments, the isolated NetG1 polypeptide or NGL-1 polypeptide further comprises one conservative amino acid substitution. In some embodiments, the isolated NetG1 polypeptide or NGL-1 polypeptide further comprises two conservative amino acid substitutions. In some embodiments, the isolated NetG1 polypeptide or NGL-1 polypeptide further comprises three conservative amino acid substitutions. In some embodiments, the isolated NetG1 polypeptide or NGL-1 polypeptide further comprises four conservative amino acid substitutions.

In some embodiments, the isolated antibodies, or antigen-binding fragments thereof, can bind to NetG1 polypeptides or NGL-1 polypeptides that are linked or fused to a heterologous polypeptide, such as those described herein. In some embodiments, the heterologous polypeptide is an affinity tag, a fluorescent protein, or an epitope tag, such as those described herein. In some embodiments, the isolated antibodies, or antigen-binding fragments thereof, are linked or fused to a heterologous polypeptide, such as an affinity tag, a fluorescent protein, or an epitope tag, such as those described herein.

In some embodiments, the isolated antibodies, or antigen-binding fragments thereof, can bind to NetG1 polypeptides or NGL-1 polypeptides that are labeled, as described herein. In some embodiments, the label is a fluorescent label or a radiolabel, such as those described herein. In some embodiments, the isolated antibodies, or antigen-binding fragments thereof, are labeled with, for example, a fluorescent label or a radiolabel, such as those described herein.

In some embodiments, the antibodies, or antigen-binding fragments thereof, can be modified to alter at least one constant region-mediated biological effector function. For example, in some embodiments, the antibodies can be modified to reduce at least one constant region-mediated biological effector function relative to the unmodified antibody, e.g., reduced binding to one or more of the Fc receptors (FcγR) such as FcγRI, FcγRIIA, FcγRIIB, FcγRIIIA and/or FcγRIIIB. FcγR binding can be reduced by mutating the immunoglobulin constant region segment of the antibody at particular regions necessary for FcγR interactions (see, Canfield and Morrison, J. Exp. Med., 1991, 173, 1483-1491; and Lund et al., J. Immunol., 1991, 147, 2657-2662). Reduction in FcγR binding ability of the antibody can also reduce other effector functions which rely on FcγR interactions, such as opsonization, phagocytosis and antigen-dependent cellular cytotoxicity ("ADCC").

In some embodiments, the antibodies provided herein are polyclonal antibodies. In some embodiments, the antibodies provided herein are monoclonal antibodies. Monoclonal antibodies can be made by techniques, including, for example, the hybridoma method (e.g., Kohler et al., Nature, 1975, 256, 495; Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981)), recombinant DNA methods (see, e.g., U.S. Pat. No. 4,816,567), phage display technologies (see, e.g., Clackson et al., Nature, 1991, 352, 624-628; Marks et al., J. Mol. Biol., 1991, 222, 581-597); Sidhu et al., J. Mol. Biol., 2004, 338, 299-310; Lee et al., J. Mol. Biol., 2004, 340, 1073-1093; Fellouse, Proc. Nat. Acad. Sci. USA, 2004, 101, 12467-12472; and Lee et al., J. Immunol. Methods, 2004, 284, 119-132), and technologies for producing human or human-like antibodies in animals that have parts or all of the human immunoglobulin loci or genes encoding human immunoglobulin sequences (see, e.g., PCT Publications WO 1998/24893, WO 1996/34096, WO 1996/33735, WO 1997/17852, and 1991/10741; Jakobovits et al., Proc. Natl. Acad. Sci. USA, 1993, 90, 2551; Jakobovits et al., Nature, 1993, 362, 255-258; Bruggemann et al., Year in Immuno., 1993, 7, 33; Marks et al., Bio/Technology, 1992, 10, 779-783; Lonberg et al., Nature, 1994, 368, 856-859; Morrison, Nature, 1994, 368, 812-813; Fishwild et al., Nature Biotechnology, 1996, 14, 845-851; Neuberger, Nature Biotechnology, 1996, 14, 826; Lonberg and Huszar, Intern. Rev. Immunol., 1995, 13, 65-93; and U.S. Pat. Nos. 5,545,806, 5,569,825, 5,591,669, 5,545,807, 5,625,126, 5,633,425, and 5,661,016.

In some embodiments, the isolated antibodies, or antigen-binding fragments thereof, are chimeric. In some embodiments, the chimeric antibodies, or antigen-binding fragments thereof, are primatized chimeric antibodies, or antigen-binding fragments thereof. Methods for producing primatized antibodies are disclosed in, for example, U.S. Pat. Nos. 5,658,570, 5,681,722, and 5,693,780. In some embodiments, the chimeric antibodies, or antigen-binding fragments thereof, are humanized. In some embodiments, the antibodies, or antigen-binding fragments thereof, are completely humanized. Methods for producing completely human antibodies are known in the art, including phage display methods using antibody libraries derived from human immunoglobulin sequences (see, U.S. Pat. Nos. 4,444,887 and 4,716,111; and PCT Publications WO 98/46645, WO 98/50433, WO 98/24893, WO 98/16654, WO 96/34096, WO 96/33735, and WO 91/10741). Human antibodies can also be produced using transgenic mice which are incapable of expressing functional endogenous immunoglobulins, but which can express human immunoglobulin genes (see, PCT Publications WO 98/24893, WO 92/01047, WO 96/34096, and WO 96/33735; and U.S. Pat. Nos. 5,413,923, 5,625,126, 5,633,425, 5,569,825, 5,661,016, 5,545,806, 5,814,318, 5,885,793, 5,916,771, and 5,939,598). Completely human antibodies that recognize a selected epitope can also be generated using a technique referred to as "guided selection" (see, Jespers et al., Biotechnology, 1988, 12, 899-903).

In some embodiments, the antibodies, or antigen-binding fragments thereof, are bispecific antibodies. Bispecific antibodies have binding specificities for at least two different antigens (i.e., one of the binding specificities is directed to NetG1 or NGL-1, and the other binding specificity is for any other antigen, such as a cell-surface protein, receptor, receptor subunit, tissue-specific antigen, virally derived protein, virally encoded envelope protein, bacterially derived protein, or bacterial surface protein, etc.).

In some embodiments, the antigen-binding fragments are Fab fragments, Fab' fragments, F(ab')2 fragments, an scFv, a dsFv, a ds-scFv, a dimer, a minibody, a diabody, or a multimer thereof. In some embodiments, the antigen-binding fragments are Fab fragments. In some embodiments, the antigen-binding fragments are Fab' fragments. In some embodiments, the antigen-binding fragments are F(ab')$_2$ fragments. In some embodiments, the antigen-binding fragments are an scFv. In some embodiments, the antigen-binding fragments are a dsFv. In some embodiments, the antigen-binding fragments are a ds-scFv. In some embodiments, the antigen-binding fragments are a dimer. In some embodiments, the antigen-binding fragments are a mini-body. In some embodiments, the antigen-binding fragments are a diabody.

In some embodiments, the isolated antibodies, or antigen-binding fragments thereof, are conjugated to an active agent. In some embodiments, the active agent is a radioactive molecule, a radionuclide, a sensitizer molecule, an imaging reagent, a radioisotope, a toxin, an anti-angiogenic agent, an anti-tumor agent, a chemotherapeutic agent, an immuno-modulator, a cytokine, or a reporter group.

In some embodiments, the isolated antibodies are IgA, IgD, IgE, IgG, or IgM antibodies. In some embodiments, the isolated antibodies are IgA antibodies. In some embodiments, the isolated antibodies are IgD antibodies. In some embodiments, the isolated antibodies are IgE antibodies. In some embodiments, the isolated antibodies are IgG antibodies. In some embodiments, the isolated antibodies are IgM antibodies. In some embodiments, the isolated antibodies are IgG1, IgG2, IgG3, IgG4, IgA1, or IgA2 antibodies. In some embodiments, the isolated antibodies are IgG1 antibodies. In some embodiments, the isolated antibodies are IgG2 antibodies. In some embodiments, the isolated antibodies are IgG3 antibodies. In some embodiments, the isolated antibodies are IgG4 antibodies. In some embodiments, the isolated antibodies are IgAQ1 antibodies. In some embodiments, the isolated antibodies are IgA2 antibodies.

In some embodiments, the light chain constant region of the isolated antibodies are a kappa ($\kappa$) light region or a lambda ($\lambda$) region. A $\lambda$ light region can be any one of the $\lambda_1$, $\lambda_2$, $\lambda_3$, or $\lambda_4$ subtypes. In some embodiments, the kappa light chain is the allotype Km1, Km2, or Km3.

In some embodiments, the antibodies, or antigen-binding fragments thereof, comprise three $V_H$ CDRs and three $V_L$ CDRS.

The present disclosure also provides compositions comprising any of the antibodies, or antigen-binding fragments thereof, that bind to any of the NetG1 polypeptides or NGL-1 polypeptides described herein, and a pharmaceutically acceptable carrier.

The present disclosure also provides methods of making any of the antibodies described herein that bind to a NetG1 polypeptide or NGL-1 polypeptide comprising immunizing an animal with any of the NetG1 polypeptides or NGL-1 polypeptides described herein. In some embodiments, the methods comprise immunizing an animal with a NetG1 polypeptide or NGL-1 polypeptide comprising up to 20 amino acids, wherein: the NetG1 polypeptide comprises: TFCAMGNPYMCNNE (SEQ ID NO:1), TFSAMGNPYMCNNE (SEQ ID NO:16), TFCAMGNPYMSNNE (SEQ ID NO:17), TFSAMGNPYMSNNE (SEQ ID NO:18), GNPYMCNNE (SEQ ID NO:2), GNPYMSNNE (SEQ ID NO:19), AVGE-IFVDELHLARYF (SEQ ID NO:3), VGEIFV (SEQ ID NO:4), EYSTGYTTNSK (SEQ ID NO:5), STGYTT (SEQ ID NO: 6), ATDCLDAFHMDP (SEQ ID NO:7), ATD-SLDAFHMDP (SEQ ID NO:20), ATDCLDAFH (SEQ ID NO:8), ATDSLDAFH (SEQ ID NO:21), TFCAMGNPTMCNNE (SEQ ID NO: 9), TFSAMGNPTMCNNE (SEQ ID NO:22), TFCAMGNPTMSNNE (SEQ ID NO:23), TFSAMGNPTMSNNE (SEQ ID NO:24), GNPTMCNNE (SEQ ID NO: 10), GNPTMSNNE (SEQ ID NO:25), NPYMCNNE (SEQ ID NO:14), NPYMSNNE (SEQ ID NO:26), NPTMCNNE (SEQ ID NO:15); or NPTMSNNE (SEQ ID NO:27); the NGL-1 polypeptide comprises VCSCSNQFSKVICV (SEQ ID NO:11), VSS-CSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSS-CSNQFSKVISV (SEQ ID NO:32), VCSSSNQFSKVISV (SEQ ID NO:33), or VSSSSNQFSKVISV (SEQ ID NO:34); and wherein the NetG1 polypeptide or NGL-1 polypeptide further comprises zero, one, two, three, or four conservative amino acid substitutions. In some embodiments, the methods comprise immunizing an animal with a NetG1 polypeptide consisting of: TFCAMGNPYMCNNE (SEQ ID NO:1), TFSAMGNPYMCNNE (SEQ ID NO: 16), TFCAMGNPYMSNNE (SEQ ID NO: 17), TFSAMGNPYMSNNE (SEQ ID NO: 18), GNPYMCNNE (SEQ ID NO:2), GNPYMSNNE (SEQ ID NO:19), AVGE-IFVDELHLARYF (SEQ ID NO:3), VGEIFV (SEQ ID NO:4), EYSTGYTTNSK (SEQ ID NO:5), STGYTT (SEQ ID NO:6), ATDCLDAFHMDP (SEQ ID NO: 7), ATD-SLDAFHMDP (SEQ ID NO:20), ATDCLDAFH (SEQ ID NO:8), ATDSLDAFH (SEQ ID NO:21), TFCAMGNPTMCNNE (SEQ ID NO:9), TFSAMGNPTMCNNE (SEQ ID NO: 22), TFCAMGNPTMSNNE (SEQ ID NO:23), TFSAMGNPTMSNNE (SEQ ID NO:24), GNPTMCNNE (SEQ ID NO:10), GNPTMSNNE (SEQ ID NO:25), NPYMCNNE (SEQ ID NO: 14), NPYMSNNE (SEQ ID NO:26), NPTMCNNE (SEQ ID NO: 15); or NPTMSNNE (SEQ ID NO: 27); or immunizing an animal with an NGL-1 polypeptide consisting of VCSCSNQFSKVICV (SEQ ID NO:11), VSSCSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSS-CSNQFSKVISV (SEQ ID NO:32), VCSSSNQFSKVISV (SEQ ID NO:33), or VSSSSNQFSKVISV (SEQ ID NO:34), wherein the NetG1 polypeptide or NGL-1 polypeptide further comprises zero, one, two, three, or four conservative amino acid substitutions.

In some embodiments, the methods comprise immunizing an animal with a NetG1 polypeptide consisting of: TFCAMGNPYMCNNE (SEQ ID NO:1), TFSAMGNPYMCNNE (SEQ ID NO:16), TFCAMGNPYMSNNE (SEQ ID NO:17), TFSAMGNPYMSNNE (SEQ ID NO: 18), GNPYMCNNE (SEQ ID NO:2), GNPYMSNNE (SEQ ID NO:19), AVGE-IFVDELHLARYF (SEQ ID NO:3), VGEIFV (SEQ ID NO:4), EYSTGYTTNSK (SEQ ID NO: 5), STGYTT (SEQ ID NO:6), ATDCLDAFHMDP (SEQ ID NO:7), ATD-SLDAFHMDP (SEQ ID NO:20), ATDCLDAFH (SEQ ID NO:8), ATDSLDAFH (SEQ ID NO:21), TFCAMGNPTMCNNE (SEQ ID NO:9), TFSAMGNPTMCNNE (SEQ ID NO:22), TFCAMGNPTMSNNE (SEQ ID NO:23), TFSAMGNPTMSNNE (SEQ ID NO:24), GNPTMCNNE (SEQ ID NO: 10), GNPTMSNNE (SEQ ID NO:25), NPYMCNNE (SEQ ID NO: 14), NPYMSNNE (SEQ ID NO:26), NPTMCNNE (SEQ ID NO:15); or NPTMSNNE (SEQ ID NO: 27); or immunizing an animal with an NGL-1 polypeptide consisting of VCSCSNQFSKVICV (SEQ ID NO:11), VSSCSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSS-CSNQFSKVISV (SEQ ID NO:32), VCSSSNQFSKVISV (SEQ ID NO:33), or VSSSSNQFSKVISV (SEQ ID NO:34).

Polyclonal antibodies can be raised in animals by multiple subcutaneous (sc) or intraperitoneal (ip) injections of immunogenic forms of the polypeptides which elicit an antibody response in the mammal. Techniques for conferring immunogenicity on a polypeptide include, for example, conjugation to a carrier. For example, the polypeptides can be conjugated to a protein that is immunogenic in the species to be immunized. For example, the polypeptide can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups. The progress of immunization can be monitored by detection of antibody titers in plasma or serum. Standard ELISA or other immunoassay procedures are optionally used with the immunogen as antigen to assess the levels of antibodies.

Immunization of animals can be carried out by methods such as those disclosed in, for example, Harlow and Lane, Antibodies: A Laboratory Manual, New York: Cold Spring Harbor Press, 1990. Methods for immunizing non-human animals such as mice, rats, sheep, goats, pigs, cattle and horses are disclosed in, for example, Harlow and Lane and U.S. Pat. No. 5,994,619. In some embodiments, the NetG1 or the NGL-1 polypeptide can be administered with an adjuvant to stimulate the immune response. Such adjuvants include, but are not limited to, complete or incomplete Freund's adjuvant, RIBI (muramyl dipeptides) or ISCOM (immunostimulating complexes). Such adjuvants can protect the polypeptide from rapid dispersal by sequestering it in a local deposit, or they can contain substances that stimulate the host to secrete factors that are chemotactic for macrophages and other components of the immune system.

After immunization of an animal with a NetG1 or an NGL-1 polypeptide, antibodies and/or antibody-producing cells can be obtained from the animal. An anti-NetG1 or an anti-NGL-1 antibody-containing serum can be obtained from the animal by bleeding or sacrificing the animal. The serum can be used as it is obtained from the animal, an immunoglobulin fraction may be obtained from the serum, or the anti-NetG1 or the anti-NGL-1 antibodies can be purified from the serum using standard methods such as plasmaphoresis or adsorption chromatography with IgG-specific adsorbents such as immobilized Protein A.

Monoclonal antibodies can be made using the hybridoma method described by Kohler et al., Nature, 1975, 256, 495, or can be made by recombinant DNA methods (see, U.S. Pat. No. 4,816,567). In the hybridoma method, a mouse or other appropriate host animal, such as a hamster, can be immunized to elicit lymphocytes that produce or are capable of producing antibodies that will specifically bind to the polypeptide used for immunization. Alternately, lymphocytes can be immunized in vitro. After immunization, lymphocytes can be isolated and fused with a myeloma cell line using a suitable fusing agent, such as polyethylene glycol, to form a hybridoma cell (see, Goding, Monoclonal Antibodies: Principles and Practice, pp. 59-103 (Academic Press, 1986)). The hybridoma cells are seeded and grown in a suitable culture medium which can contain one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically can include hypoxanthine, aminopterin, and thymidine (HAT medium), which substances prevent the growth of HGPRT-deficient cells.

Suitable fusion partner myeloma cells include those that fuse efficiently, support stable high-level production of antibody by the selected antibody-producing cells, and are sensitive to a selective medium that selects against the unfused parental cells. Suitable myeloma cell lines are murine myeloma lines, such as those derived from MOPC-21 and MPC-11 mouse tumors available from the Salk Institute Cell Distribution Center, San Diego, Calif. USA, and SP-2 and derivatives (X63-Ag8-653 cells) available from the American Type Culture Collection (Manassas, Va., USA). Human myeloma and mouse-human heteromyeloma cell lines also have been described for the production of human monoclonal antibodies (Kozbor, J. Immunol., 1984, 133, 3001; and Brodeur et al., Monoclonal Antibody Production Techniques and Applications, pp. 51-63 (Marcel Dekker, Inc., New York, 1987)). Culture medium in which hybridoma cells are growing can be assayed for production of monoclonal antibodies directed against the antigen. The binding specificity of monoclonal antibodies produced by hybridoma cells can be determined by immunoprecipitation or by an in vitro binding assay, such as radioimmunoassay (RIA) or enzyme-linked immunosorbent assay (ELISA).

DNA encoding the monoclonal antibodies can be isolated and sequenced using conventional procedures (e.g., by using oligonucleotide probes that are capable of binding specifically to genes encoding the heavy and light chains of murine antibodies). The hybridoma cells can serve as a source of such DNA. Once isolated, the DNA can be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells.

In some embodiments, monoclonal antibodies or antibody fragments can be isolated from antibody phage libraries generated using the techniques described in McCafferty et al., Nature, 1990, 348, 552-554. Clackson et al. (Nature, 1991, 352, 624-628) and Marks et al. (J. Mol. Biol., 1991, 222, 581-597) describe the isolation of murine and human antibodies, respectively, using phage libraries. Subsequent publications describe the production of high affinity (nM range) human antibodies by chain shuffling (Marks et al., Bio/Technology, 1992, 10, 779-783), as well as combinatorial infection and in vivo recombination as a strategy for constructing very large phage libraries (Waterhouse et al., Nuc. Acids. Res., 1993, 21, 22652266). Thus, these techniques are viable alternatives to traditional monoclonal antibody hybridoma techniques for isolation of monoclonal antibodies.

The DNA that encodes the antibody can be modified to produce chimeric or fusion antibody polypeptides, for example, by substituting human heavy chain and light chain constant domain ($C_H$ and $C_L$) sequences for the homologous murine sequences (see, U.S. Pat. No. 4,816,567; and Morrison et al., Proc. Natl. Acad. Sci. USA., 1984, 81, 6851), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen. The immunogenic peptides for immunization may be prepared using a variety of methods known to one skilled in the art.

The present disclosure also provides methods of treating a human having a cancer or any disease that includes chronic fibrosis or inflammation comprising administering to the human in need thereof any of the NetG1 polypeptides or NGL-1 polypeptides described herein. In some embodiments, the NetG1 polypeptide or NGL-1 polypeptide is present within a composition comprising a pharmaceutically acceptable carrier. In some embodiments, the cancer being treated is characterized by cancer cells, or other cells at the vicinity of the cancer cell (i.e., in the tumor microenvironment) expressing NetG1 and/or NGL-1 polypeptides.

In some embodiments, the NetG1 polypeptide comprises up to 20 amino acids and comprises: TFCAMGNPYMCNNE (SEQ ID NO:1), TFSAMGNPYMCNNE (SEQ ID NO:16), TFCAMGNPYMSNNE (SEQ ID NO: 17), TFSAMGNPYMSNNE (SEQ ID NO:18), GNPYMCNNE (SEQ ID NO:2), GNPYMSNNE (SEQ ID NO:19), AVGE-IFVDELHLARYF (SEQ ID NO:3), VGEIFV (SEQ ID NO:4), EYSTGYTTNSK (SEQ ID NO:5), STGYTT (SEQ ID NO: 6), ATDCLDAFHMDP (SEQ ID NO:7), ATD-SLDAFHMDP (SEQ ID NO:20), ATDCLDAFH (SEQ ID NO:8), ATDSLDAFH (SEQ ID NO:21), TFCAMGNPTMCNNE (SEQ ID NO: 9), TFSAMGNPTMCNNE (SEQ ID NO:22), TFCAMGNPTMSNNE (SEQ ID NO:23), TFSAMGNPTMSNNE (SEQ ID NO:24), GNPTMCNNE (SEQ ID NO: 10), GNPTMSNNE (SEQ ID NO:25), NPYMCNNE (SEQ ID NO:14), NPYMSNNE (SEQ ID NO:26), NPTMCNNE (SEQ ID NO:15); or NPTMSNNE (SEQ ID NO:27). In some embodiments, the NetG1 polypeptide further comprises zero, one, two, three, or four conservative amino acid substitutions. In some embodiments, the NetG1 polypeptide further comprises zero, one, two, or three conservative amino acid substitutions. In some embodiments, the NetG1 polypeptide further comprises zero, one, or two conservative amino acid substitutions. In some embodiments, the NetG1 polypeptide further comprises zero or one conservative amino acid substitutions. In some embodiments, the NetG1 polypeptide further comprises one conservative amino acid substitution. In some embodiments, the NetG1 polypeptide further comprises two conservative amino acid substitutions. In some embodiments, the NetG1 polypeptide further comprises three conservative amino acid substitutions. In some embodiments, the NetG1 polypeptide further comprises four conservative amino acid substitutions.

In some embodiments, the NetG1 polypeptide comprises up to 18 amino acids and comprises TFCAMGNPYMCNNE (SEQ ID NO:1). In some embodiments, the NetG1 polypeptide comprises up to 18 amino acids and comprises TFSAMGNPYMCNNE (SEQ ID NO: 16). In some embodiments, the NetG1 polypeptide comprises up to 18 amino acids and comprises TFCAMGNPYMSNNE (SEQ ID NO:17). In some embodiments, the NetG1 polypeptide comprises up to 18 amino acids and comprises TFSAMGNPYMSNNE (SEQ ID NO: 18). In some embodiments, the NetG1 polypeptide comprises up to 13 amino acids and comprises GNPYMCNNE (SEQ ID NO:2). In some embodiments, the NetG1 polypeptide comprises up to 13 amino acids and comprises GNPYMSNNE (SEQ ID NO:19). In some embodiments, the NetG1 polypeptide comprises up to 20 amino acids and comprises AVGE-IFVDELHLARYF (SEQ ID NO:3). In some embodiments, the NetG1 polypeptide comprises up to 10 amino acids and comprises VGEIFV (SEQ ID NO:4). In some embodiments, the NetG1 polypeptide comprises up to 15 amino acids and comprises EYSTGYTTNSK (SEQ ID NO: 5). In some embodiments, the NetG1 polypeptide comprises up to 10 amino acids and comprises STGYTT (SEQ ID NO:6). In some embodiments, the NetG1 polypeptide comprises up to 16 amino acids and comprises ATDCLDAFHMDP (SEQ ID NO:7). In some embodiments, the NetG1 polypeptide comprises up to 16 amino acids and comprises ATD-SLDAFHMDP (SEQ ID NO: 20). In some embodiments, the NetG1 polypeptide comprises up to 13 amino acids and comprises ATDCLDAFH (SEQ ID NO:8). In some embodiments, the NetG1 polypeptide comprises up to 13 amino acids and comprises ATDSLDAFH (SEQ ID NO:21). In some embodiments, the NetG1 polypeptide comprises up to 18 amino acids and comprises TFCAMGNPTMCNNE (SEQ ID NO:9). In some embodiments, the NetG1 polypeptide comprises up to 18 amino acids and comprises TFSAMGNPTMCNNE (SEQ ID NO:22). In some embodiments, the NetG1 polypeptide comprises up to 18 amino acids and comprises TFCAMGNPTMSNNE (SEQ ID NO:23). In some embodiments, the NetG1 polypeptide comprises up to 18 amino acids and comprises TFSAMGNPTMSNNE (SEQ ID NO:24). In some embodiments, the NetG1 polypeptide comprises up to 13 amino acids and comprises GNPTMCNNE (SEQ ID NO:10). In some embodiments, the NetG1 polypeptide comprises up to 13 amino acids and comprises GNPTMSNNE (SEQ ID NO:25). In some embodiments, the NetG1 polypeptide comprises up to 12 amino acids and comprises NPYMCNNE (SEQ ID NO: 14). In some embodiments, the NetG1 polypeptide comprises up to 12 amino acids and comprises NPYMSNNE (SEQ ID NO:26). In some embodiments, the NetG1 polypeptide comprises up to 12 amino acids and comprises NPTMCNNE (SEQ ID NO:15). In some embodiments, the isolated NetG1 polypeptide comprises up to 12 amino acids and comprises NPTMSNNE (SEQ ID NO:27). In some embodiments, the NetG1 polypeptide further comprises zero, one, two, three, or four conservative amino acid substitutions. In some embodiments, the NetG1 polypeptide further comprises zero, one, two, or three conservative amino acid substitutions. In some embodiments, the NetG1 polypeptide further comprises zero, one, or two conservative amino acid substitutions. In some embodiments, the NetG1 polypeptide further comprises zero or one conservative amino acid substitutions. In some embodiments, the NetG1 polypeptide further comprises one conservative amino acid substitution. In some embodiments, the NetG1 polypeptide further comprises two conservative amino acid substitutions. In some embodiments, the NetG1 polypeptide further comprises three conservative amino acid substitutions. In some embodiments, the NetG1 polypeptide further comprises four conservative amino acid substitutions.

In some embodiments, the NetG1 polypeptide consists of SEQ ID NO: 1, SEQ ID NO:16, SEQ ID NO: 17, SEQ ID NO: 18, SEQ ID NO:2, SEQ ID NO: 19, SEQ ID NO:3, SEQ ID NO:4, SEQ ID NO:5, SEQ ID NO:6, SEQ ID NO:7, SEQ ID NO:20, SEQ ID NO:8, SEQ ID NO:21, SEQ ID NO:9, SEQ ID NO:22, SEQ ID NO:23, SEQ ID NO:24, SEQ ID NO: 10, SEQ ID NO: 25, SEQ ID NO: 14, SEQ ID NO:26, SEQ ID NO: 15, or SEQ ID NO:27. In some embodiments, the NetG1 polypeptide consists of SEQ ID NO:1. In some embodiments, the NetG1 polypeptide consists of SEQ ID NO: 16. In some embodiments, the NetG1 polypeptide consists of SEQ ID NO: 17. In some embodiments, the NetG1 polypeptide consists of SEQ ID NO: 18. In some embodiments, the NetG1 polypeptide consists of SEQ ID NO:2. In some embodiments, the NetG1 polypeptide consists of SEQ ID NO: 19. In some embodiments, the NetG1 polypeptide consists of SEQ ID NO:3. In some embodiments, the NetG1 polypeptide consists of SEQ ID NO:4. In some embodiments, the NetG1 polypeptide consists of SEQ ID NO: 5. In some embodiments, the NetG1 polypeptide consists of SEQ ID NO:6. In some embodiments, the NetG1 polypeptide consists of SEQ ID NO:7. In some embodiments, the NetG1 polypeptide consists of SEQ ID NO:20. In some embodiments, the NetG1 polypeptide consists of SEQ ID NO:8. In some embodiments, the NetG1 polypeptide consists of SEQ ID NO: 21. In some embodiments, the NetG1 polypeptide consists of SEQ ID NO:9. In some embodiments, the NetG1 polypeptide consists of SEQ ID NO:22. In some embodiments, the NetG1 polypeptide consists of SEQ ID NO:23. In some embodiments, the NetG1 polypeptide consists of SEQ ID NO:24. In some embodiments, the NetG1 polypeptide consists of SEQ ID NO: 10. In some embodiments, the NetG1 polypeptide consists of SEQ ID NO:25. In some embodiments, the NetG1 polypeptide consists of SEQ ID NO: 14. In some embodiments, the NetG1 polypeptide consists of SEQ ID NO:26. In some embodiments, the NetG1 polypeptide consists of SEQ ID NO: 15. In some embodiments, the NetG1 polypeptide consists of SEQ ID NO: 27. In some embodiments, the NetG1 polypeptide further comprises zero, one, two, three, or four conservative amino acid substitutions. In some embodiments, the NetG1 polypeptide further comprises zero, one, two, or three conservative amino acid substitutions. In some embodiments, the NetG1 polypeptide further comprises zero, one, or two conservative amino acid substitutions. In some embodiments, the NetG1 polypeptide further comprises zero or one conservative amino acid substitutions. In some embodiments, the NetG1 polypeptide further comprises one conservative amino acid substitution. In some embodiments, the NetG1 polypeptide further comprises two conservative amino acid substitutions. In some embodiments, the NetG1 polypeptide further comprises three conservative amino acid substitutions. In some embodiments, the NetG1 polypeptide further comprises four conservative amino acid substitutions.

In some embodiments, the NGL-1 polypeptide comprises up to 20 amino acids and comprises VCSCSNQFSKVICV (SEQ ID NO:11), VSSCSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSS-CSNQFSKVISV (SEQ ID NO:32), VCSSSNQFSKVISV (SEQ ID NO:33), or VSSSSNQFSKVISV (SEQ ID NO:34). In some embodiments, the NGL-1 polypeptide comprises up to 20 amino acids and comprises VCSCSNQFSKVICV (SEQ ID NO:11). In some embodiments, the NGL-1 polypeptide comprises up to 20 amino acids and comprises VSSCSNQFSKVICV (SEQ ID NO:28). In some embodiments, the NGL-1 polypeptide comprises up to 20 amino acids and comprises VCSSSNQFSKVICV (SEQ ID NO:29). In some embodiments, the NGL-1 polypeptide comprises up to 20 amino acids and comprises VCSCSNQFSKVISV (SEQ ID NO:30). In some embodiments, the NGL-1 polypeptide comprises up to 20 amino acids and comprises VSSSSNQFSKVICV (SEQ ID NO:31). In some embodiments, the NGL-1 polypeptide comprises up to 20 amino acids and comprises VSSCSNQFSKVISV (SEQ ID NO:32). In some embodiments, the NGL-1 polypeptide comprises up to 20 amino acids and comprises VCSSSNQFSKVISV (SEQ ID NO:33). In some embodiments, the NGL-1 polypeptide comprises up to 20 amino acids and comprises VSSSSNQFSKVISV (SEQ ID NO:34). In some embodiments, the NGL-1 polypeptide further comprises zero, one, two, three, or four conservative amino acid substitutions. In some embodiments, the NGL-1 polypeptide further comprises zero, one, two, or three conservative amino acid substitutions. In some embodiments, the NGL-1 polypeptide further comprises zero, one, or two conservative amino acid substitutions. In some embodiments, the NGL-1 polypeptide further comprises zero or one conservative amino acid substitutions. In some embodiments, the NGL-1 polypeptide further comprises one conservative amino acid substitution. In some embodiments, the NGL-1 polypeptide further comprises two conservative amino acid substitutions. In some embodiments, the NGL-1 polypeptide further comprises three conservative amino acid substitutions. In some embodiments, the NGL-1 polypeptide further comprises four conservative amino acid substitutions.

In some embodiments, the NGL-1 polypeptide comprises up to 18 amino acids and comprises VCSCSNQFSKVICV (SEQ ID NO:11), VSSCSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSS-CSNQFSKVISV (SEQ ID NO:32), VCSSSNQFSKVISV (SEQ ID NO:33), or VSSSSNQFSKVISV (SEQ ID NO:34). In some embodiments, the NGL-1 polypeptide comprises up to 18 amino acids and comprises VCSCSNQFSKVICV (SEQ ID NO:11). In some embodiments, the NGL-1 polypeptide comprises up to 18 amino acids and comprises VSSCSNQFSKVICV (SEQ ID NO:28). In some embodiments, the NGL-1 polypeptide comprises up to 18 amino acids and comprises VCSSSNQFSKVICV (SEQ ID NO:29). In some embodiments, the NGL-1 polypeptide comprises up to 18 amino acids and comprises VCSCSNQFSKVISV (SEQ ID NO:30). In some embodiments, the NGL-1 polypeptide comprises up to 18 amino acids and comprises VSSSSNQFSKVICV (SEQ ID NO:31). In some embodiments, the NGL-1 polypeptide comprises up to 18 amino acids and comprises VSSCSNQFSKVISV (SEQ ID NO:32). In some embodiments, the NGL-1 polypeptide comprises up to 18 amino acids and comprises VCSSSNQFSKVISV (SEQ ID NO:33). In some embodiments, the NGL-1 polypeptide comprises up to 18 amino acids and comprises VSSSSNQFSKVISV (SEQ ID NO:34). In some embodiments, the NGL-1 polypeptide further comprises zero, one, two, three, or four conservative amino acid substitutions. In some embodiments, the NGL-1 polypeptide further comprises zero, one, two, or three conservative amino acid substitutions. In some embodiments, the NGL-1 polypeptide further comprises zero, one, or two conservative amino acid substitutions. In some embodiments, the NGL-1 polypeptide further comprises zero or one conservative amino acid substitutions. In some embodiments, the NGL-1 polypeptide further comprises one conservative amino acid substitution. In some embodiments, the NGL-1 polypeptide further comprises two conservative amino acid substitutions. In some embodiments, the NGL-1 polypeptide further comprises three conservative amino acid substitutions. In some embodiments, the NGL-1 polypeptide further comprises four conservative amino acid substitutions.

In some embodiments, the NGL-1 polypeptide consists of VCSCSNQFSKVICV (SEQ ID NO: 11), VSS-CSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSS-CSNQFSKVISV (SEQ ID NO:32), VCSSSNQFSKVISV (SEQ ID NO:33), or VSSSSNQFSKVISV (SEQ ID NO:34). In some embodiments, the NGL-1 polypeptide consists of SEQ ID NO:11. In some embodiments, the NGL-1 polypeptide consists of SEQ ID NO:28. In some embodiments, the NGL-1 polypeptide consists of SEQ ID NO:29. In some embodiments, the NGL-1 polypeptide consists of SEQ ID NO:30. In some embodiments, the NGL-1 polypeptide consists of SEQ ID NO:31. In some embodiments, the NGL-1 polypeptide consists of SEQ ID NO:32. In some embodiments, the NGL-1 polypeptide consists of SEQ ID NO:33. In some embodiments, the NGL-1 polypeptide consists of SEQ ID NO:34. In some embodiments, the NGL-1 polypeptide further comprises zero, one, two, three, or four conservative amino acid substitutions. In some embodiments, the NGL-1 polypeptide further comprises zero, one, two, or three conservative amino acid substitutions. In some embodiments, the NGL-1 polypeptide further comprises zero, one, or two conservative amino acid substitutions. In some embodiments, the NGL-1 polypeptide further comprises zero or one conservative amino acid substitutions. In some embodiments, the NGL-1 polypeptide further comprises one conservative amino acid substitution. In some embodiments, the NGL-1 polypeptide further comprises two conservative amino acid substitutions. In some embodiments, the NGL-1 polypeptide further comprises three conservative amino acid substitutions. In some embodiments, the NGL-1 polypeptide further comprises four conservative amino acid substitutions.

The present disclosure also provides methods of treating a human having a cancer or any disease that includes chronic fibrosis or inflammation comprising administering to the human in need thereof an antibody, or antigen-binding fragment thereof, that binds to any of the NetG1 polypeptides or NGL-1 polypeptides described herein. In some embodiments, the antibody, or antigen-binding fragment thereof, that binds to any of the NetG1 polypeptides or NGL-1 polypeptides described herein are any of the antibodies, or antigen-binding fragments thereof, described herein. In some embodiments, the antibody, or antigen-binding fragment thereof, is present within a composition comprising a pharmaceutically acceptable carrier.

In some embodiments, the isolated antibodies, or antigen-binding fragments thereof, can bind to an isolated NetG1 polypeptide that comprises up to 20 amino acids and comprises: TFCAMGNPYMCNNE (SEQ ID NO:1), TFSAMGNPYMCNNE (SEQ ID NO:16), TFCAMGNPYMSNNE (SEQ ID NO:17), TFSAMGNPYMSNNE (SEQ ID NO:18), GNPYMCNNE (SEQ ID NO:2), GNPYMSNNE (SEQ ID NO:19), AVGE-IFVDELHLARYF (SEQ ID NO:3), VGEIFV (SEQ ID NO:4), EYSTGYTTNSK (SEQ ID NO:5), STGYTT (SEQ ID NO: 6), ATDCLDAFHMDP (SEQ ID NO:7), ATD-SLDAFHMDP (SEQ ID NO:20), ATDCLDAFH (SEQ ID NO:8), ATDSLDAFH (SEQ ID NO:21), TFCAMGNPTMCNNE (SEQ ID NO: 9), TFSAMGNPTMCNNE (SEQ ID NO:22), TFCAMGNPTMSNNE (SEQ ID NO:23), TFSAMGNPTMSNNE (SEQ ID NO:24), GNPTMCNNE (SEQ ID NO:10), GNPTMSNNE (SEQ ID NO:25), NPYMCNNE (SEQ ID NO:14), NPYMSNNE (SEQ ID NO:26), NPTMCNNE (SEQ ID NO:15), or NPTMSNNE (SEQ ID NO:27). In some embodiments, the isolated antibodies, or antigen-binding fragments thereof, can bind to an isolated NetG1 polypeptide that comprises up to 20 amino acids and comprises TFCAMGNPYMCNNE (SEQ ID NO: 1). In some embodiments, the isolated antibodies, or antigen-binding fragments thereof, can bind to an isolated NetG1 polypeptide that comprises up to 20 amino acids and comprises TFSAMGNPYMCNNE (SEQ ID NO:16). In some embodiments, the isolated antibodies, or antigen-binding fragments thereof, can bind to an isolated NetG1 polypeptide that comprises up to 20 amino acids and comprises TFCAMGNPYMSNNE (SEQ ID NO:17). In some embodiments, the isolated antibodies, or antigen-binding fragments thereof, can bind to an isolated NetG1 polypeptide that comprises up to 20 amino acids and comprises TFSAMGNPYMSNNE (SEQ ID NO:18). In some embodiments, the isolated antibodies, or antigen-binding fragments thereof, can bind to an isolated NetG1 polypeptide that comprises up to 20 amino acids and comprises GNPYMCNNE (SEQ ID NO:2). In some embodiments, the isolated antibodies, or antigen-binding fragments thereof, can bind to an isolated NetG1 polypeptide that comprises up to 20 amino acids and comprises GNPYMSNNE (SEQ ID NO: 19). In some embodiments, the isolated antibodies, or antigen-binding fragments thereof, can bind to an isolated NetG1 polypeptide that comprises up to 20 amino acids and comprises AVGEIFVDELHLARYF (SEQ ID NO:3). In some embodiments, the isolated antibodies, or antigen-binding fragments thereof, can bind to an isolated NetG1 polypeptide that comprises up to 20 amino acids and comprises VGEIFV (SEQ ID NO:4). In some embodiments, the isolated antibodies, or antigen-binding fragments thereof, can bind to an isolated NetG1 polypeptide that comprises up to 20 amino acids and comprises EYSTGYTTNSK (SEQ ID NO:5). In some embodiments, the isolated antibodies, or antigen-binding fragments thereof, can bind to an isolated NetG1 polypeptide that comprises up to 20 amino acids and comprises STGYTT (SEQ ID NO: 6). In some embodiments, the isolated antibodies, or antigen-binding fragments thereof, can bind to an isolated NetG1 polypeptide that comprises up to 20 amino acids and comprises ATD-CLDAFHMDP (SEQ ID NO:7). In some embodiments, the isolated antibodies, or antigen-binding fragments thereof, can bind to an isolated NetG1 polypeptide that comprises up to 20 amino acids and comprises ATDSLDAFHMDP (SEQ ID NO:20). In some embodiments, the isolated antibodies, or antigen-binding fragments thereof, can bind to an isolated NetG1 polypeptide that comprises up to 20 amino acids and comprises ATDCLDAFH (SEQ ID NO:8). In some embodiments, the isolated antibodies, or antigen-binding fragments thereof, can bind to an isolated NetG1 polypeptide that comprises up to 20 amino acids and comprises ATD-SLDAFH (SEQ ID NO:21). In some embodiments, the isolated antibodies, or antigen-binding fragments thereof, can bind to an isolated NetG1 polypeptide that comprises up to 20 amino acids and comprises TFCAMGNPTMCNNE (SEQ ID NO:9). In some embodiments, the isolated antibodies, or antigen-binding fragments thereof, can bind to an isolated NetG1 polypeptide that comprises up to 20 amino acids and comprises TFSAMGNPTMCNNE (SEQ ID NO: 22). In some embodiments, the isolated antibodies, or antigen-binding fragments thereof, can bind to an isolated NetG1 polypeptide that comprises up to 20 amino acids and comprises TFCAMGNPTMSNNE (SEQ ID NO:23). In some embodiments, the isolated antibodies, or antigen-binding fragments thereof, can bind to an isolated NetG1 polypeptide that comprises up to 20 amino acids and comprises TFSAMGNPTMSNNE (SEQ ID NO:24). In some embodiments, the isolated antibodies, or antigen-binding fragments thereof, can bind to an isolated NetG1 polypeptide that comprises up to 20 amino acids and comprises GNPTMCNNE (SEQ ID NO:10). In some embodiments, the isolated antibodies, or antigen-binding fragments thereof, can bind to an isolated NetG1 polypeptide that comprises up to 20 amino acids and comprises GNPTMSNNE (SEQ ID NO:25). In some embodiments, the isolated antibodies, or antigen-binding fragments thereof, can bind to an isolated NetG1 polypeptide that comprises up to 20 amino acids and comprises NPYMCNNE (SEQ ID NO:14). In some embodiments, the isolated antibodies, or antigen-binding fragments thereof, can bind to an isolated NetG1 polypeptide that comprises up to 20 amino acids and comprises NPYMSNNE (SEQ ID NO:26). In some embodiments, the isolated antibodies, or antigen-binding fragments thereof, can bind to an isolated NetG1 polypeptide that comprises up to 20 amino acids and comprises NPTMCNNE (SEQ ID NO:15). In some embodiments, the isolated antibodies, or antigen-binding fragments thereof, can bind to an isolated NetG1 polypeptide that comprises up to 20 amino acids and comprises NPTMSNNE (SEQ ID NO:27).

In some embodiments, the isolated antibodies, or antigen-binding fragments thereof, can bind to an isolated NGL-1 polypeptide that comprises up to 20 amino acids and comprises VCSCSNQFSKVICV (SEQ ID NO:11), VSS-CSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSS-CSNQFSKVISV (SEQ ID NO:32), VCSSSNQFSKVISV (SEQ ID NO:33), or VSSSSNQFSKVISV (SEQ ID NO:34). In some embodiments, the isolated antibodies, or antigen-binding fragments thereof, can bind to an isolated NGL-1 polypeptide that comprises up to 20 amino acids and comprises VCSCSNQFSKVICV (SEQ ID NO:11). In some embodiments, the isolated antibodies, or antigen-binding fragments thereof, can bind to an isolated NGL-1 polypeptide that comprises up to 20 amino acids and comprises VSSCSNQFSKVICV (SEQ ID NO:28). In some embodiments, the isolated antibodies, or antigen-binding fragments thereof, can bind to an isolated NGL-1 polypeptide that comprises up to 20 amino acids and comprises VCSSSNQFSKVICV (SEQ ID NO: 29). In some embodiments, the isolated antibodies, or antigen-binding fragments thereof, can bind to an isolated NGL-1 polypeptide that comprises up to 20 amino acids and comprises VCSCSNQFSKVISV (SEQ ID NO:30). In some embodiments, the isolated antibodies, or antigen-binding fragments thereof, can bind to an isolated NGL-1 polypeptide that comprises up to 20 amino acids and comprises VSSSSNQFSKVICV (SEQ ID NO:31). In some embodiments, the isolated antibodies, or antigen-binding fragments thereof, can bind to an isolated NGL-1 polypeptide that comprises up to 20 amino acids and comprises VSS-CSNQFSKVISV (SEQ ID NO: 32). In some embodiments, the isolated antibodies, or antigen-binding fragments thereof, can bind to an isolated NGL-1 polypeptide that comprises up to 20 amino acids and comprises VCSSSNQFSKVISV (SEQ ID NO:33). In some embodiments, the isolated antibodies, or antigen-binding fragments thereof, can bind to an isolated NGL-1 polypeptide that comprises up to 20 amino acids and comprises VSSSSNQFSKVISV (SEQ ID NO:34). In some embodiments, the isolated NetG1 polypeptide or NGL-1 polypeptide further comprises zero, one, two, three, or four conservative amino acid substitutions. In some embodiments, the isolated NetG1 polypeptide or NGL-1 polypeptide further comprises zero, one, two, or three conservative amino acid substitutions. In some embodiments, the NetG1 polypeptide or NGL-1 polypeptide further comprises zero, one, or two conservative amino acid substitutions. In some embodiments, the isolated NetG1 polypeptide or NGL-1 polypeptide further comprises zero or one conservative amino acid substitutions. In some embodiments, the isolated NetG1 polypeptide or NGL-1 polypeptide further comprises one conservative amino acid substitution. In some embodiments, the isolated NetG1 polypeptide or NGL-1 polypeptide further comprises two conservative amino acid substitutions. In some embodiments, the isolated NetG1 polypeptide or NGL-1 polypeptide further comprises three conservative amino acid substitutions. In some embodiments, the isolated NetG1 polypeptide or NGL-1 polypeptide further comprises four conservative amino acid substitutions.

In some embodiments, the isolated antibodies, or antigen-binding fragments thereof, can bind to an isolated NetG1 polypeptide that comprises up to 18 amino acids and comprises TFCAMGNPYMCNNE (SEQ ID NO:1). In some embodiments, the isolated antibodies, or antigen-binding fragments thereof, can bind to an isolated NetG1 polypeptide that comprises comprises up to 18 amino acids and comprises TFSAMGNPYMCNNE (SEQ ID NO:16). In some embodiments, the isolated antibodies, or antigen-binding fragments thereof, can bind to an isolated NetG1 polypeptide that comprises up to 18 amino acids and comprises TFCAMGNPYMSNNE (SEQ ID NO:17). In some embodiments, the isolated antibodies, or antigen-binding fragments thereof, can bind to an isolated NetG1 polypeptide that comprises comprises up to 18 amino acids and comprises TFSAMGNPYMSNNE (SEQ ID NO:18). In some embodiments, the isolated antibodies, or antigen-binding fragments thereof, can bind to an isolated NetG1 polypeptide that comprises up to 13 amino acids and comprises GNPYMCNNE (SEQ ID NO:2). In some embodiments, the isolated antibodies, or antigen-binding fragments thereof, can bind to an isolated NetG1 polypeptide that comprises up to 13 amino acids and comprises GNPYMSNNE (SEQ ID NO:19). In some embodiments, the isolated antibodies, or antigen-binding fragments thereof, can bind to an isolated NetG1 polypeptide that comprises up to 20 amino acids and comprises AVGEIFVDELHLARYF (SEQ ID NO:3). In some embodiments, the isolated antibodies, or antigen-binding fragments thereof, can bind to an isolated NetG1 polypeptide that comprises comprises up to 10 amino acids and comprises VGEIFV (SEQ ID NO:4). In some embodiments, the isolated antibodies, or antigen-binding fragments thereof, can bind to an isolated NetG1 polypeptide that comprises up to 15 amino acids and comprises EYSTGYTTNSK (SEQ ID NO:5). In some embodiments, the isolated antibodies, or antigen-binding fragments thereof, can bind to an isolated NetG1 polypeptide that comprises up to 10 amino acids and comprises STGYTT (SEQ ID NO:6). In some embodiments, the isolated antibodies, or antigen-binding fragments thereof, can bind to an isolated NetG1 polypeptide that comprises comprises up to 16 amino acids and comprises ATDCLDAFHMDP (SEQ ID NO:7). In some embodiments, the isolated antibodies, or antigen-binding fragments thereof, can bind to an isolated NetG1 polypeptide that comprises up to 16 amino acids and comprises ATDSLDAFHMDP (SEQ ID NO:20). In some embodiments, the isolated antibodies, or antigen-binding fragments thereof, can bind to an isolated NetG1 polypeptide that comprises up to 13 amino acids and comprises ATDCLDAFH (SEQ ID NO:8). In some embodiments, the isolated antibodies, or antigen-binding fragments thereof, can bind to an isolated NetG1 polypeptide that comprises up to 13 amino acids and comprises ATDSLDAFH (SEQ ID NO: 21). In some embodiments, the isolated antibodies, or antigen-binding fragments thereof, can bind to an isolated NetG1 polypeptide that comprises up to 18 amino acids and comprises TFCAMGNPTMCNNE (SEQ ID NO:9). In some embodiments, the isolated antibodies, or antigen-binding fragments thereof, can bind to an isolated NetG1 polypeptide that comprises up to 18 amino acids and comprises TFSAMGNPTMCNNE (SEQ ID NO: 22). In some embodiments, the isolated antibodies, or antigen-binding fragments thereof, can bind to an isolated NetG1 polypeptide that comprises up to 18 amino acids and comprises TFCAMGNPTMSNNE (SEQ ID NO:23). In some embodiments, the isolated antibodies, or antigen-binding fragments thereof, can bind to an isolated NetG1 polypeptide that comprises up to 18 amino acids and comprises TFSAMGNPTMSNNE (SEQ ID NO: 24). In some embodiments, the isolated antibodies, or antigen-binding fragments thereof, can bind to an isolated NetG1 polypeptide that comprises up to 13 amino acids and comprises GNPTMCNNE (SEQ ID NO:10). In some embodiments, the isolated antibodies, or antigen-binding fragments thereof, can bind to an isolated NetG1 polypeptide that comprises comprises up to 13 amino acids and comprises GNPTMSNNE (SEQ ID NO:25). In some embodiments, the isolated antibodies, or antigen-binding fragments thereof, can bind to an isolated NetG1 polypeptide that comprises up to 12 amino acids and comprises NPYMCNNE (SEQ ID NO:14). In some embodiments, the isolated antibodies, or antigen-binding fragments thereof, can bind to an isolated NetG1 polypeptide that comprises up to 12 amino acids and comprises NPYMSNNE (SEQ ID NO:26). In some embodiments, the isolated antibodies, or antigen-binding fragments thereof, can bind to an isolated NetG1 polypeptide that comprises up to 12 amino acids and comprises NPTMCNNE (SEQ ID NO: 15). In some embodiments, the isolated NetG1 polypeptide comprises up to 12 amino acids and comprises NPTMSNNE (SEQ ID NO:27).

In some embodiments, the isolated antibodies, or antigen-binding fragments thereof, can bind to an isolated NetG1 polypeptide that comprises up to 18 amino acids and comprises VCSCSNQFSKVICV (SEQ ID NO:11), VSSCSNQFSKVICV (SEQ ID NO:28), VCSSSNQFSKVICV (SEQ ID NO:29), VCSCSNQFSKVISV (SEQ ID NO:30), VSSSSNQFSKVICV (SEQ ID NO:31), VSSCSNQFSKVISV (SEQ ID NO:32), VCSSSNQFSKVISV (SEQ ID NO:33), or VSSSSNQFSKVISV (SEQ ID NO:34). In some embodiments, the isolated antibodies, or antigen-binding fragments thereof, can bind to an isolated NetG1 polypeptide that comprises up to 18 amino acids and comprises VCSCSNQFSKVICV (SEQ ID NO:11). In some embodiments, the isolated antibodies, or antigen-binding fragments thereof, can bind to an isolated NetG1 polypeptide that comprises up to 18 amino acids and comprises VSSCSNQFSKVICV (SEQ ID NO:28). In some embodiments, the isolated antibodies, or antigen-binding fragments thereof, can bind to an isolated NetG1 polypeptide that comprises up to 18 amino acids and comprises VCSSSNQFSKVICV (SEQ ID NO: 29). In some embodiments, the isolated antibodies, or antigen-binding fragments thereof, can bind to an isolated NetG1 polypeptide that comprises up to 18 amino acids and comprises VCSCSNQFSKVISV (SEQ ID NO:30). In some embodiments, the isolated antibodies, or antigen-binding fragments thereof, can bind to an isolated NetG1 polypeptide that comprises up to 18 amino acids and comprises VSSSSNQFSKVICV (SEQ ID NO:31). In some embodiments, the isolated antibodies, or antigen-binding fragments thereof, can bind to an isolated NetG1 polypeptide that comprises up to 18 amino acids and comprises VSSCSNQFSKVISV (SEQ ID NO: 32). In some embodiments, the isolated antibodies, or antigen-binding fragments thereof, can bind to an isolated NetG1 polypeptide that comprises up to 18 amino acids and comprises VCSSSNQFSKVISV (SEQ ID NO:33). In some embodiments, the isolated antibodies, or antigen-binding fragments thereof, can bind to an isolated NetG1 polypeptide that comprises up to 18 amino acids and comprises VSSSSNQFSKVISV (SEQ ID NO:34). In some embodiments, the isolated NetG1 polypeptide or NGL-1 polypeptide further comprises zero, one, two, three, or four conservative amino acid substitutions. In some embodiments, the isolated NetG1 polypeptide or NGL-1 polypeptide further comprises zero, one, two, or three conservative amino acid substitutions. In some embodiments, the NetG1 polypeptide or NGL-1 polypeptide further comprises zero, one, or two conservative amino acid substitutions. In some embodiments, the isolated NetG1 polypeptide or NGL-1 polypeptide further comprises zero or one conservative amino acid substitutions. In some embodiments, the isolated NetG1 polypeptide or NGL-1 polypeptide further comprises one conservative amino acid substitution. In some embodiments, the isolated NetG1 polypeptide or NGL-1 polypeptide further comprises two conservative amino acid substitutions. In some embodiments, the isolated NetG1 polypeptide or NGL-1 polypeptide further comprises three conservative amino acid substitutions. In some embodiments, the isolated NetG1 polypeptide or NGL-1 polypeptide further comprises four conservative amino acid substitutions.

In some embodiments, the isolated antibodies, or antigen-binding fragments thereof, can bind to an isolated NetG1 polypeptide that consists of SEQ ID NO:1, SEQ ID NO: 16, SEQ ID NO: 17, SEQ ID NO: 18, SEQ ID NO:2, SEQ ID NO: 19, SEQ ID NO:3, SEQ ID NO:4, SEQ ID NO: 5, SEQ ID NO:6, SEQ ID NO: 7, SEQ ID NO:20, SEQ ID NO:8, SEQ ID NO:21, SEQ ID NO: 9, SEQ ID NO: 22, SEQ ID NO:23, SEQ ID NO:24, SEQ ID NO: 10, SEQ ID NO:25, SEQ ID NO: 14, SEQ ID NO:26, SEQ ID NO: 15, or SEQ ID NO:27. In some embodiments, the isolated antibodies, or antigen-binding fragments thereof, can bind to an isolated NetG1 polypeptide that consists of SEQ ID NO: 1. In some embodiments, the isolated antibodies, or antigen-binding fragments thereof, can bind to an isolated NetG1 polypeptide that consists of SEQ ID NO:16. In some embodiments, the isolated antibodies, or antigen-binding fragments thereof, can bind to an isolated NetG1 polypeptide that consists of SEQ ID NO: 17. In some embodiments, the isolated antibodies, or antigen-binding fragments thereof, can bind to an isolated NetG1 polypeptide that consists of SEQ ID NO:18. In some embodiments, the isolated antibodies, or antigen-binding fragments thereof, can bind to an isolated NetG1 polypeptide that consists of SEQ ID NO:2. In some embodiments, the isolated antibodies, or antigen-binding fragments thereof, can bind to an isolated NetG1 polypeptide that consists of SEQ ID NO: 19. In some embodiments, the isolated antibodies, or antigen-binding fragments thereof, can bind to an isolated NetG1 polypeptide that consists of SEQ ID NO:3. In some embodiments, the isolated antibodies, or antigen-binding fragments thereof, can bind to an isolated NetG1 polypeptide that consists of SEQ ID NO:4. In some embodiments, the isolated antibodies, or antigen-binding fragments thereof, can bind to an isolated NetG1 polypeptide that consists of SEQ ID NO:5. In some embodiments, the isolated antibodies, or antigen-binding fragments thereof, can bind to an isolated NetG1 polypeptide that consists of SEQ ID NO:6. In some embodiments, the isolated antibodies, or antigen-binding fragments thereof, can bind to an isolated NetG1 polypeptide that consists of SEQ ID NO:7. In some embodiments, the isolated antibodies, or antigen-binding fragments thereof, can bind to an isolated NetG1 polypeptide that consists of SEQ ID NO:20. In some embodiments, the isolated antibodies, or antigen-binding fragments thereof, can bind to an isolated NetG1 polypeptide that consists of SEQ ID NO:8. In some embodiments, the isolated antibodies, or antigen-binding fragments thereof, can bind to an isolated NetG1 polypeptide that consists of SEQ ID NO:21. In some embodiments, the isolated antibodies, or antigen-binding fragments thereof, can bind to an isolated NetG1 polypeptide that consists of SEQ ID NO:9. In some embodiments, the isolated antibodies, or antigen-binding fragments thereof, can bind to an isolated NetG1 polypeptide that consists of SEQ ID NO:22. In some embodiments, the isolated antibodies, or antigen-binding fragments thereof, can bind to an isolated NetG1 polypeptide that consists of SEQ ID NO:23. In some embodiments, the isolated antibodies, or antigen-binding fragments thereof, can bind to an isolated NetG1 polypeptide that consists of SEQ ID NO:24. In some embodiments, the isolated antibodies, or antigen-binding fragments thereof, can bind to an isolated NetG1 polypeptide that consists of SEQ ID NO: 10. In some embodiments, the isolated antibodies, or antigen-binding fragments thereof, can bind to an isolated NetG1 polypeptide that consists of SEQ ID NO:25. In some embodiments, the isolated antibodies, or antigen-binding fragments thereof, can bind to an isolated NetG1 polypeptide that consists of SEQ ID NO: 14. In some embodiments, the isolated antibodies, or antigen-binding fragments thereof, can bind to an isolated NetG1 polypeptide that consists of SEQ ID NO:26. In some embodiments, the isolated antibodies, or antigen-binding fragments thereof, can bind to an isolated NetG1 polypeptide that consists of SEQ ID NO:15. In some embodiments, the isolated antibodies, or antigen-binding fragments thereof, can bind to an isolated NetG1 polypeptide that consists of SEQ ID NO:27.

In some embodiments, the isolated antibodies, or antigen-binding fragments thereof, can bind to an isolated NGL-1 polypeptide that consists of SEQ ID NO: 11, SEQ ID NO:28, SEQ ID NO: 29, SEQ ID NO:30, SEQ ID NO:31, SEQ ID NO:32, SEQ ID NO:33, or SEQ ID NO:34. In some embodiments, the isolated antibodies, or antigen-binding fragments thereof, can bind to an isolated NGL-1 polypeptide that consists of SEQ ID NO:11. In some embodiments, the isolated antibodies, or antigen-binding fragments thereof, can bind to an isolated NGL-1 polypeptide that consists of SEQ ID NO:28. In some embodiments, the isolated antibodies, or antigen-binding fragments thereof, can bind to an isolated NGL-1 polypeptide that consists of SEQ ID NO:29. In some embodiments, the isolated antibodies, or antigen-binding fragments thereof, can bind to an isolated NGL-1 polypeptide that consists of SEQ ID NO:30. In some embodiments, the isolated antibodies, or antigen-binding fragments thereof, can bind to an isolated NGL-1 polypeptide that consists of SEQ ID NO:31. In some embodiments, the isolated antibodies, or antigen-binding fragments thereof, can bind to an isolated NGL-1 polypeptide that consists of SEQ ID NO:32. In some embodiments, the isolated antibodies, or antigen-binding fragments thereof, can bind to an isolated NGL-1 polypeptide that consists of SEQ ID NO:33. In some embodiments, the isolated antibodies, or antigen-binding fragments thereof, can bind to an isolated NGL-1 polypeptide that consists of SEQ ID NO:34. In some embodiments, the isolated NetG1 polypeptide or NGL-1 polypeptide further comprises zero, one, two, three, or four conservative amino acid substitutions. In some embodiments, the isolated NetG1 polypeptide or NGL-1 polypeptide further comprises zero, one, two, or three conservative amino acid substitutions. In some embodiments, the NetG1 polypeptide or NGL-1 polypeptide further comprises zero, one, or two conservative amino acid substitutions. In some embodiments, the isolated NetG1 polypeptide or NGL-1 polypeptide further comprises zero or one conservative amino acid substitutions. In some embodiments, the isolated NetG1 polypeptide or NGL-1 polypeptide further comprises one conservative amino acid substitution. In some embodiments, the isolated NetG1 polypeptide or NGL-1 polypeptide further comprises two conservative amino acid substitutions. In some embodiments, the isolated NetG1 polypeptide or NGL-1 polypeptide further comprises three conservative amino acid substitutions. In some embodiments, the isolated NetG1 polypeptide or NGL-1 polypeptide further comprises four conservative amino acid substitutions.

In some embodiments, the cancer is a desmoplasia bearing cancer or a cancer associated with chronic fibrosis and/or chronic inflammation. In some embodiments, the cancer is a desmoplasia bearing cancer. In some embodiments, the cancer is a cancer associated with chronic fibrosis. In some embodiments, the cancer is a cancer associated with chronic inflammation. In some embodiments, the cancer is a cancer associated with chronic fibrosis and chronic inflammation.

In some embodiments, the cancer is lung cancer, prostate cancer, breast cancer, liver cancer, pancreatic cancer, kidney cancer, colon cancer, ovarian cancer, skin cancer, or a sarcoma. In some embodiments, the cancer is lung cancer. In some embodiments, the cancer is prostate cancer. In some embodiments, the cancer is breast cancer. In some embodiments, the cancer is liver cancer. In some embodiments, the cancer is pancreatic cancer. In some embodiments, the cancer is kidney cancer. In some embodiments, the cancer is colon cancer. In some embodiments, the cancer is ovarian cancer. In some embodiments, the cancer is skin cancer. In some embodiments, the cancer is a sarcoma. In some embodiments, the pancreatic cancer is pancreatic ductal adenocarcinoma. In some embodiments, the cancer is a solid tumor. In some embodiments, the cancer is a liquid neoplasia.

In some embodiments, the polypeptides, antibodies, and antigen-binding fragments thereof, described herein can be administered to a subject or patient by a variety of routes such as orally, transdermally, subcutaneously, intranasally, intravenously, intraarterially, intramuscularly, intraocularly, topically, locally, intrathecally, intracerebroventricularly, intraspinally, and intracranially. In some embodiments, the polypeptides, antibodies, and antigen-binding fragments thereof, can be formulated as an aqueous solution. In some embodiments, the polypeptides, antibodies, and antigen-binding fragments thereof, are administered intravenously or intracranially.

In some embodiments, the administration of the polypeptides, antibodies, and/or antigen-binding fragments thereof described herein is repeated after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens, a patient can receive anti-NetG1 or anti-NGL1 therapy for a prolonged period of time, such as 6 months, 1 year, or more. The amount of the polypeptides, antibodies, or antigen-binding fragments thereof, described herein administered to the patient is a therapeutically effective amount. A therapeutically effective amount of the polypeptides, antibodies, and antigen-binding fragments thereof, described herein can be administered as a single dose or over the course of a therapeutic regimen, such as over the course of a week, two weeks, three weeks, one month, three months, six months, one year, or longer. Exemplary therapeutic regimens are further described herein. Treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

The therapeutic effect can comprise one or more of a decrease/reduction in tumor, a decrease/reduction in the severity of the cancer (e.g., a reduction or inhibition of metastasis development), a decrease/reduction in symptoms and cancer-related effects, delaying the onset of symptoms and cancer-related effects, reducing the severity of symptoms and cancer-related effects, reducing the severity of an acute episode reducing the number of symptoms and cancer-related effects, reducing the latency of symptoms and cancer-related effects, an amelioration of symptoms and cancer-related effects, reducing secondary symptoms, reducing secondary infections, preventing relapse to a disease, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics, and an increased survival time of the affected host animal, following administration of the agent/composition of the invention. A prophylactic effect can comprise a complete or partial avoidance/inhibition or a delay of cancer development/progression (e.g., a complete or partial avoidance/inhibition or a delay of metastasis development), and an increased survival time of the affected host animal, following administration of the polypeptides, antibodies, and antigen-binding fragments thereof, described herein.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and tests for calcium level and other enzymes to determine the extent of metastasis. CT scans can also be done to look for spread to regions outside of the tumor or cancer.

The use of the polypeptides, antibodies, and antigen-binding fragments thereof, described herein to treat cancer in a patient can result in any demonstrated clinical benefit compared with no therapy (when appropriate) or to a known standard of care. Clinical benefit can be assessed by any method known to one of ordinary skill in the art. In some embodiments, clinical benefit is assessed based on objective response rate (ORR) (determined using RECIST version 1.1), duration of response (DOR), progression-free survival (PFS), and/or overall survival (OS). In some embodiments, a complete response indicates therapeutic benefit. In some embodiments, a partial response indicates therapeutic benefit. In some embodiments, stable disease indicates therapeutic benefit. In some embodiments, an increase in overall survival indicates therapeutic benefit. In some embodiments, therapeutic benefit may constitute an improvement in time to disease progression and/or an improvement in symptoms or quality of life. In some embodiments, a therapeutic benefit may not translate to an increased period of disease control, but rather a markedly reduced symptom burden resulting in improved quality of life. As will be apparent to those of skill in the art, a therapeutic benefit may be observed using the polypeptides, antibodies, or antigen-binding fragments thereof, described herein alone (monotherapy) or adjunctive to, or with, other anti-cancer therapies and/or targeted or non-targeted anti-cancer agents.

In some embodiments, a therapeutic benefit can be assessed using standard clinical tests designed to measure the response to a new treatment for cancer. To assess the therapeutic benefits of the polypeptides, antibodies, and antigen-binding fragments thereof, described herein one or a combination of the following tests can be used: 1) the Response Evaluation Criteria In Solid Tumors (RECIST) version 1.1; 2) immune-related RECIST (irRECIST); 3) the Eastern Cooperative Oncology Group (ECOG) Performance Status; 4) immune-related response criteria (irRC); 5) disease evaluable by assessment of tumor antigens; 6) validated patient reported outcome scales; and/or 7) Kaplan-Meier estimates for overall survival and progression free survival.

Assessment of the change in tumor burden is an important feature of the clinical evaluation of cancer therapeutics. Both tumor shrinkage (objective response) and time to the development of disease progression are important endpoints in cancer clinical trials. Standardized response criteria, known as RECIST (Response Evaluation Criteria in Solid Tumors), were published in 2000. An update (RECIST 1.1) was released in 2009. RECIST criteria are typically used in clinical trials where objective response is the primary study endpoint, as well as in trials where assessment of stable disease, tumor progression or time to progression analyses are undertaken because these outcome measures are based on an assessment of anatomical tumor burden and its change over the course of the trial.

The present disclosure also provides combination therapy methods comprising administering at least two agents to a patient, the first of which is a polypeptide, an antibody, or antigen-binding fragment thereof, described herein, and the second of which is a combination therapeutic agent. The polypeptides, antibodies, and antigen-binding fragments thereof, described herein and the combination therapeutic agents can be administered simultaneously, sequentially, or separately. The combinatorial therapy methods can result in a greater than additive effect.

In the present methods, the polypeptide, antibodies, and antigen-binding fragments thereof, described herein and the combination therapeutic agents can be administered concurrently, either simultaneously or successively. The polypeptides, antibodies, and antigen-binding fragments thereof, described herein and the combination therapeutic agents can be administered successively if they are administered to the patient on the same day, for example, during the same patient visit. Successive administration can occur 1, 2, 3, 4, 5, 6, 7, or 8 hours apart. In contrast, the polypeptides, antibodies, and antigen-binding fragments thereof, described herein and the combination therapeutic agents can be administered separately if they are administered to the patient on different days, for example, the polypeptides, antibodies, and antigen-binding fragments thereof, and the combination therapeutic agents can be administered at a 1-day, 2-day or 3-day, one-week, 2-week or monthly intervals. In the methods of the present disclosure, administration of the polypeptides, antibodies, and antigen-binding fragments thereof, described herein can precede or follow administration of the combination therapeutic agents. In some embodiments, the polypeptides, antibodies, and antigen-binding fragments thereof, described herein and combination therapeutic agents can be administered concurrently for a period of time, followed by a second period of time in which the administration of the polypeptides, antibodies, and antigen-binding fragments thereof, and the combination therapeutic agents is alternated.

In some embodiments, the combination therapeutic agent is a chemotherapeutic agent, an anti-angiogenic agent, an anti-rheumatic drug, an anti-inflammatory agent, a radio-therapeutic, an immunosuppressive agent, or a cytotoxic drug. The polypeptides, antibodies, and antigen-binding fragments thereof, described herein can be used in combination with conventional cancer therapies, such as surgery, radiotherapy, chemotherapy, or combinations thereof.

In some embodiments, the methods further comprise one or both of surgically resecting tumor cells and/or administering radiation therapy. In some embodiments, other therapeutic agents useful for combination tumor therapy with the polypeptides, antibodies, and antigen-binding fragments thereof, described herein include antagonists, such as, antibodies, of other factors that are involved in tumor growth, such as HER2, HER3, HER4, VEGF, or TNF-$\alpha$. In some embodiments, for treatment of cancers it may be beneficial to also administer one or more cytokines to the patient. In some embodiments, the polypeptides, antibodies, and antigen-binding fragments thereof, described herein are co-administered with a growth inhibitory agent.

In some embodiments, for treatment of cancers it may be beneficial to also administer one or more cytokines, or cytokine inhibitors, to the patient. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including, but are not limited to, LIF and kit ligand (KL).

For treatment of cancers, anti-inflammatory agents (such as cytokine inhibitors) can be used in combination with the polypeptides, antibodies, and antigen-binding fragments thereof, described herein. Anti-inflammatory agents include, but are not limited to, acetaminophen, diphenhydramine, meperidine, dexamethasone, pentasa, mesalazine, asacol, codeine phosphate, benorylate, fenbufen, naprosyn, diclofenac, etodolac and indomethacin, aspirin, and ibuprofen.

In some embodiments, for treatment of cancers, chemotherapeutic agents can be used in combination with the polypeptides, antibodies, and antigen-binding fragments thereof, described herein. Chemotherapeutic agents include, but are not limited to, radioactive molecules, toxins (such as cytotoxins or cytotoxic agents) which include any agent that is detrimental to the viability of cells, agents, and liposomes or other vesicles containing chemotherapeutic compounds. Examples of suitable chemotherapeutic agents include, but are not limited to, 1-dehydrotestosterone, 5-fluorouracil decarbazine, 6-mercaptopurine, 6-thioguanine, actinomycin D, adriamycin, aldesleukin, an anti-α5β1 integrin antibody, alkylating agents, allopurinol sodium, altretamine, amifostine, anastrozole, anthramycin (AMC)), anti-mitotic agents, cisdichlorodiamine platinum (II) (DDP) cisplatin, diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), chlorambucil, cisplatin, cladribine, colchicin, conjugated estrogens, cyclophosphamide, cyclothosphamide, cytarabine, cytarabine, cytochalasin B, cytoxan, dacarbazine, dactinomycin, dactinomycin (formerly actinomycin), daunirubicin, daunorucbicin citrate, denileukin diftitox, dexrazoxane, dibromomannitol, dihydroxy anthracin dione, docetaxel, dolasetron mesylate, doxorubicin, dronabinol, E. coli L-asparaginase, eolociximab, emetine, epoetin-a, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine, glucocorticoids, goserelin acetate, gramicidin D, granisetron, hydroxyurea, idarubicin, ifosfamide, interferon α-2b, irinotecan, letrozole, leucovorin calcium, leuprolide acetate, levamisole, lidocaine, lomustine, maytansinoid, mechlorethamine, medroxyprogesterone acetate, megestrol acetate, melphalan, mercaptipurine, mesna, methotrexate, methyltestosterone, mithramycin, mitomycin C, mitotane, mitoxantrone, nilutamide, octreotide acetate, ondansetron, paclitaxel, pamidronate disodium, pentostatin, pilocarpine, plimycin, polifeprosan 20 with carmustine implant, porfimer sodium, procaine, procarbazine, propranolol, rituximab, sargramostim, streptozotocin, tamoxifen, taxol, teniposide, tenoposide, testolactone, tetracaine, thioepa chlorambucil, thioguanine, thiotepa, topotecan, toremifene citrate, trastuzumab, tretinoin, valrubicin, vinblastine sulfate, vincristine sulfate, and vinorelbine tartrate, or any salt thereof. In some embodiments, the methods comprise administering at least one chemotherapeutic agent to the patient.

Examples of immunotherapeutic agents include, but are not limited to, OPDIVO® (nivolumab), KEYTRUDA® (pembrolizumab), TECENTRIQ® (atezolizumab), IMFINZI® (durvalab), YERVOY® (ipilumumab), and BAVENCIO® (avelumab), or any combination thereof.

Any anti-angiogenic agent can be used in conjunction with the polypeptides, antibodies, or antigen-binding fragments thereof, described herein. In some embodiments, the anti-angiogenic agent is a VEGF antagonist or another VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof. Alternately, or in addition, an anti-VEGF antibody may be co-administered to the patient.

The amount of the polypeptides, antibodies, and antigen-binding fragments thereof, described herein administered can depend upon a variety of factors including, but not limited to, the particular type of solid tumor treated, the stage of the solid tumor being treated, the mode of administration, the frequency of administration, the desired therapeutic benefit, and other parameters such as the age, weight and other characteristics of the patient. Determination of dosages effective to provide therapeutic benefit for specific modes and frequency of administration is within the capabilities of those skilled in the art. Dosages effective to provide therapeutic benefit can be estimated initially from in vivo animal models or clinical trials.

In some embodiments, the polypeptides, antibodies, or antigen-binding fragments thereof, described herein are provided as a lyophilized powder in a vial. The vials can contain about 100 mg, about 125 mg, about 150 mg, about 200 mg, about 250 mg, about 300 mg, or about 400 mg of the polypeptide fragments the antibodies, or antigen-binding fragments thereof. Prior to administration, the lyophilized powder can be reconstituted with sterile water for injection (SWFI) or other suitable medium to provide a solution containing the polypeptides, antibodies, and antigen-binding fragments thereof, described herein. In some embodiments, the resulting reconstituted solution is further diluted with saline or other suitable medium for infusion and administered via, for example, an IV infusion twice every 7 days, once every 7 days, once every 14 days, once every 21 days, once every 28 days, once every 35 days, once every 42 days, once every 49 days, or once every 56 days. In some embodiments, for the first cycle, the infusion occurs over 90 minutes. In some embodiments, subsequent infusions are over 60 minutes.

In some embodiments, the polypeptides, antibodies, and antigen-binding fragments thereof, described herein can be administered as an IV infusion once every 7 days at about 0.1 mg/kg, about 0.5 mg/kg, about 1.0 mg/kg, about 2.0 mg/kg, about 3.0 mg/kg, about 4.0 mg/kg, about 5.0 mg/kg, about 6.0 mg/kg, about 8.0 mg/kg, or about 10.0 mg/kg. In some embodiments, the polypeptides, antibodies, and antigen-binding fragments thereof, described herein can be administered as an IV infusion once every 14 days at about 0.1 mg/kg, about 0.5 mg/kg, about 1.0 mg/kg, about 2.0 mg/kg, about 3.0 mg/kg, about 4.0 mg/kg, about 5.0 mg/kg, about 6.0 mg/kg, about 8.0 mg/kg, or about 10.0 mg/kg. In some embodiments, the polypeptides, antibodies, and antigen-binding fragments thereof, described herein can be administered as an IV infusion once every 21 days at about 0.1 mg/kg, about 0.5 mg/kg, about 1.0 mg/kg, about 2.0 mg/kg, about 3.0 mg/kg, about 4.0 mg/kg, about 5.0 mg/kg, about 6.0 mg/kg, about 8.0 mg/kg, or about 10.0 mg/kg. In some embodiments, the polypeptides, antibodies, and antigen-binding fragments thereof, described herein can be administered as an IV infusion once every 28 days at about 0.1 mg/kg, about 0.5 mg/kg, about 1.0 mg/kg, about 2.0 mg/kg, about 3.0 mg/kg, about 4.0 mg/kg, about 5.0 mg/kg, about 6.0 mg/kg, about 8.0 mg/kg, or about 10.0 mg/kg.

In some embodiments, the polypeptides, antibodies, and antigen-binding fragments thereof, described herein can be administered in an amount from about 50 μg to about 1,000 mg, from about 100 μg to about 500 mg, from about 250 μg to about 100 mg, from about 500 μg to about 50 mg, from about 1 mg to about 40 mg, from about 5 mg to about 25 mg, or from about 10 mg to about 20 mg.

When administered adjunctive to or with other agents, such as other chemotherapeutic agents, the polypeptides, antibodies, and antigen-binding fragments thereof, described herein can be administered on the same schedule as the other agent(s), or on a different schedule. When administered on the same schedule, the polypeptides, antibodies, and antigen-binding fragments thereof, described herein can be administered before, after or concurrently with the other agent, In some embodiments, where the polypeptides, antibodies, and antigen-binding fragments thereof, described herein are administered adjunctive to, or with, standards of care, the polypeptides, antibodies, and antigen-binding fragments thereof, can be initiated prior to commencement of the standard therapy, for example one day, several days, one week, several weeks, one month, or even several months before commencement of standard of care therapy. In some embodiments, where the polypeptides, antibodies, and antigen-binding fragments thereof, described herein are administered adjunctive to, or with, standards of care, the polypeptide, antibodies, and antigen-binding fragments thereof, described herein can be initiated after commencement of the standard therapy, for example one day, several days, one week, several weeks, one month, or even several months after commencement of standard of care therapy.

The dosing schedule for subcutaneous administration can vary from once every six months to daily depending on a number of clinical factors, including the type of disease, severity of disease, and the patient's sensitivity to the polypeptide fragments, the antibodies, or antigen-binding fragments thereof, described herein.

The present disclosure also provides methods of inducing a biological process in a human cell comprising administering to the human cell any of the NetG1 polypeptides or NGL-1 polypeptides described herein. In some embodiments, the NetG1 polypeptide or NGL-1 polypeptide is present within a composition comprising a pharmaceutically acceptable carrier.

The present disclosure also provides methods of inducing a biological process in a human cell comprising administering to the human cell any of the antibodies, or antigen-binding fragments thereof, described herein that bind to any of the NetG1 polypeptides or NGL-1 polypeptides described herein. In some embodiments, the antibodies, or antigen-binding fragments thereof, are present within a composition comprising a pharmaceutically acceptable carrier.

In some embodiments, the biological process is: inhibiting NetG1 interaction with NGL1; inhibiting NGL1 engagement with NetG1; inhibiting rescue of starvation-induced death of a cancer cell; inhibiting activation of immunosuppressive cells; preventing inhibition of immunogenic cells; altering extracellular matrix production; altering amino acid secretion; altering metabolism of glutamate or glutamine dependent products; preventing immunosuppressive cells from maintaining pro-tumorigenic cells; preventing secretion of immunosuppressive factors; and/or preventing communication between any one or more of neural cells, fibroblastic cells, immune cells, and tumor cells. In some embodiments, the biological process is inhibiting NetG1 interaction with NGL1. In some embodiments, the biological process is inhibiting NGL1 engagement with NetG1. In some embodiments, the biological process is inhibiting rescue of starvation-induced death of a cancer cell. In some embodiments, the biological process is inhibiting activation of immunosuppressive cells. In some embodiments, the biological process is preventing inhibition of immunogenic cells. In some embodiments, the biological process is altering extracellular matrix production. In some embodiments, the biological process is altering amino acid secretion. In some embodiments, the biological process is altering metabolism of glutamate or glutamine dependent products. In some embodiments, the biological process is preventing immunosuppressive cells from maintaining pro-tumorigenic cells. In some embodiments, the biological process is preventing secretion of immunosuppressive factors. In some embodiments, the biological process is preventing communication between any one or more of neural cells, fibroblastic cells, immune cells, and tumor cells. In some embodiments, the biological process is promoting activation of anti-tumor immunity. In some embodiments, the biological process is preventing neural communication with any cell in the microenvironment or tumor cells.

In some embodiments, the polypeptides, antibodies, and antigen-binding fragments thereof, described herein are derivatized. For example, the derivatized antibodies can be antibodies modified by glycosylation, acetylation, pegylation, phosphorylation, amidation, derivatization by known protecting/blocking groups, proteolytic cleavage, linkage to a cellular ligand or other protein, and the like. Any of numerous chemical modifications can be carried out by known techniques, including, but not limited to, specific chemical cleavage, acetylation, formylation, metabolic synthesis of tunicamycin, and the like. In addition, the derivative can contain one or more non-natural amino acids, such as using ambrx technology (see, Wolfson, Chem. Biol., 2006, 13, 1011-1012).

In some embodiments, the polypeptides, antibodies, and antigen-binding fragments thereof, described herein comprises a modification. In some embodiments, the modification minimizes conformational changes during the shift from displayed to secreted forms of the antibody or antigen-binding fragment. It is to be understood by a skilled artisan that the modification can be a modification known in the art to impart a functional property that would not otherwise be present if it were not for the presence of the modification. The present disclosure provides antibodies which are differentially modified during or after translation, e.g., by pegylation, glycosylation, acetylation, phosphorylation, amidation, derivatization by known protecting/blocking groups, proteolytic cleavage, linkage to an antibody molecule, another protein or other cellular ligand, etc. Any of numerous chemical modifications may be carried out by known techniques including, but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

Additional post-translational modifications include, for example, N-linked or O-linked carbohydrate chains, processing of N-terminal or C-terminal end(s), attachment of chemical moieties to the amino acid backbone, chemical modifications of N-linked or O-linked carbohydrate chains, and addition or deletion of an N-terminal methionine residue as a result of prokaryotic host cell expression.

In some embodiments, the modification is an N-terminus modification. In some embodiments, the modification is a C-terminal modification. In some embodiments, the modification is an N-terminus biotinylation. In some embodiments, the modification is a C-terminus biotinylation. In some embodiments, the secretable form of the antibody or antigen-binding fragment comprises an N-terminal modification that allows binding to an Immunoglobulin hinge region. In some embodiments, the Ig hinge region is an IgA hinge region. In some embodiments, the secretable form of the antibody or antigen-binding fragment comprises an N-terminal modification that allows binding to an enzymatically biotinylatable site. In some embodiments, the secretable form of the antibody or antigen-binding fragment comprises a C-terminal modification that allows binding to an enzymatically biotinylatable site. In some embodiments, biotinylation of the site functionilizes the site to bind to any surface coated with streptavidin, avidin, avidin-derived moieties, or a secondary reagent. In some embodiments, the secondary reagent is a protein, a peptide, a carbohydrate, or a glycoprotein.

In some embodiments, the polypeptides, antibodies, and antigen-binding fragments thereof, described herein can be modified for increased expression in heterologous hosts. In some embodiments, the polypeptides, antibodies, and antigen-binding fragments thereof, described herein can be modified for increased expression in and/or secretion from heterologous host cells. In some embodiments, the polypeptides, antibodies, and antigen-binding fragments thereof, described herein can be modified for increased expression in bacteria, such as *E. coli*. In some embodiments, the polypeptides, antibodies, and antigen-binding fragments thereof, described herein can be modified for increased expression in yeast (Kieke et al., Proc. Nat'l Acad. Sci. USA, 1999, 96, 5651-5656). In some embodiments, the polypeptides, antibodies, and antigen-binding fragments thereof, described herein can be modified for increased expression in insect cells. In some embodiments, the polypeptides, antibodies, and antigen-binding fragments thereof, described herein can be modified for increased expression in mammalian cells, such as CHO cells.

In some embodiments, the polypeptides, antibodies, and antigen-binding fragments thereof, described herein can be modified to increase stability during production. In some embodiments, the polypeptides, antibodies, and antigen-binding fragments thereof, described herein can be modified to replace one or more amino acids such as asparagine or glutamine that are susceptible to nonenzymatic deamidation with amino acids that do not undergo deamidation (Huang et al., Anal. Chem., 2005, 77, 1432-1439). In some embodiments, the polypeptides, antibodies, and antigen-binding fragments thereof, described herein can be modified to replace one or more amino acids that is susceptible to oxidation, such as methionine, cysteine or tryptophan, with an amino acid that does not readily undergo oxidation. In some embodiments, the polypeptides, antibodies, and antigen-binding fragments thereof, described herein can be modified to replace one or more amino acids that is susceptible to cyclization, such as asparagine or glutamic acid, with an amino acid that does not readily undergo cyclization.

In some embodiments, the polypeptides, antibodies, and antigen-binding fragments thereof, described herein can be conjugated to an effector moiety. In some embodiments, the polypeptides, antibodies, and antigen-binding fragments thereof, described herein can be modified by the covalent attachment of any type of molecule, such that covalent attachment does not interfere with binding to NetG1 or NGL-1. In some embodiments, the effector moiety is a detectable label, a cytotoxic agent, a chemotherapeutic agent, or a nucleic acid molecule. The effector moiety can also be an antineoplastic agent, a drug, a toxin, a biologically active protein (such as an enzyme), another antibody or antibody fragment, a synthetic or naturally occurring polymer, a nucleic acid molecule, a radionuclides (such as radioiodide), a radioisotope, a chelated metal, a nanoparticle, or a reporter group (such as a fluorescent compound or a compound which can be detected by NMR or ESR spectroscopy).

In some embodiments, the polypeptides, antibodies, and antigen-binding fragments thereof, described herein can be conjugated to a cytotoxic agent, a radionuclide, or a drug moiety to modify a particular biological response. The effector moiety can be a protein or polypeptide, such as, for example, a toxin (such as abrin, ricin A, saporin, *Pseudomonas* exotoxin, diphtheria toxin, ethidium bromide or PE40, PE38, gelonin, RNAse, peptide nucleic acids (PNAs), ribosome inactivating protein (RIP) type-1 or type-2, pokeweed anti-viral protein (PAP), bryodin, momordin, chemotherapeutic agents, and bouganin), a signaling molecule (such as α-interferon, β-interferon, nerve growth factor, platelet derived growth factor or tissue plasminogen activator), a thrombotic agent or an anti-angiogenic agent (such as, angiostatin or endostatin) or a biological response modifier such as a cytokine or growth factor (such as, interleukin-1 (IL-1), interleukin-2 (IL-2), interleukin-6 (IL-6), granulocyte macrophage colony stimulating factor (GM-CSF), granulocyte colony stimulating factor (G-CSF), or nerve growth factor (NGF)).

In some embodiments, the cytotoxic agent is a small molecule, a prodrug, a maytansinoid, or a toxin. In some embodiments, the antibody, or antigen-binding fragment thereof, comprises from 3 to 5 maytansinoid molecules per antibody, or antigen-binding fragment thereof. In some embodiments, the maytansinoid is conjugated to the antibody, or antigen-binding fragment thereof, by a chemical linker chosen from N-succinimidyl-3-(2-pyridyldithio) propionate, N-succinimidyl-4-(2-pyridylthio)pentanoate (SPP), and succinimidyl-4-(N-maleimidomethyl)cyclohexanel-1-carboxylate. In some embodiments, the cytotoxic agent is taxol, cytochalasin B, gramicidin D, ethidium bromide, emetine, mitomycin, etoposide, tenoposide, vincristine, vinblastine, colchicin, doxorubicin, daunorabicin, dihydroxy anthracin dione, mitoxantrone, mithramycin, actinomycin D, 1-dehydrotestosterone, glucocorticoids, procaine, tetracaine, lidocaine, propranolol, or puromycin.

In some embodiments, the detectable label is radioactive compound, a fluorescent compound, a chromophore, an enzyme, an imaging agent, a metal ion, or a substrate. In some embodiments, a fluorescent moiety includes, but is not limited to, fluorescein, fluorescein isothiocyanate, rhodamine, 5-dimethylamine-1-napthalenesulfonyl chloride, phycoerythrin and the like. Useful enzymatic labels include, but are not limited to, alkaline phosphatase, horseradish peroxidase, glucose oxidase, and the like.

In some embodiments, the effector moiety is an antimetabolite (such as, methotrexate, 6-mercaptopurine, 6-thioguanine, cytarabine, and 5-fluorouracil decarbazine), an alkylating agent (such as, mechlorethamine, thioepa chlorambucil, melphalan, carmustine (BSNU) and lomustine (CCNU), cyclothosphamide, busulfan, dibromomannitol, streptozotocin, mitomycin C5 and cisdichlorodiamine platinum (II) (DDP) cisplatin), an anthracycline (such as, daunorubicin (formerly daunomycin) and doxorubicin), an antibiotic (such as, dactinomycin (formerly actinomycin), bleomycin, mithramycin, anthramycin (AMC), calicheamicins or duocarmycins), or an anti-mitotic agent (such as, vincristine and vinblastine).

In some embodiments, the radionuclides is, but is not limited to, $^{13}$N, $^{18}$F, $^{32}$P, $^{64}$Cu, $^{66}$Ga, $^{67}$Ga, $^{68}$Ga, $^{67}$Cu, $^{77}$Br, $^{80m}$Br, $^{82}$Rb, $^{86}$Y, $^{90}$Y, $^{95}$Ru, $^{97}$Ru, $^{99m}$Tc, $^{103}$Ru, $^{105}$Ru, $^{111}$In, $^{113m}$In, $^{113}$Sn, $^{121m}$Te, $^{122m}$Te, $^{125m}$Te, $^{123}$I, $^{124}$I, $^{125}$I, $^{126}$I, $^{131}$I, $^{133}$I, $^{165}$Tm, $^{167}$Tm, $^{168}$Tm, $^{177}$Lu, $^{186}$Re, $^{188}$Re, $^{195m}$Hg, $^{211}$At, $^{212}$Bi, $^{213}$Bi, and $^{225}$Ac.

In some embodiments, the chemotherapeutic agent is cisplatin, carboplatin, oxaliplatin, nedaplatin, triplatin tetranitrate, phenanthriplatin, picoplatin, satraplatin, methotrexate, vincristine, doxorubicin, tunicamycin, oligomycin, bortezomib, MG132, 5-flurouracil, sorafenib, flavopiridol, gemcitabine, taxol, mercaptopurine, thioguanine, hydroxyurea, cytarabine, mitomycin, cyclophosphamide, ifosfamide, nitrosourea, dacarbazine, procarbizine, an etoposide, a campathecin, bleomycin, idarubicin, daunorubicin, dactinomycin, distamycin A, etidium, netropsin, auristatin, amsacrine, prodigiosin, bortexomib, pibenzimol, tomaymycin, duocarmycin SA, plicamycin, mitoxantrone, asparaginase, vinblastine, vinorelbine, paclitaxel, docetaxel, CPT-11, gleevec, erlotinib, gefitinib, ibrutinib, crizotinib, ceritinib, lapatinib, navitoclax, or regorafenib.

In some embodiments, the polypeptides, antibodies, and antigen-binding fragments thereof, described herein can be conjugated to a small molecule toxin. In some embodiments, the polypeptides, antibodies, and antigen-binding fragments thereof, described herein can be conjugated to a dolostatin or a dolastatin peptidic analog or derivative, such as an auristatin (see, U.S. Pat. Nos. 5,635,483 and 5,780,588). The dolastatin or auristatin drug moiety can be attached to the antibody through its N-terminus, C-terminus or internally (see, PCT Publication WO 02/088172). Exemplary auristatin molecules include the N-terminus linked monomethyl-auristatin drug moieties DE and DF, as disclosed in U.S. Pat. No. 7,498,298 (disclosing linkers and methods of preparing monomethylvaline compounds such as MMAE and MMAF conjugated to linkers).

Antibodies, or antigen-binding fragments thereof, can also be conjugated to liposomes for targeted delivery (see, Park et al., Adv. Pharmacol., 1997, 40, 399-435; and Marty et al., Methods Molec. Med., 2004, 109, 389-401).

In some embodiments, the polypeptides, antibodies, and antigen-binding fragments thereof, described herein can be attached to poly(ethyleneglycol) (PEG) moieties. In some embodiments, the polypeptides, antibodies, and antigen-binding fragments thereof, described herein and the PEG moieties can be attached through any available amino acid side-chain or terminal amino acid functional group located in the polypeptides, antibodies, and antigen-binding fragments thereof, described herein such as, for example, any free amino, imino, thiol, hydroxyl or carboxyl group. Such amino acids can occur naturally in the polypeptides, antibodies, and antigen-binding fragments thereof, described herein can be engineered using recombinant DNA methods (see, U.S. Pat. No. 5,219,996). Multiple sites can be used to attach two or more PEG moieties. PEG moieties can be covalently linked through a thiol group of at least one cysteine residue located in the polypeptides, antibodies, and antigen-binding fragments thereof, described herein. Where a thiol group is used as the point of attachment, appropriately activated effector moieties, for example, thiol selective derivatives such as maleimides and cysteine derivatives, can be used.

In some embodiments, the antibodies, or antigen-binding fragments thereof, can comprise a modified Fab' fragment which is PEGylated. The PEG moiety can be attached to a cysteine in the hinge region. In some embodiments, a PEG-modified Fab' fragment has a maleimide group covalently linked to a single thiol group in a modified hinge region. A lysine residue can be covalently linked to the maleimide group and to each of the amine groups on the lysine residue can be attached a methoxypoly(ethyleneglycol) polymer having a molecular weight of approximately 20,000 Da. The total molecular weight of the PEG attached to the Fab' fragment can be approximately 40,000 Da.

The present disclosure also provides pharmaceutical compositions comprising the polypeptides, antibodies, and antigen-binding fragments thereof, described herein and a pharmaceutically acceptable carrier. In some embodiments, the pharmaceutical compositions further comprise a tonicity agent, a surfactant, a preservative, and/or a buffer system having a pH of about 4.0 to about 8.0. In some embodiments, the pharmaceutical compositions further comprise one or more additional therapeutic agents, such as the combination therapeutic agents described herein. In some embodiments, the pharmaceutical composition is a liquid pharmaceutical composition.

In some embodiments, the pharmaceutical compositions can be presented in unit dose forms containing a predetermined amount of the polypeptides, antibodies, and antigen-binding fragments thereof, described herein per dose. Pharmaceutically acceptable carriers for use in the pharmaceutical compositions can take a wide variety of forms depending on the condition to be treated or route of administration.

Pharmaceutical compositions comprising the polypeptides, antibodies, and antigen-binding fragments thereof, described herein can be prepared for storage as lyophilized formulations or aqueous solutions by mixing the polypeptides, antibodies, and antigen-binding fragments thereof, described herein having the desired degree of purity with optional pharmaceutically acceptable carriers, excipients or stabilizers typically employed in the art (all of which are referred to herein as "carriers") such as, for example, buffering agents, stabilizing agents, preservatives, isotonifiers, non-ionic detergents, antioxidants, and other miscellaneous additives.

Buffering agents help to maintain the pH in the range that approximates physiological conditions. They can be present at concentration ranging from about 2 mM to about 50 mM. Suitable buffering agents for use in the pharmaceutical compositions described herein can include both organic and inorganic acids and salts thereof, such as citrate buffers (such as, monosodium citrate-disodium citrate mixture, citric acid trisodium citrate mixture, citric acid-monosodium citrate mixture, and the like), succinate buffers (such as, succinic acidmonosodium succinate mixture, succinic acid-sodium hydroxide mixture, succinic acid-disodium succinate mixture, and the like), tartrate buffers (such as, tartaric acid-sodium tartrate mixture, tartaric acid-potassium tartrate mixture, tartaric acid-sodium hydroxide mixture, and the like), fumarate buffers (such as, fumaric acid-monosodium fumarate mixture, fumaric acid-disodium fumarate mixture, monosodium fumarate-disodium fumarate mixture, and the like), gluconate buffers (such as, gluconic acid-sodium gluconate mixture, gluconic acid-sodium hydroxide mixture, gluconic acid-potassium glyuconate mixture, and the like), oxalate buffer (such as, oxalic acid-sodium oxalate mixture, oxalic acid-sodium hydroxide mixture, oxalic acid-potassium oxalate mixture, and the like), lactate buffers (such as, lactic acid-sodium lactate mixture, lactic acid-sodium hydroxide mixture, lactic acid-potassium lactate mixture, and the like) and acetate buffers (such as, acetic acid-sodium acetate mixture, acetic acid-sodium hydroxide mixture, and the like). Additionally, phosphate buffers, histidine buffers and trimethylamine salts, such as Tris, can be used.

Preservatives can be added to retard microbial growth, and can be added in amounts ranging from 0.2%-1% (w/v). Suitable preservatives include, but are not limited to, phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers, sometimes known as "stabilizers", can be added to ensure isotonicity of liquid compositions of the present disclosure and include, but are not limited to, polhydric sugar alcohols, for example, trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers include, but are not limited to, polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, $\alpha$-monothioglycerol and sodium thio sulfate; low molecular weight polypeptides (e.g., peptides of 10 residues or fewer); proteins such as human serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can also be added to pharmaceutical compositions help solubilize the polypeptides, antibodies, and antigen-binding fragments thereof, described herein as well as to protect the polypeptides, antibodies, and antigen-binding fragments thereof, described herein against agitation-induced aggregation, which also permits the formulation to be exposed to shear surface stressed without causing denaturation of the proteins. Suitable non-ionic surfactants include, but are not limited to, polysorbates (20, 80, etc.), polyoxamers (184, 188, etc.). Pluronic polyols, polyoxyethylene sorbitan monoethers (TWEEN™-20, TWEEN™-80, and the like). Nonionic surfactants can be present in a range of about 0.05 mg/mL to about 1.0 mg/mL, for example, about 0.07 mg/mL to about 0.2 mg/mL.

Additional excipients, such as, bulking agents (such as, starch), chelating agents (such as, EDTA), antioxidants (such as, ascorbic acid, methionine, and vitamin E), and cosolvents can also be added to the pharmaceutical compositions.

Liposomes, or extracellular vesicles (natural or artificial), provide a means to deliver the polypeptides, antibodies, and/or antigen-binding fragments thereof described herein to a subject intravenously, intraperitoneally, intrathecally, intramuscularly, subcutaneously, or via oral administration, inhalation, or intranasal administration. Depending on the method of preparation, liposomes and extracellular vesicles can be unilamellar or multilamellar, and liposomes and extracellular vesicles can vary in size with diameters ranging from 0.02 μm to greater than 10 μm.

In some embodiments, the polypeptides, antibodies, and/or antigen-binding fragments thereof described herein can be encapsulated in polymer microspheres. Microspheres can be prepared from degradable polymers such as poly(lactide-co-glycolide) (PLG), polyanhydrides, poly(ortho esters), nonbiodegradable ethylvinyl acetate polymers, in which proteins are entrapped in the polymer (Gombotz and Pettit, Bioconjugate Chem., 1995, 6, 332; Ranade, "Role of Polymers in Drug Delivery," in Drug Delivery Systems, Ranade and Hollinger (eds.), pages 51-93 (CRC Press 1995); Roskos and Maskiewicz, "Degradable Controlled Release Systems Useful for Protein Delivery," in. degree. Protein Delivery: Physical Systems, Sanders and Hendren (eds.), pages 45-92 (Plenum Press 1997); Bartus et al., Science, 1998, 281, 1161; Putney and Burke, Nature Biotechnology, 1998, 16, 153; and Putney, Cum Opin. Chem. Biol., 1998, 2, 548). Polyethylene glycol (PEG)-coated nanospheres can also provide carriers for intravenous administration of therapeutic proteins (see, for example, Gref et al., Pharm. Biotechnol., 1997, 10, 167).

In some embodiments, the polypeptides, antibodies, and antigen-binding fragments thereof, described herein bind to NetG1 or NGL-1 with a $K_A$ ($k_{on}/k_{off}$) of at least about $10^{10}$ $M^{-1}$, at least about $4 \times 10^{11}$ $M^{-1}$, at least about $10^{11}$ $M^{-1}$, at least about $4 \times 10^{12}$ $M^{-1}$, at least about $10^{12}$ $M^{-1}$, at least about $4 \times 10^{13}$ $M^{-1}$, at least about $10^{13}$ $M^{-1}$, at least about $4 \times 10^{14}$ $M^{-1}$, at least about $10^{14}$ $M^{-1}$, at least about $4 \times 10^{15}$ $M^{-1}$, or at least about $10^{15}$ $M^{-1}$, or with a $K_A$ of any range from and to any pair of the foregoing values (such as, from about $4 \times 10^{11}$ $M^{-1}$ to about $4 \times 10^{13}$ $M^{-1}$ or from about $4 \times 10^{12}$ $M^{-1}$ to about $4 \times 10^{15}$ $M^{-1}$).

In some embodiments, the polypeptides, antibodies, and antigen-binding fragments thereof, described herein bind to NetG1 or NGL-1 with a $K_D$ ($k_{off}/k_{on}$) of about $10^{-10}$ or less, about $4 \times 10^{-11}$ M or less, about $10^{-11}$ M or less, about $4 \times 10^{-12}$ M or less, about $10^{-12}$ M or less, about $4 \times 10^{13}$ M or less, about $10^{-13}$ M or less, about $4 \times 10^{14}$ M or less, about $10^{-14}$ M or less, about $4 \times 10^{-15}$ M or less, or about $10^{-15}$ M or less, or with a $K_D$ of any range from and to any pair of the foregoing values (such as, from about $4 \times 10^{-11}$ M to about $4 \times 10^{-13}$ M or from about $4 \times 10^{-12}$ M to about $4 \times 10^{-15}$ M). In some embodiments, the $K_D$ ($k_{off}/k_{on}$) value is determined by assays well known in the art, such as ELISA, isothermal titration calorimetry (ITC), fluorescent polarization assay or any other biosensors such as BIAcore.

In some embodiments, the polypeptides, antibodies, and antigen-binding fragments thereof, described herein bind to NetG1 or NGL-1 and inhibit the binding of NetG1 and NGL-1 at an $IC_{50}$ of less than about 0.02 nM, less than about 0.01 nM, less than about 0.005 nM, less than about 0.002 nM, less than about 0.001 nM, less than about $5 \times 10^{-4}$ nM, less than about $2 \times 10^{-4}$ nM, less than about $1 \times 10^{-4}$ nM, less than about $5 \times 10^{-5}$ nM, less than about $2 \times 10^{-5}$ nM, less than about $1 \times 10^{-4}$ nM, less than about $5 \times 10^{-6}$ nM, less than about $2 \times 10^{-6}$ nM, less than about $1 \times 10^{-6}$ nM, less than about $5 \times 10^{-7}$ nM, less than about $2 \times 10^{-7}$ nM, or less than about $1 \times 10^{-7}$ nM, or with an $IC_{50}$ of any range from and to any pair of the foregoing values (such as, from about 0.02 nM to about $2 \times 10^{-5}$ nM, or from about $5 \times 10^{-5}$ nM to about $1 \times 10^{-7}$ nM). The $IC_{50}$ can be measured according to methods such as ELISA.

In some embodiments, the polypeptides, antibodies, and antigen-binding fragments thereof, described herein can be used, for example, in conjunction with compound screening assays, for the evaluation of the effect of pharmaceutical agents on the expression and/or activity of the NetG1 or NGL-1 gene product. Additionally, the polypeptides, antibodies, and antigen-binding fragments thereof, described herein can be used in conjunction with gene therapy techniques to, for example, evaluate the success of transfection of normal and/or engineered NetG1 or NGL-1-expression.

The polypeptides, antibodies, and antigen-binding fragments thereof, described herein can also be used to detect expression of NetG1 or NGL-1 in particular cells, tissues, or serum; or to monitor the development or progression of an immunologic response as part of a clinical testing procedure to, for example, determine the efficacy of a particular treatment regimen. Detection can be facilitated by coupling the polypeptides, antibodies, and antigen-binding fragments thereof, described herein to a detectable substance. Examples of detectable substances include, but are not limited to, various enzymes, prosthetic groups, fluorescent materials (such as, fluorescein and rhodamine and their derivatives), luminescent materials, bioluminescent materials, optical agents (such as, derivatives of phorphyrins, anthraquinones, anthrapyrazoles, perylenequinones, xan-thenes, cyanines, acridines, phenoxazines and phenothiaz-ines), radioactive materials, positron emitting metals using various positron emission tomographies, and nonradioactive paramagnetic metal ions (such as, Gd(III), Eu(III), Dy(III), Pr(III), Pa(IV), Mn(II), Cr(III), Co(III), Fe(III), Cu(II), Ni(II), Ti(III), and V(IV)). The detectable substance can be coupled or conjugated either directly to the polypeptides, antibodies, and antigen-binding fragments thereof, described herein or indirectly, through an intermediate (such as, for example, a linker known in the art). Examples of enzymatic labels include, but are not limited to, luciferases (such as, firefly luciferase and bacterial luciferase; see, U.S. Pat. No. 4,737,456), luciferin, 2,3-dihydrophthalazin-ediones, malate dehydrogenase, urease, peroxidase such as horseradish peroxidase (HRPO), alkaline phosphatase, β-ga-lactosidase, acetylcholinesterase, glucoamylase, lysozyme, saccharide oxidases (such as, glucose oxidase, galactose oxidase, and glucose-6-phosphate dehydrogenase), hetero-cyclic oxidases (such as, uricase and xanthine oxidase), lactoperoxidase, microperoxidase, and the like. Examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rho-damine, dichlorotriazinylamine fluorescein, dansyl chloride or phycoerythrin; an example of a luminescent material includes, but are not limited to, luminol; examples of bioluminescent materials include, but are not limited to, luciferase, luciferin, and aequorin; and examples of suitable radioactive material include, but are not limited to, $^{125}$I, $^{131}$I, $^{111}$In or $^{99}$Tc.

The present disclosure also provides methods for detect-ing expression of NetG1 or NGL-1 on a cell, comprising contacting a biological sample from a patient using one or more of the polypeptides, antibodies, and antigen-binding fragments thereof, described herein (optionally conjugated to detectable moiety), and detecting whether or not the sample is positive for NetG1 or NGL-1 expression, or whether the sample has altered (such as, reduced or increased) expression as compared to a control sample. The biological sample can include biopsies of various tissues including, without limitation: skin, muscle, breast, prostate, cervical, ovarian, brain, testicular, and pulmonary. Cellular examples of biological samples include tumor cells, skin cells, muscle cells, blood cells, ovarian cells, brain cells, prostate cells, breast cells, testicular cells, cervical cells, and lung cells. The biological sample may also be a biological fluid.

In any of the methods described herein, the stroma can be isolated from any suitable tissue in the subject. The tissue can comprise pancreatic tissue (e.g., pancreatic stroma), kidney tissue (e.g., kidney stroma), or lung tissue (e.g., lung stroma). The tissue can comprise any tissue, including epithelial tissue, from any organ, having stroma. The tissue can be fibrotic, cancerous, or can be pre-cancerous, or can be suspected of being cancerous or pre-cancerous. The assess-ment of the stroma need not be related to cancer, for example, the stroma can be isolated for determining a fibrosis condition, including pulmonary or lung fibrosis, renal/kidney fibrosis, or pancreatic fibrosis. Stroma can be isolated from the tissue according to any suitable isolation technique. A biopsy can be used in some embodiments. For example, a surgical biopsy can be used, or a core needle biopsy can be used. In addition to or in the alternative to solid tissue sampling, the assessments of NetG1 and/or NGL-1 can be carried out in liquid samples, including liquid biopsies. Thus, in some embodiments, liquid biopsies can be obtained from the subject.

A proper control (e.g., a sample from a subject or a group of subjects who are either known as having NetG1 or NGL-1-expressing cancer or tumor or not having NetG1 or NGL-1-expressing cancer or tumor) can be used in the assays described herein. A person skilled in the art will appreciate that the difference in the amount of antibody-antigen complex will vary depending on the control. For example, if the control is known to have NetG1 or NGL-1-expressing cancer or tumor, then less measurable antibody-antigen complex in the test sample as compared to the control indicates that the subject does not have NetG1 or NGL-1-expressing cancer or tumor or that they have less of an extent of NetG1 or NGL-1-expressing cancer or tumor. If the control is known to have NetG1 or NGL-1-expressing cancer or tumor, then equal or greater measurable antibody-antigen complex in the test sample as compared to the control indicates that the subject has NetG1 or NGL-1-expressing cancer or tumor. If the control is known not to have NetG1 or NGL-1-expressing cancer or tumor, then less or equal measurable antibody-antigen complex in the test sample as compared to the control indicates that the subject does not have NetG1 or NGL-1-expressing cancer or tumor. If the control is known not to have NetG1 or NGL-1-expressing cancer or tumor, then greater measurable anti-body-antigen complex in the test sample as compared to the control indicates that the subject has NetG1 or NGL-1-expressing cancer or tumor.

The present disclosure also provides NetG1 or NGL-1 polypeptides, antibodies binding thereto, and antigen-bind-ing fragments thereof, for use in the treatment of a cancer or chronic fibrosis (or for use in the preparation of a medica-ment for treating a cancer or chronic fibrosis) in a human subject, wherein the NetG1 or NGL-1 polypeptides, anti-bodies binding thereto, and antigen-binding fragments thereof, are any of those described herein.

In order that the subject matter disclosed herein may be more efficiently understood, examples are provided below. It should be understood that these examples are for illustrative purposes only and are not to be construed as limiting the claimed subject matter in any manner. Throughout these examples, molecular cloning reactions, and other standard recombinant DNA techniques, were carried out according to methods described in Maniatis et al., Molecular Cloning-A Laboratory Manual, 2nd ed., Cold Spring Harbor Press (1989), using commercially available reagents, except where otherwise noted.

Using pancreatic ductal adenocarcinoma (PDAC) the experiments described herein assessed the potential dynamic manipulation of interaction between NetG1 and NGL-1. Without wishing to be bound by any particular theory, it is believed that the interaction of NetG1 expressed on the surface of associated fibroblasts (CAFs) or in extracellular vesicles (EVs) secreted by CAFs and NGL-1 expressed on cancer cells surfaces promotes formation of synapsis-like junctions between cancer cells and CAFs or CAF secreted EVs, and that these interaction rescue starvation-induced death of PDAC cancer cells. It is also believed, that inter-action of NetG1, present high levels in desmoplastic stroma and circulating extracellular vesicles, with NGL-1 expressed on the surface with immune cells, such as T-cells and NK cell prevents T-cell and NK cell activation, thereby suppressing host's immune response to tumor. Accordingly, it is believed that targeting NetG1/NGL-1 interaction in tumor stroma may promote both starvation-induced death of PDAC cancer cells and immune response to the tumor.

The results in the Examples below, and particularly in Examples 7-10, indicate that an antibody against NetrinG1 can phenocopy the loss of either NetrinG1 or NetrinG1 ligand and may serve as a therapeutic agent. The results shown below also indicate that the NetrinG1 ligand knockout mice can serve as a host which can limit the syngeneic/orthotopic growth of pancreatic cancer cells. The results below also indicate the two peptides demonstrated inhibitory activity and can thus also serve as therapeutic agents.

EXAMPLES

Example 1: Inhibition of NetG1/NGL Interaction Promotes Clustering

Treating CAF EVs with recombinant NGL1 (or anti-NetG1 antibody) or NetG1 enables small NetG1 positive (i.e., exomeres) or large (i.e., exosome) EV clustering, respectively (see, FIG. 1, Panels A-E). Small and large EVs did not show clustering in the absence of recombinant NGL1 or NetG1 treatment, suggesting that engagement between the two membrane-tethered proteins triggers a change (in this case clustering of vesicles). Treating CAFs with recombinant NGL1, thus engaging with NetG 1 in CAFs, resulted in the production of increased numbers of EVs and induced some clustering. Treatment with NetG1 only clusters exosomes (big *), treatment with NGL1 and NetG1 mostly clusters exomeres (small *). Together, these results indicate the possibility of a functional role associated with NetG1/NGL1 engagement.

Example 2: Recombinant NGL1 Induces Blebbing in Human CAFs

Figure 1A:
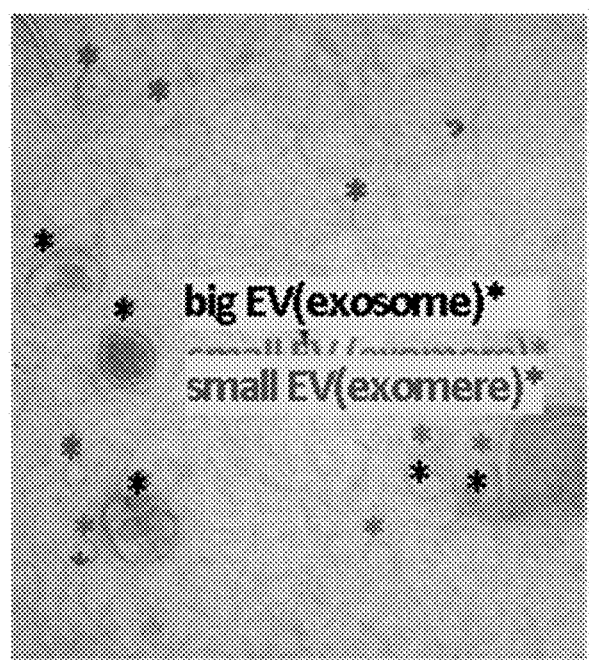
FIG. 1A shows untreated CAFs secreted EVs that were also untreated following their collection and did not form clusters.
Figure 1B:
FIG. 1B shows clustering of CAF-produced EVs was observed in EVs that were incubated (following their collection) with recombinant NGL1.
Figure 1B:
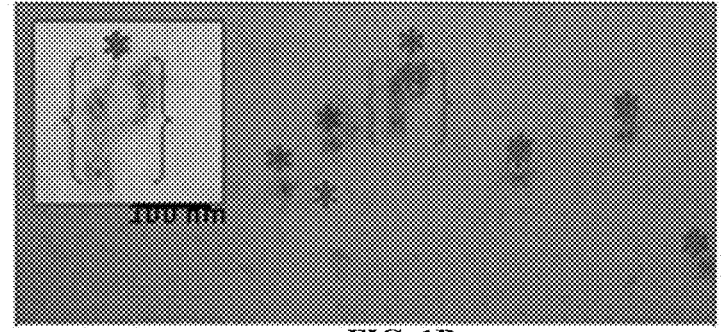
Figure 1C:
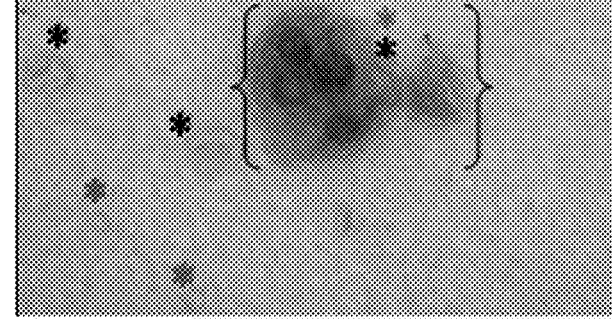
FIG. 1C shows clustering of CAF-produced EVs was also observed in EVs that were incubated (following their collection) with recombinant NetG1.
Figure 1D:
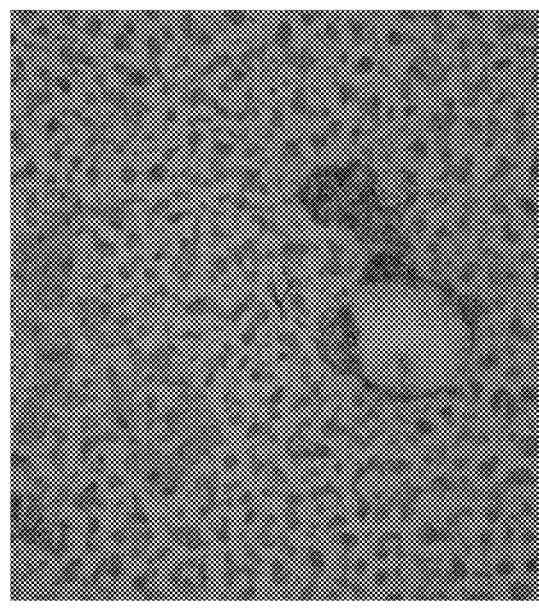
FIG. 1D shows CAFs treated with recombinant NGL1 produced clustered EVs.
Figure 1E:
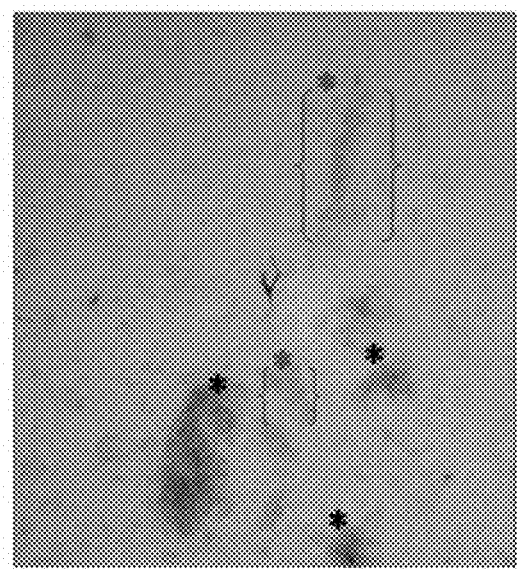
FIG. 1E shows clustering of CAF-produced EVs was also observed when EVs (or CAF during EV production; data not shown) were treated with anti-NetG1 antibody.
Figure 2A:
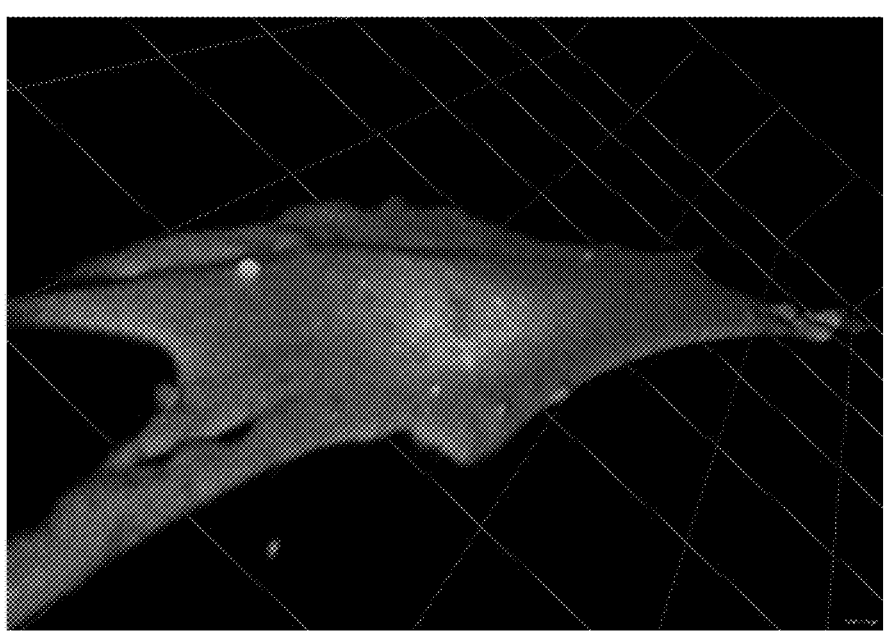
FIG. 2A shows a 3D-rendering of GFP-expressing CAFs to highlight the surface of untreated CAF.
Figure 2B:
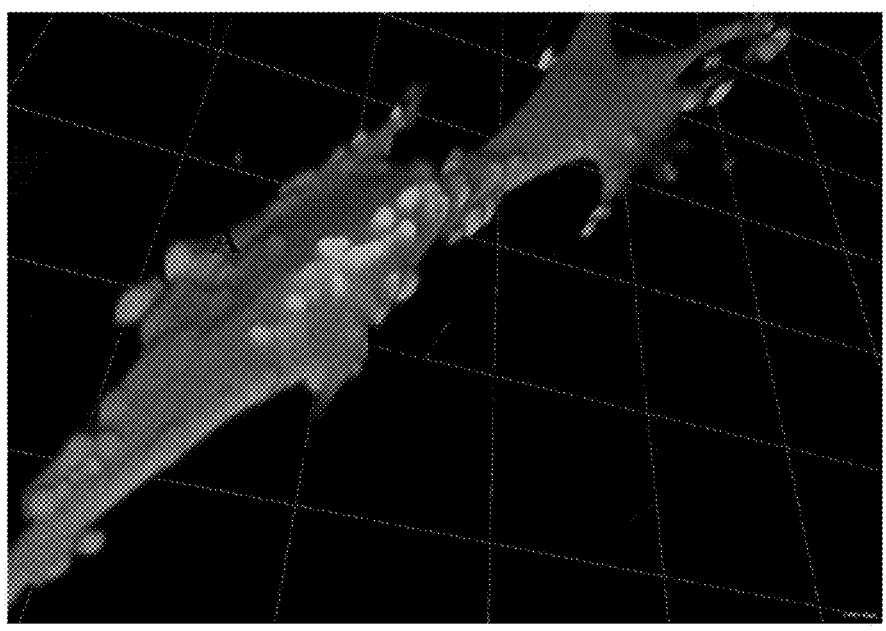
FIG. 2B shows a 3D-rendering of GFP-expressing CAFs treated with recombinant NGL1.

Treating CAFs with recombinant NGL1 under the 3D conditions that enable NetrinG1 expression in CAFs induced CAF blebbing (i.e., membrane ruffling or protruding) in response to treatment (see, FIG. 2, Panels A and B), mimicking the engagement NGL1 positive tumor cells. The phenotype is believed to indicate fibroblastic function after NGL1 engagement from other cells (like tumor cells). Similar effects were observed when cancer cells were co-cultured with CAFs using CAF-derived matrices as culturing scaffolds. The blebbing was not observed when the same treatment was used in NetG1 KO CAFs.

Figure 3A:
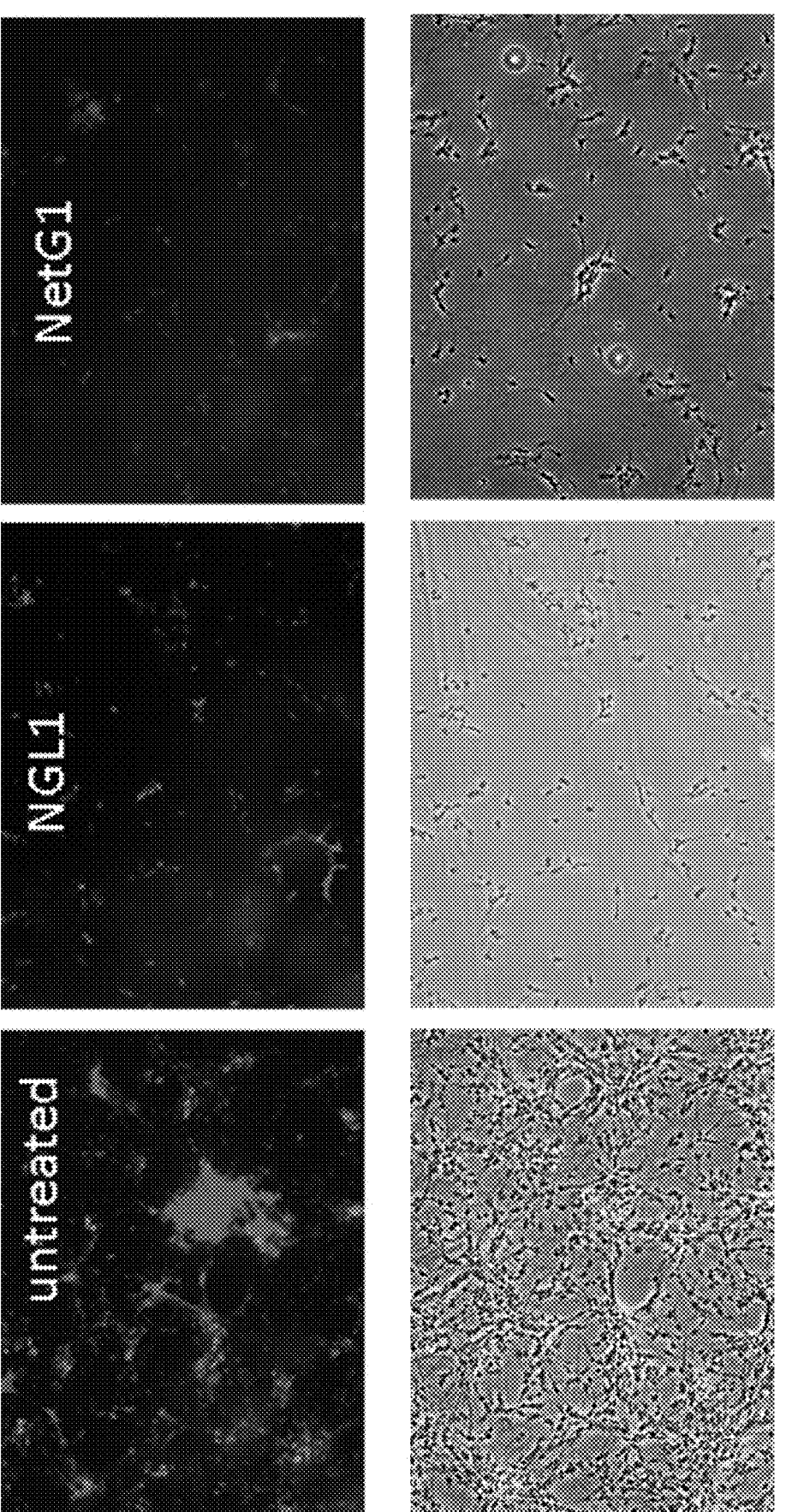
FIG. 3A shows virus infected neurons (shown in transmitted light in the bottom panels) cultured while untreated (left) or treated with recombinant NGL1 (middle) or NetG1 (right) to assess functional neural synapse-dependent virus infection (top panels) and neural morphology (bottom panels); virus infection was effectively propagated in the absence of treatment and affected more by treatment with recombinant NGL1 and NetG1, suggesting polarity of pre-/post-synaptic virus infection under these conditions.
Figure 3B:
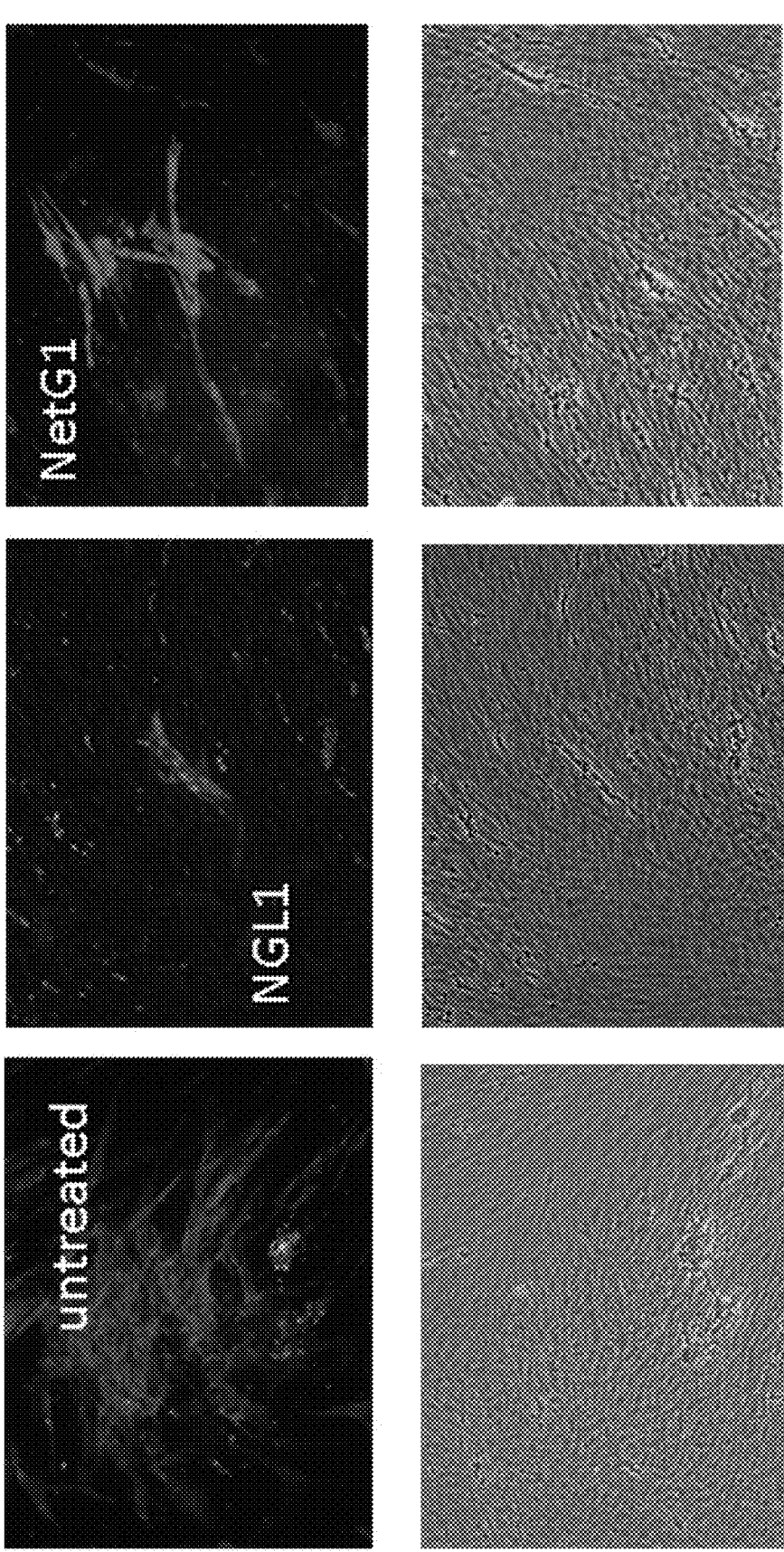
FIG. 3B shows the same experiment, as in FIG. 3A, conducted except that virus infected neurons were plated onto a CAF culture bed (evident in transmitted microscopy images shown in bottom panels) to assess heterotypic neuron-CAF functional synapse formation (evidenced by virus spread into CAFs) while untreated (left) or treated with recombinant NGL1 (middle) or NetG1 (right); effective virus spread in untreated cultures was prevented by recombinant NGL1 and NetG1 treatments, suggesting that preventing direct neuro-CAF engagement via NetG1/NGL1 effectively disrupts functional synapses as evident by blocking of virus spread.
Figure 3C:
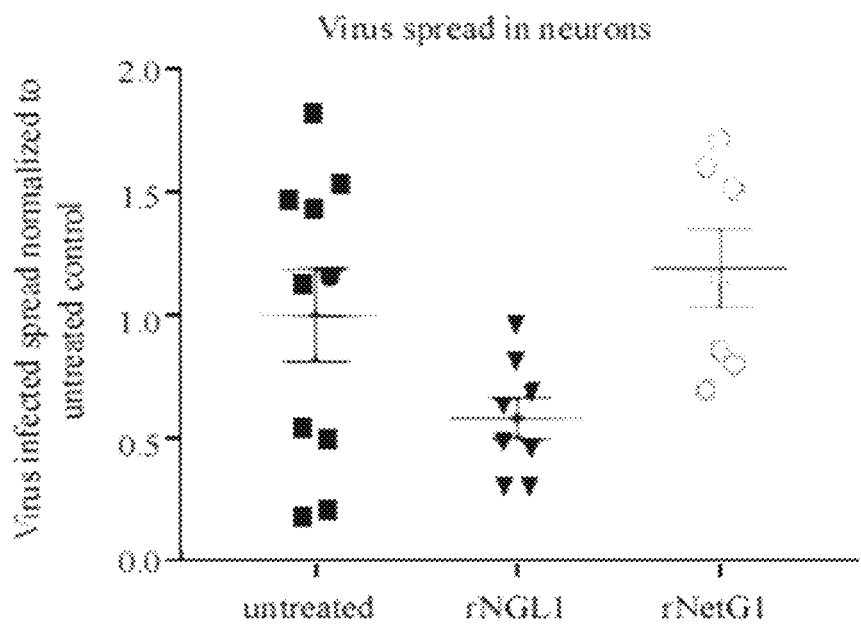
FIG. 3C shows a graphical representation of the data presented in FIG. 3A.
Figure 3D:
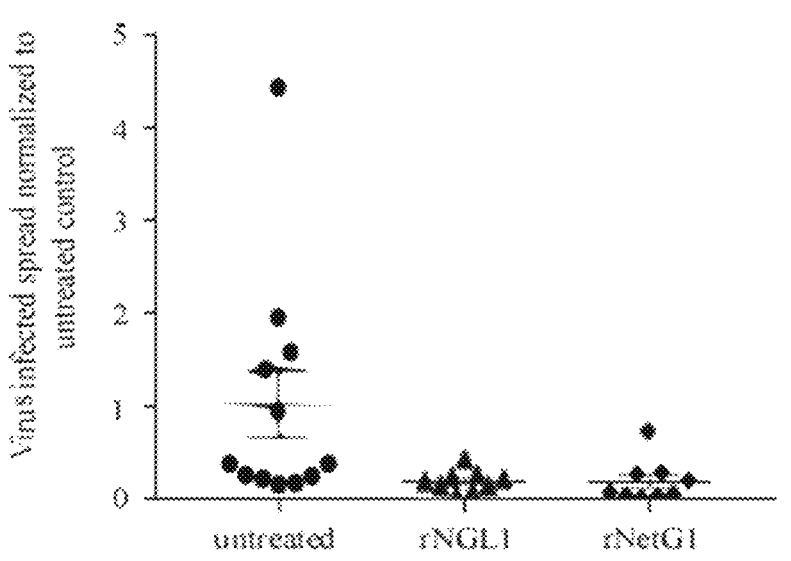
FIG. 3D shows a graphical representation of the data presented in FIG. 3B.

Example 3: Recombinant NGL1 and NetG1 Suppress Cell-to-Cell Viral Transmission Viral transmission was used as a test to investigate the formation of functional synapses. FIG. 3 shows virus (red) infected neurons (green and shown in transmitted light in the bottom panels) cultured while untreated (left) or treated with recombinant NGL1 (middle) or NetG1 (right) to asses functional neural synapse-dependent virus infection (top panels) and neural morphology (bottom panels) (Panel A). Red virus infection was effectively propagated in the absence of treatment and affected more by treatment with recombinant NGL1 and NetG1, suggesting polarity of pre-/post-synaptic virus infection under these conditions. The same experiment, as in Panel A, was conducted, except that virus (red) infected neurons (green) were plated onto a CAF culture bed (evident in transmitted microscopy images shown in bottom panels) to assess heterotypic neuron-CAF functional synapse formation (evidence by red virus spread into CAFs) while untreated (left) or treated with recombinant NGL1 (middle) or NetG1 (right) (Panel B). Neurons were infected with viruses that can only be transmitted via functional synapses and demonstrated that preventing NetG1/NGL1 engagement limited virus transmission, suggesting functional synapses were disturbed (FIG. 3C). Neurons were infected and functional synapses were also observed between neurons and fibroblasts, which were prevented when the recombinant NetG1 or NGL1 were used (FIG. 3D), again suggesting that preventing heterotypic synapse formation is effectively achieved when blocking cellular NetG1/NGL1 interactions (as outcompeted by the recombinant proteins added to the culture media).

Example 4: Immune Cells Switch from NGL1 to NetG1 Expression on Activation

Figure 4A:
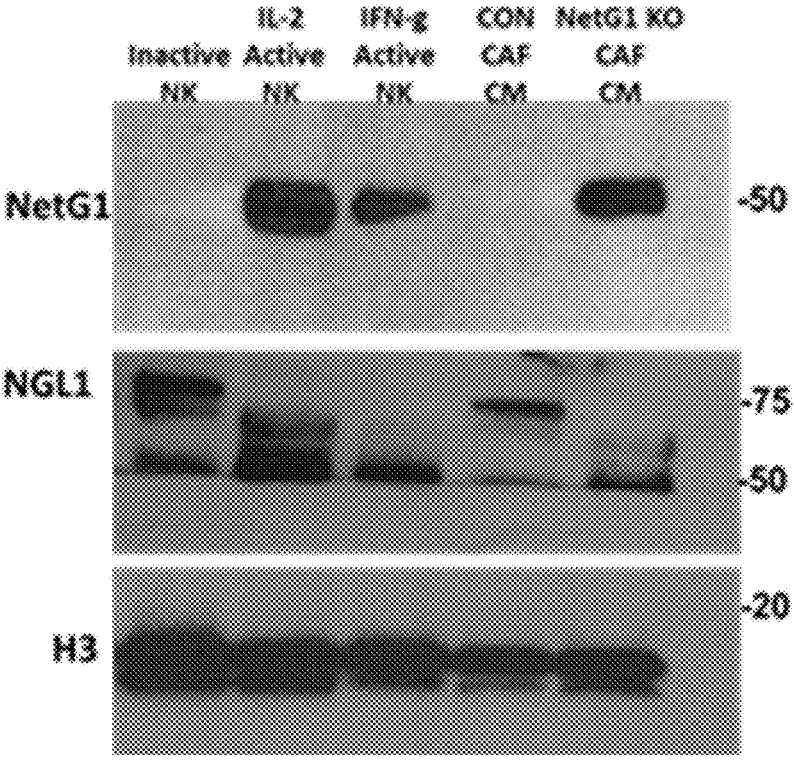
FIG. 4A shows a Western blot demonstrating that NK cells undergo a molecular switch between NetG1 and NGL1 expression, when active or inactive, respectively.

NK92 Cells ($10^6$) were cultured in the presence of Alpha-Mem media without IL-2 (Inactive NK), 500 units/mL SIL-2 (IL-2 Active NK), 50 ng/mL IFN-g (IFN-g Active NK), 500 units/mL IL-2 and CON CAF CM (CON CAF CM), or 500 units/mL IL-2 and NetG1 KO CAF CM (NetG1 KO CAF CM) for 24 hours. NetG1 and NGL1 expression were probed by Western blotting. H3 was used as a loading control. The results showed that NK cells undergo a molecular switch between NetG1 and NGL1 expression, when active or inactive, respectively (see, FIG. 4A). This suggests that immune cells could alter the expression of these proteins to potentially engage with different cells and promote or inhibit their polarization/activity (see similar example below with T cells).

Figure 4B:
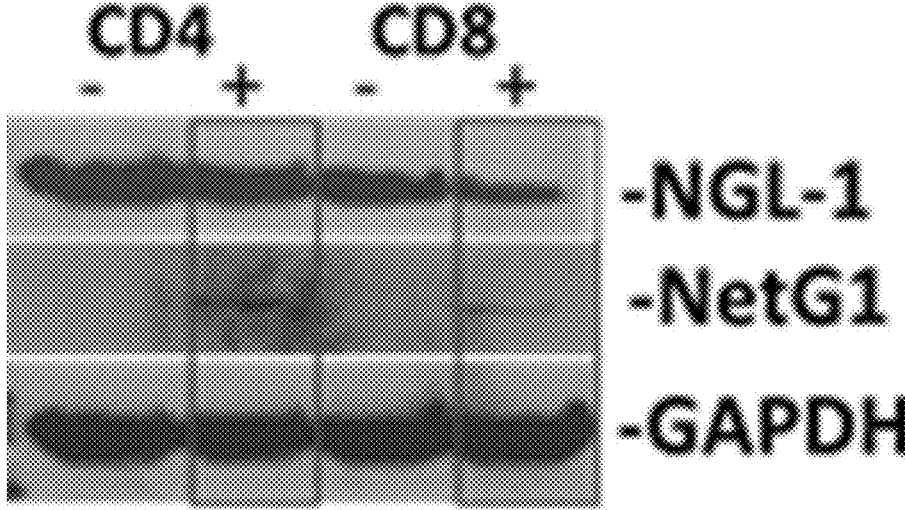
FIG. 4B shows a Western blot demonstrating that CD4+ and CD8+ T cells undergo a molecular switch between expression of both NetG1 and NGL1 expression when active and sole expression of NGL1 when inactive.
Figure 4C:
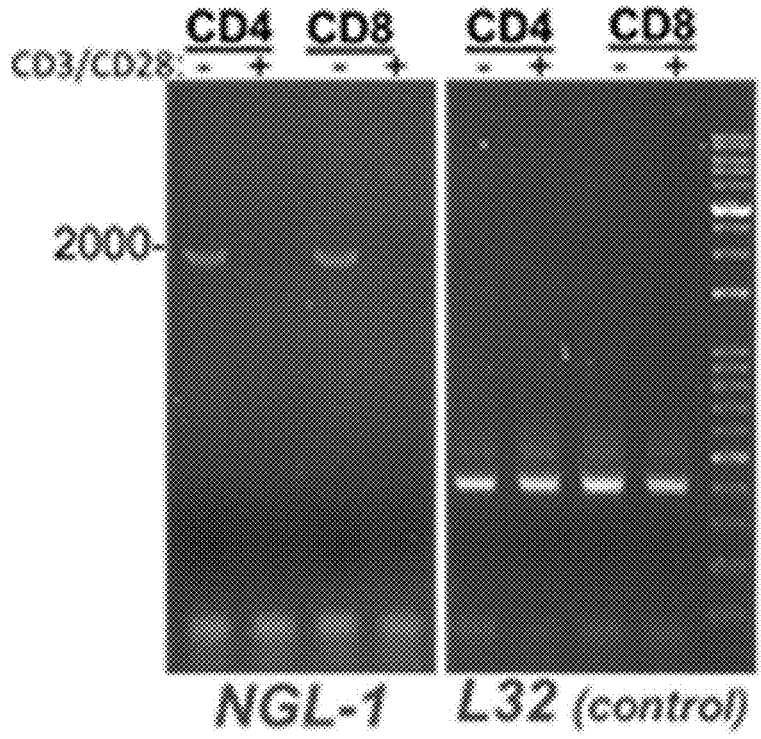
FIG. 4C shows an RT-PCR assay demonstrating that CD4+ and CD8+ T cells undergo a molecular switch lowering mRNA levels of NGL1 expression, when active.

CD4 and CD8 T cells sorted from spleen of a naive C57BL6 mouse were stimulated with CD3/CD28 (1:1000 and 1:2000) for 3 days, in T cells media. The results showed that that CD4 and CD8 cells undergo a molecular switch between NetG1 and NGL1 expression, when active or inactive, respectively as shown by protein (see, FIG. 4B) and RNA (see, FIG. 4C) assays. Gate strategies: Live (sytox blue neg)/CD3 (FITC)/CD4$^+$(APC)-CD8$^+$ (PeCy7). Antibodies: anti-NetG1 1:100 Sta Cruz, anti-NGL-1 1:1000 Genetex, anti-GAPDH 1:10000 Abcam.

Figure 4D:
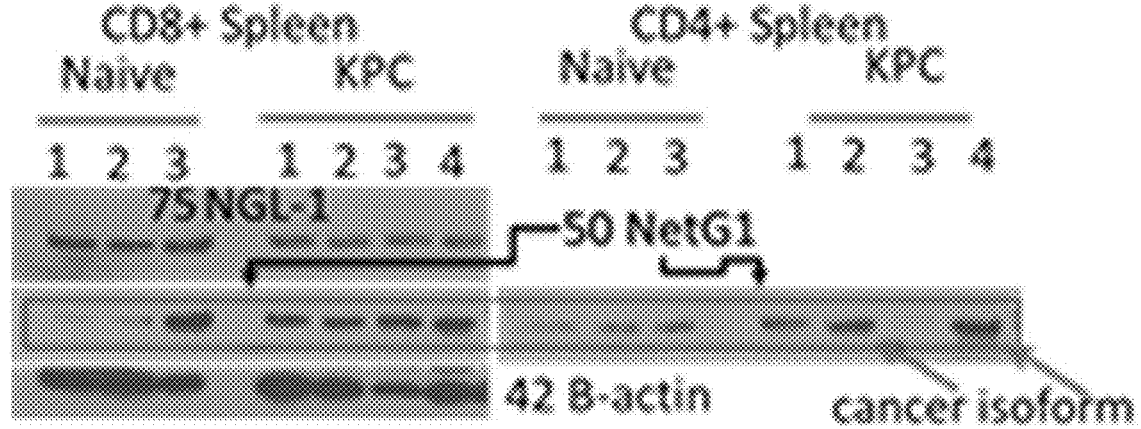
FIG. 4D shows a Western blot demonstrating that NetG1 expression is higher in CD4+ and CD8+ T cells in tumor bearing mice.

Spleens and bone marrow from naive and KPC tumor bearing mice (a spontaneous genetic PDAC model) were processed and submitted to FACS sorting for the following populations: T cells: live/CD3/CD4 and live/CD3/CD8 cells. Monocytes: live/CDI11b$^+$/CDIIb$^+$/Ly6C$^+$ high cells Neutrophils: live/CDIIb$^+$/Ly6G$^+$ cells. After sorting, proteins were isolated and Western blotting was performed for detection of NetG1 and NGL-1. Each naive is a pool of 3 animals; KPC represented by individual mice. The results showed that NetG1 expression was higher in CD4$^+$ and CD8$^+$ T cells in tumor bearing mice (see, FIG. 4D).

Antibodies: FACS-BD Biosciences, all 1:100 Anti CD3 (PE), anti CD4 (APC), anti CD8 (PeCy7), anti-CD11b (APC-Cy7), anti-Ly6C (APC), anti-Ly6G (FITC). For dead cells, sytox blue exclusion dye was used. WB-NetG1 Santa Cruz 1:100, NGL-1 Genetex 1:1000, beta-actin Cell Signaling 1:5000.

Figure 4E:
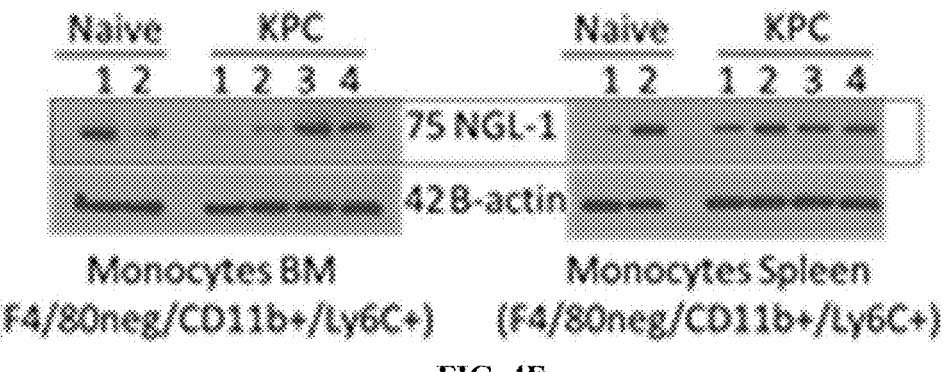
FIG. 4E shows a Western blot demonstrating that monocytes from both naive and tumor bearing mice express NGL-1.
Figure 4F:
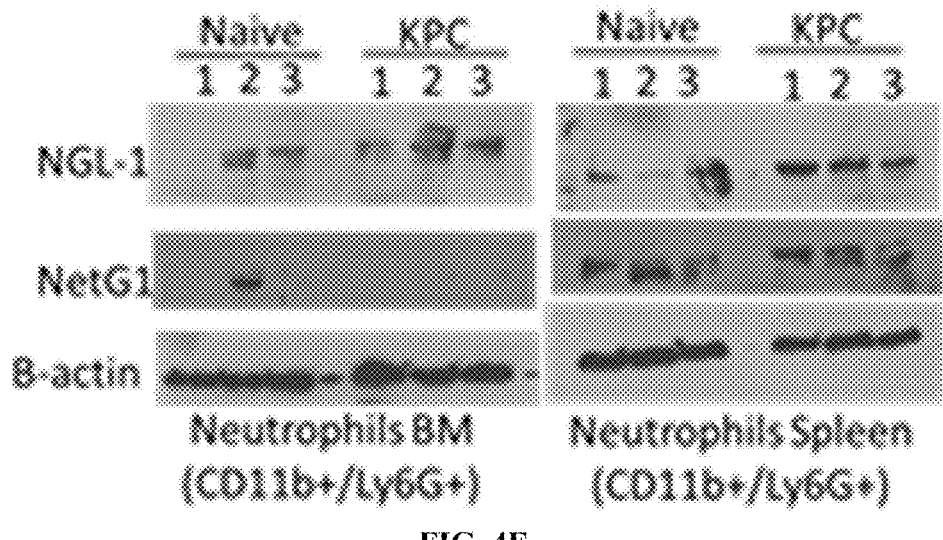
FIG. 4F shows a Western blot demonstrating that NGL-1 expression is greater in neutrophils from tumor-bearing mice (PMN-MDSCs) in the spleen.

NGL-1 expression tends to be higher in neutrophils from tumor-bearing mice (PMN-MDSCs) in the spleen, where they are immunosupressive. In contrast, neutrophils from tumor bearing mice, which potentially are immunosuppressive and called myeloid-derived suppressor cells if so, tend to overexpress NGL-1 (see, FIG. 4F). In contrast, there was no clear difference in NGL 1 expression between monocytes from naive and KPC tumor bearing mice (see, FIG. 4E).

Each naive is a pool of 3 animals; KPC represented by individual mice. Anti-NetG1 (Santa Cruz, 1:250). Anti-NGL-1 (Genetex, 1:500). B-actin-HRP (Cell Signaling, 1:5000)

Figure 4G:
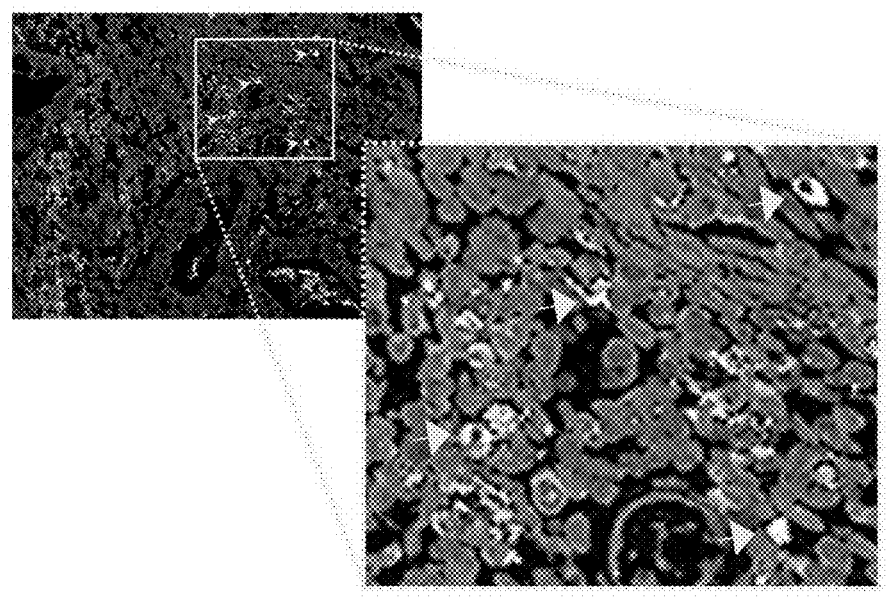
FIG. 4G shows detection of immune infiltrates in human PDAC surgical sample: tumor cells (pan-cytokeratin); nuclei (Draq5); T-cells (CD3); NetrinG1; active immune cell (i.e., granzymeB); and NK cell (NKP46); active NK cells are triple labeled (indicated by the arrows).

A human pancreatic cancer surgical sample was examined (see, FIG. 4G). A formalin fixed and paraffin embedded human surgical sample was stain simultaneously with markers to identify immune cell infiltrates, such as T cells and NK cells, and investigate that NetG1 expression correlates with immune cells presenting with activation markers, such as granzymeB. The provided staining included: pan-cytokeratin (in purple), nuclei (Draq5, in gray), T-cells (anti-CD3, in cyan); NetrinG1 (in red), granzymeB to recognize active immune cells (in blue) and NK cells (anti-NKP46 in green). Active NK cells can be recognized in the multiplexed image via triple labeled (in red, green and blue; appearing as white cells pointed by the yellow/white arrows). The results demonstrate that the NetrG1 molecular switch observed using Western Blots can also be detected in vivo.

Example 5: Recombinant NGL1 Suppresses Rescue of Starvation-Induced Death of PDAC Cancer Cells PDAC cells die in the absence of nutrition but can be rescued using EVs secreted by intact CAFs. If CAFs are deficient in NetG1 expression, the resultant EVs fail to rescue PDAC cells from starvation. Adding recombinant NetG1 to EVs produced by CAFs lacking NetG1 can again provide a survival benefit to PDAC cells under nutritional stress, suggesting that recombinant NetG1 can engage with NGL1 in PDAC cells and trigger its engagement to activate its survival (potentially provided by the EVs). The pharmaceutical agents set forth herein will prevent the NetG1/NGL1 engagement and, thus, serve as therapeutics that will assure PDAC cells will not survive under nutritional stress as in vivo. As shown in FIG. 5 (Panels A and B), CAF-produced EVs are effective in rescuing starvation induced death of PDAC cancer cells which tends to decrease when EVs are pre-incubated with recombinant NGL1 (Pane A), and the recombinant NetG1 treatment of KRAS-transformed pancreatic cells improves the effectiveness of EVs harvested from NetG1 deficient CAFs (NG1KO) in rescuing starvation-induced death of PDAC cancer cells (Panel B).

Example 6: Adding Recombinant Netrin G1 (NG1) to T-cells During Activation Prevents Their Polarization Isolated anti-tumoral T cells from murine spleens can be activated (to proliferate) using CD3/CD28 but this activation is prevented in the presence of recombinant NetG1, suggesting that engagement of T cell NGL1 prevents cytotoxic T cell activation. This result suggests again that preventing NGL1 engagement with NetG1 may allow anti-tumor T cell activation in the PDAC microenvironment despite the presence of fibroblastic CAFs and other cells expressing NetG1. FIG. 6 shows that treatment of T-cells with recombinant NetG1 during activation prevents their polarization/activation.

Example 7: A Neutralizing Monoclonal Antibody Targeting NetG1 Reduces Pro-Tumor Properties of CAFs CAFs were treated for 48 hours with increasing amounts of anti-NetrinG1 monoclonal antibody (Santa Cruz; mAb) in serum-free and glutamine-free media. A dose-dependent decrease in proteins associated with pro-tumorigenic pathways was observed (FIG. 8A). A time course treatment of CAFs with 2.5 mg/ml of anti-NetrinG1 monoclonal antibody also resulted in a time-dependent decrease in proteins associated with pro-tumorigenic pathways (FIG. 8B).

PDAC cells (HPNE-E6/E7-Kras/sv40(PDACc) or PANC-1) were co-cultured for 48 hours with CON (10 µg/mL IgG or mAb treated) or NetG1 KO CAFs under serum and glutamine starvation. A significant reduction, as compared to control IgG, was observed under both conditions demonstrating the efficacy of NetG1 mAb in a functional assay (FIG. 8C).

CAFs were treated with IgG or increasing doses of anti-NetG1 mAb for 48 hours and the amounts of secreted glutamate and glutamine in the conditioned media were measured. A dose-dependent decrease of secreted glutamate and glutamine was detected (FIG. 8D).

CAFs were treated with IgG or increasing doses of anti-NetG1 mAb for 48 hours, and the amounts of secreted pro-tumor cytokines in the conditioned media was also measured. A does-dependent decrease of secreted pro-tumor cytokines was detected (FIG. 8E).

CAFs were also cultured within their self-derived ECM (see, Cukierman et al., Science, 2001, 294, 1708-1712), which was needed for NetG1 expression. A one-way ANOVA was used to determine if the samples were significantly different from IgG. * p<. 05,  p<. 01, p<. 001, ** p<0.0001. N=3-8.

Example 8: Blockade of NetG1 Using mAb Decreases Tumorigenesis in a Syngeneic/Orthotopic Murine Model of Pancreatic Cancer C57/BL6 mice were injected orthotoptically with $10^6$ murine pancreatic cancer cells (a KPPC clone) and mice were allowed to heal for 3 days. Starting on day 4, mice were randomized into two groups, IgG (n=9) and mAb (n=10), which were treated with either 5 mg/kg IgG or mAb against NetG1. Mice were treated 3 times per week until the completion of the model, at day 21. Pancreata were isolated from each mouse and H+E sections were obtained from a middle cut spanning the entire pancreas. The weight and the % area of tumors was measured and both weight (FIG. 9A) and tumor area (FIG. 9B) were significantly decreased following NetG1 antibody treatment. The total weight of the pancreas was also determined (FIG. 9C), showing a decrease following NetG1 antibody treatment. In addition, the area of pancreas occupied by necrotic tissue was quantified (FIG. 9D).

A small piece of tumor tissue (30-60 mg) was excised from the pancreas of each mouse and cultured overnight in DMEM lacking serum, glutamate (Glu) and glutamine (Gln). The resultant media was collected and the amount of Glu and Gin was measured by ELISA and normalized to the weight of the tumor tissue cultured and graphed as the fold change concentration relative to the IgG treated animals. The amount of Glu was significantly decreased following NetG1 antibody treatment (FIG. 9E). The amount of Gln was also decreased following NetG1 antibody treatment, but this decrease was not statistically significant (FIG. 9F). A Student's T-Test was used to determine if the samples were significantly different from IgG. * p<0.05,  p<0.01, * p<0.001, **** p<0.0001. n=9 for IgG, n=10 for mAb.

Example 9: Systemic Loss of NGL1 in Mice Impedes PDAC Tumorigenesis

Wild type (WT, n=6) or NGL1 Knockout (KO, n=7) C57/BL6 mice were injected orthoptically with $10^6$ syngeneic murine pancreatic cancer cells (KPPC from a clone) and mice were observed until the completion of the model at day 21. Pancreata were isolated from each mouse and H+E sections were developed from a cut of the entire pancreas. The weight of the tumors was measured and a significant decrease in NGL-1 KO mice was observed (FIG. 10A). The % area of cells that classified as normal also increased in NGL-1 KO mice, although this difference was not statistically significant (FIG. 10B). Likewise, no statistically significant difference was observed for the % of tumors cells that were classified as poorly differentiated (often associated with more aggressive tumors) (FIG. 10C).

A small piece (30-60 mg) of tumor was excised from the pancreas of each mouse and was cultured overnight in serum-free DMEM. The resultant conditioned media was probed for TGF-β and IL-6 protein levels by ELISA. The concentration of each cytokine measured was normalized to the weight of the tumor tissue cultured. A significant decrease was observed for both TGF-β and IL-6 protein levels in NGL-1 KO mice (FIG. 10D).

CD4 or CD8 T-cells were isolated from the spleens of healthy WT or KO mice using FACS. These cells were then either not stimulated (neg) or stimulated (pos) with CD3/CD28 activating antibody to induce proliferation of the T-cells. Both CD4 and CD8 T-cells isolated from KO mice displayed more proliferation when compared to the same cells isolated from WT mice (FIG. 10E). A one-way ANOVA was used to determine if the samples were significantly different from WT. * $p <. 001$, ** $p < 0001$. n=9.

Example 10: Inhibition of NGL1 with Therapeutic Peptides Reduces Pro-Tumorigenic Cytokine Secretion by CAFs $1.6 \times 10^5$ Control (CON) or NetrinG1 Ligand knockdown (NGL1 KD) CAFs were plated into 24 well plates and allowed to produce matrices in the presence of 50 µg/mL of ascorbic acid and were either untreated or treated with either soluble NetrinG1 (sNG1), NetG1 peptide corresponding to a domain known to engage with NGL1 (NPYMSNNE; SEQ ID NO:26; (FITC)—Ba-Asn-Pro-Tyr-Met-Ser-Asn-Asn-Glu-(NH2)), hypothesized to modestly prevent NetG1/NGL1 interaction (peptide), or a modified NetG1 peptide (NPTMSNNE; SEQ ID NO:27; (FITC)—Ba-Asn-Pro-Thr-Met-Ser-Asn-Asn-Glu-(NH2)) suspected to strongly prevent NetG1/NGL1 engagement (mutant), for 7 days. A decision was made to mutate the original sequence from Cys to Ser assuming that for these short peptides, disulfide bonds will not be able to be made, hence to better mimic the potential interaction with NGL1 (and better prevent NetG1/NGL1 interaction). The media was then replaced with serum- and glutamine-free media and CAFs were allowed to condition the media for 2 days. Conditioned media was collected from each well and subjected to ELISA for the measurement of cytokine (TGF-β, IL-6, and IL-8) secretion. All sNG1, peptides, and NGL1 KD treatments resulted in significant decreases in levels of secreted TGF-β (FIG. 10A), IL-6 (FIG. 10B), and IL-8 (FIG. 10B). A one-way ANOVA was used to determine if samples were significantly different from CON. * $p<05$,  $p<. 01$, * $p<. 001$, **** $p<. 0001$. N=3-6.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. An isolated Netrin G1 (NetG1) polypeptide comprising a NetG1 peptide moiety of up to 20 amino acids wherein:

the NetG1 peptide moiety comprises: SEQ ID NO: 1, SEQ ID NO: 16, SEQ ID NO: 17, SEQ ID NO: 18, SEQ ID NO:2, SEQ ID NO: 19, SEQ ID NO:9, SEQ ID NO:22, SEQ ID NO:23, SEQ ID NO:24, SEQ ID NO: 10, SEQ ID NO:25, SEQ ID NO: 14, SEQ ID NO:26, SEQ ID NO: 15, or SEQ ID NO:27; and wherein the NetG1 polypeptide is linked or fused to a heterologous polypeptide or is labeled with a detectable label.

2. The isolated NetG1 polypeptide according to claim 1, wherein:

the NetG1 polypeptide comprises up to 18 amino acids and comprises SEQ ID NO:1;

the NetG1 polypeptide comprises up to 18 amino acids and comprises SEQ ID NO:16;

the NetG1 polypeptide comprises up to 18 amino acids and comprises SEQ ID NO:17;

the NetG1 polypeptide comprises up to 18 amino acids and comprises SEQ ID NO:18;

the NetG1 polypeptide comprises up to 13 amino acids and comprises SEQ ID NO:2;

the NetG1 polypeptide comprises up to 13 amino acids and comprises SEQ ID NO:19;

the NetG1 polypeptide comprises up to 18 amino acids and comprises SEQ ID NO:9;

the NetG1 polypeptide comprises up to 18 amino acids and comprises SEQ ID NO:22;

the NetG1 polypeptide comprises up to 18 amino acids and comprises SEQ ID NO:23;

the NetG1 polypeptide comprises up to 18 amino acids and comprises SEQ ID NO:24;

the NetG1 polypeptide comprises up to 13 amino acids and comprises SEQ ID NO:10;

the NetG1 polypeptide comprises up to 13 amino acids and comprises SEQ ID NO:25;

the NetG1 polypeptide comprises up to 12 amino acids and comprises SEQ ID NO:14;

the NetG1 polypeptide comprises up to 12 amino acids and comprises SEQ ID NO:26;

the NetG1 polypeptide comprises up to 12 amino acids and comprises SEQ ID NO: 15; or the NetG1 polypeptide comprises up to 12 amino acids and comprises SEQ ID NO:27.

3. The isolated NetG1 polypeptide according to claim 1, wherein the NetG1 polypeptide is linked or fused to a heterologous polypeptide.

4. The isolated NetG1 polypeptide according to claim 3, wherein the heterologous polypeptide is an affinity tag, a fluorescent protein, or an epitope tag.

5. The isolated NetG1 polypeptide according to claim 1, wherein the NetG1 polypeptide is labeled with a fluorescent label or a radiolabel.

6. A composition comprising the NetG1 polypeptide according to claim 1, and a pharmaceutically acceptable carrier.

*    *    *    *    *